US009125885B2

(12) United States Patent
Nitzel et al.

(10) Patent No.: US 9,125,885 B2
(45) Date of Patent: *Sep. 8, 2015

(54) PCV/MYCOPLASMA HYOPNEUMONIAE COMBINATION VACCINE

(71) Applicant: Zoetis Services LLC, Florham Park, NJ (US)

(72) Inventors: Gregory P. Nitzel, Paw Paw, MI (US); Jeffrey E. Galvin, Lincoln, NE (US); John Keith Garrett, North Wilkesboro, NC (US); James R. Kulawik, II, Lincoln, NE (US); Tracy L. Ricker, Portage, MI (US); Megan Marie Smutzer, Kalamazoo, MI (US)

(73) Assignee: Zoetis Services LLC, Florham Park, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/850,329

(22) Filed: Mar. 26, 2013

(65) Prior Publication Data

US 2013/0266602 A1 Oct. 10, 2013

Related U.S. Application Data

(60) Provisional application No. 61/620,175, filed on Apr. 4, 2012.

(51) Int. Cl.
*A61K 39/295* (2006.01)
*A61K 39/02* (2006.01)
*A61K 39/12* (2006.01)
*A61K 39/00* (2006.01)

(52) U.S. Cl.
CPC ............ *A61K 39/295* (2013.01); *A61K 39/0241* (2013.01); *A61K 39/12* (2013.01); *A61K 2039/5252* (2013.01); *A61K 2039/552* (2013.01); *A61K 2039/55566* (2013.01); *A61K 2039/70* (2013.01); *C12N 2750/10034* (2013.01)

(58) Field of Classification Search
None
See application file for complete search history.

(56) References Cited

U.S. PATENT DOCUMENTS

| | | | |
|---|---|---|---|
| 4,606,918 A | 8/1986 | Allison et al. | |
| 4,681,870 A * | 7/1987 | Balint et al. | 502/403 |
| 5,080,896 A | 1/1992 | Visser et al. | |
| 5,240,706 A | 8/1993 | Faulds et al. | |
| 5,338,543 A | 8/1994 | Fitzgerald et al. | |
| 5,534,256 A | 7/1996 | Potter et al. | |
| 5,565,205 A | 10/1996 | Petersen et al. | |
| 5,620,691 A | 4/1997 | Wensvoort et al. | |
| 5,695,766 A | 12/1997 | Paul et al. | |
| 5,695,769 A | 12/1997 | Frantz et al. | |
| 5,788,962 A | 8/1998 | Wise et al. | |
| 5,846,735 A | 12/1998 | Stapleton et al. | |
| 6,110,467 A | 8/2000 | Paul et al. | |
| 6,113,916 A | 9/2000 | Bhogal et al. | |
| 6,162,435 A | 12/2000 | Minion et al. | |
| 6,193,971 B1 | 2/2001 | Hofmann et al. | |
| 6,251,397 B1 | 6/2001 | Paul et al. | |
| 6,251,404 B1 | 6/2001 | Paul et al. | |
| 6,268,199 B1 | 7/2001 | Meulenberg et al. | |
| 6,342,231 B1 | 1/2002 | Burkhardt et al. | |
| 6,380,376 B1 | 4/2002 | Paul et al. | |
| 6,500,662 B1 | 12/2002 | Calvert et al. | |
| 6,585,981 B1 | 7/2003 | Pijoan | |
| 6,592,873 B1 | 7/2003 | Paul et al. | |
| 6,753,417 B2 | 6/2004 | Hansen et al. | |
| 6,773,908 B1 | 8/2004 | Paul et al. | |
| 6,846,477 B2 | 1/2005 | Keich et al. | |
| 6,977,078 B2 | 12/2005 | Paul et al. | |
| 7,018,638 B2 | 3/2006 | Chu et al. | |
| 7,056,492 B2 * | 6/2006 | Goudie et al. | 424/9.2 |
| 7,074,894 B2 | 7/2006 | Walker et al. | |
| 7,169,394 B2 | 1/2007 | Chu et al. | |
| 7,223,854 B2 | 5/2007 | Paul et al. | |
| 7,264,802 B2 | 9/2007 | Paul et al. | |
| 7,264,957 B2 | 9/2007 | Paul et al. | |
| 7,279,166 B2 * | 10/2007 | Meng et al. | 424/199.1 |
| 7,419,806 B2 | 9/2008 | Minion et al. | |
| 7,517,976 B2 | 4/2009 | Paul et al. | |
| 7,575,752 B2 | 8/2009 | Meng et al. | |
| 7,622,124 B2 | 11/2009 | Chu et al. | |
| 7,959,927 B2 | 6/2011 | Chu et al. | |
| 8,008,001 B2 * | 8/2011 | Roerink et al. | 435/5 |
| 8,187,588 B2 | 5/2012 | Chu et al. | |
| 8,444,989 B1 | 5/2013 | Ohnesorge et al. | |
| 2002/0114817 A1 | 8/2002 | Liem et al. | |

(Continued)

FOREIGN PATENT DOCUMENTS

| | | |
|---|---|---|
| EP | 0283085 A1 | 9/1988 |
| EP | 0315153 A2 | 5/1989 |

(Continued)

OTHER PUBLICATIONS

Zahn et al. (Journal of General Virology 2005; 86: 677-685).*
Redegeld et al. (Nature Medicine. 2002; 8 (7): 694-701).*
Djordjevic et al. "Serum and mucosal antibody responses and protection in pigs vaccinated against *Mycoplasma hyopneumoniae* with vaccines containing a denatured membrane antigen pool and adjuvant", Australian Veterinary Journal. vol. 75 No. 7, pp. 504-511, Jul. 1, 1997.
Chen et al. "Evaluation of immune response to recombinant potential protective antigens of *Mycoplasma hyopneumoniae* delivered as cocktail DNA and/or recombinant protein vaccines in mice", Vaccine, vol. 26, No. 34, pp. 4372-4378, Aug. 12, 2008.

(Continued)

*Primary Examiner* — Shanon A Foley
(74) *Attorney, Agent, or Firm* — Gloria K. Szakiel; Barbara L. Renda

(57) ABSTRACT

This invention provides a multivalent immunogenic composition including a soluble portion of a *Mycoplasma hyopneumoniae* (*M. hyo*) whole cell preparation; and a porcine circovirus type 2 (PCV2) antigen, wherein the soluble portion of the *M. hyo* preparation is substantially free of both (i) IgG and (ii) immunocomplexes comprised of antigen bound to immunoglobulin.

26 Claims, 10 Drawing Sheets

(56) References Cited

U.S. PATENT DOCUMENTS

| | | | |
|---|---|---|---|
| 2005/0079185 A1* | 4/2005 | Parisot et al. | 424/184.1 |
| 2009/0317423 A1 | 12/2009 | Roof et al. | |
| 2012/0052514 A1 | 3/2012 | Allen et al. | |
| 2013/0266602 A1* | 10/2013 | Nitzel et al. | 424/186.1 |

FOREIGN PATENT DOCUMENTS

| | | |
|---|---|---|
| EP | 0595436 A2 | 5/1994 |
| EP | 2 275 132 A2 | 1/2011 |
| GB | 2282811 | 4/1995 |
| WO | WO 91/03157 | 3/1991 |
| WO | WO 91/18627 | 12/1991 |
| WO | WO 92/21375 | 12/1992 |
| WO | WO 93/03760 | 3/1993 |
| WO | WO 93/07898 | 4/1993 |
| WO | WO 93/10216 | 5/1993 |
| WO | WO 93/14196 | 7/1993 |
| WO | WO 95/30437 | 11/1995 |
| WO | WO 96/28472 A1 | 9/1996 |
| WO | WO 96/40268 | 12/1996 |
| WO | WO 02/10343 A2 | 2/2002 |
| WO | WO 02/49666 A2 | 6/2002 |
| WO | WO 03/049703 A2 | 6/2003 |
| WO | 2004058142 A2 | 7/2004 |
| WO | WO 2007/116032 A1 | 10/2007 |
| WO | WO 2009/126356 A2 | 10/2009 |
| WO | WO 2011/141443 A1 | 11/2011 |
| WO | WO 2012/063212 A1 | 5/2012 |

OTHER PUBLICATIONS

Drexler et al. "Efficacy of combined porcine reproductive and respiratory syndrome virus and *Mycoplasma hyopneumoniae* vaccination in piglets", Veterinary Record, vol. 166 No. 3, pp. 70-74, Jan. 16, 2010.

Grau-Roma et al. "Recent advances in the epidemiology, diagnosis and control of diseases caused by porcine circovirus type 2", Veterinary Journal, vol. 187 No. 1, pp. 23-32, Jan. 1, 2011.

Okada et al. "Cytological and immunological changes in brochoalveolar lavage fluid and histological observation of lung lesions in pigs immunized with *Mycoplasma hyopneumoniae* inactivated vaccine prepared from broth culture supernate", Vaccine, vol. 18, No. 25, pp. 2825-2831, Jun. 1, 2000.

Okada M,et al. "Evaluation of *Mycoplasma hyopneumoniae* inactivated vaccine in pigs under field conditions", J. Vet. Med. Science, vol. 61 No. 10, pp. 1131-1135, Jun. 25, 1999.

Genzow Marika et al. "Concurrent vaccination of piglets with Ingelvac® PRRS MLV and with Ingelvac® M. hyo", Tieraerztliche Umschau, vol. 61 No. 12, pp. 649-652, Dec. 1, 2006.

Xin-Gang et al. "Baculovirus as a PRRSV and PCV2 bivalent vaccine vector: Baculovirus virions displaying simultaneously GP5 glycoprotein of PRRSV and capsid protein of PCV2", Journal of Virological Methods, vol. 179 No. 2, pp. 359-366, Nov. 28, 2011.

Ross "Characteristics of a protective activity of *Mycoplasma hyopneumoniae* vaccine" American Journal of Veterinary Research, vol. 45, No. 10, pp. 1899-1905, Oct. 1984.

Fort Dodge Australia (2000) TechNote—Technical Update TF S04-00 (1) "Suvaxyn M.Hyo—How it works".

Collins et al. "Isolation of Swine Infertility and Respiratory Syndrome Virus (Isolate ATCC VR-2332) in North America and Experimental Reproduction of the Disease in Gnotobiotic Pigs" Journal of Veterinary Diagnostic Investigation 1992, 4:117-126.

Kwang, J. et al. "Cloning, Expression, and Sequence Analysis of the ORF4 Gene of the Porcine Reproductive and Respiratory Syndrome Virus MN-1b" Journal of Veterinary Diagnostic Investigation 1994, 6:293-296.

Mardassi, H. et al. "Molecular Analysis of the ORFs 3 to 7 of Porcine Reproductive and Respiratory Syndrome Virus, Quebec Reference Strain" Archives of Virology 1995, 140: 1405-1418.

Meng, X.-J. et al. "Molecular Cloning and Nucleotides Sequencing of the 3'-Terminal Genomic RNA of the Porcine Reproductive and Respiratory Syndrome Virus" Journal of General Virology 1994, 75:1795-1801.

Wensvoort, G. et al. "Mystery Swine Disease in the Netherlands: the Isolation of Lelystad Virus" The Veterinary Quarterly 1991, 13:121-130.

Kim et al. "Identification and Mapping of an Immunogenic Region of *Mycoplasma hyopneumoniae* p65 Surface Lipoprotein Expressed in *Escherichia coli* from a Cloned Genomic Fragment" Infection and Immunity 1990, 58:2637-2643.

Futo et al. "Molecular Cloning of a 46-Kilodalton Surface Antigen (P46) Gene from *Mycoplasma hyopneumoniae:* Direct Evidence of CGG Codon Usage for Arginine" Journal of Bacteriology 1995, 177:1915-1917.

Zhang et al. "Identification and Characterization of a *Mycoplasma hyopneumoniae* Adhesin" Infection and immunity 1995, 63: 1013-1029.

King et al. "Characterization of the Gene Encoding Mhp1 from *Mycoplasma hyopneumoniae* and Examination of Mhp1's Vaccine Potential" Vaccine 1997, 15:25-35.

Okada et al. "Protective Effect of Vaccination with Culture Supernate of *M.hyopneumoniae* Against Experimental Infection in Pigs" Journal of Veterinary Medicine 2000, 47:527-533

Scarman et al. "Identification of Novel Species-Specific Antigens of *Mycoplasma hyopneumoniae* by Preparative SDS-PAGE ELISA Profiling" Microbiology 1997, 143:663-673.

Strait et al. "Efficacy of a *Mycoplasma hyopneumoniae* Bacterin in Pigs Challenged With Two Contemporary Pathogenic isolates of *M hyopneumoniae*" Journal of Swine Health and Production 2008, 16:200-206.

Alexander et al. "Adjuvants and their Modes of Action" Livestock Production Science 1995, 42:153-162

Hunter et al. "The Adjuvant Activity of Nonionic Block Polymer Surfactants" The Journal of Immunologists 1981, 127:1244-1250.

Allison "Squalene and Squalane Emulsions as Adjuvants" Methods 1999, 19:87-93.

Goodwin et al. "Enzootic Pneumonia of Pigs: Immunization Attempts Inoculating *Mycoplasma suipneumoniae* Antigen by Various Routes and with Different Adjuvants" British Veterinary Journal 1973, 129:456-464.

George et al. "Route-Related Variation in the Immunogenicity of Killed Salmonella Enteritidis Vaccine: Role of Antigen Presenting Cells" Microbiol Immunol 1989, 33:479-488.

Byars et al. "Adjuvant Formulation for use in Vaccines to Elicit Both Cell-Mediated and Humoral Immunity" Vaccine 1987, 5:223-228.

Martinon et al. "Efficacy of a 'One Shot' Schedule of a *Mycoplasma hyopneumoniae* Bacterin (Hyoresp)" Proceedings of the 15$^{th}$ IPVS Congress, Birmingham, England, Jul. 5-9, 1998, p. 284.

Reynaud et al. "Clinical Field Trial With *Mycoplasma hyopneumoniae* Bacterin (Hyoresp)" Proceedings of the 15$^{th}$ IPVS Congress, Birmingham, England, Jul. 5-9, 1998 p. 150.

Charlier et al. "Comparative Efficacy of Stellamune *Mycoplasma* and Hyoresp in Pigs Against an Experimental Challenge with *Mycoplasma hyopneumoniae*" The 16$^{th}$ International Pig Veterinary Society Congress, Melbourne, Australia Sep. 17-20, 2000 p. 501.

Sheldrake et al. "Evaluation of an enzyme-linked immunosorbent assay for the detection of *Mycoplasma hyopneumoniae* antibody in porcine serum" Australian Veterinary Journal vol. 69, No. 10, Oct. 1992.

* cited by examiner

| Contrast | Mitigated Fraction | 95% confidence interval |
|---|---|---|
| T01 vs T02 | 41.2 | -5.9 to 76.5 |
| T01 vs T03 | 64.7 | 29.4 to 100 |
| T01 vs T04 | 76.5 | 41.2 to 100 |
| T01 vs T05 | 73.3 | 33.3 to 100 |
| T01 vs T06 | 62.5 | 25 to 100 |
| T01 vs T07 | 87.5 | 62.5 to 100 |
| T01 vs T08 | 88.2 | 64.7 to 100 |

Figure 10

| Preliminary Viricidal Activity | Difference from Water | | | |
|---|---|---|---|---|
| | 100% rehyd. Lyophilized Titer | 90/10 Liq. (DMEM) 90/10 | 90/10 Liq. (Ultra) 90/10 | Avg Viricidal Activity |
| 20% SLCD | 0.8 | 0.7 | 2.0 | 1.3 |
| 0.2% Carbopol | 0.3 | -0.3 | 0.2 | -0.1 |
| 10% SP-Oil | 0.2 | 0.0 | 0.0 | 0.0 |
| 10% SP-Oil/0.2% Carbopol | 0.3 | -0.2 | 0.0 | -0.1 |
| 20% SLCD/10% SP-Oil | 1.0 | 0.3 | 0.7 | 0.5 |
| 20% SLCD/10% SP-Oil/0.2% Carbopol | 0.2 | 0.0 | 0.5 | 0.3 |
| 5% Amphigen (from 40% stock) | 1.0 | 0.7 | 1.5 | 1.1 |
| 2.5% Amphigen (from 40% stock) | NA | -0.2 | NA | -0.2 |
| 5% Amphigen (from 20% stock) | NA | 0.8 | NA | 0.8 |
| 2.5% Amphigen (from 20% stock) | NA | 0.2 | NA | 0.2 |
| 5% Amphigen (from 40% stock) | NA | 1.3 | NA | 1.3 |
| 2.5% Amphigen (from 40% stock) | NA | 0.8 | NA | 0.8 |
| | Indicates potential viricidal activity | | | |

SEQUENCE LISTING

```
<160> NUMBER OF SEQ ID NOS: 18

<210> SEQ ID NO 1
<211> LENGTH: 1260
<212> TYPE: DNA
<213> ORGANISM: Mycoplasma hyopneumoniae

<400> SEQUENCE: 1
atgaaaaaaa tgcttagaaa aaaattcttg tattcatcag ctatttatgc aacttcgctt      60
gcatcaatta ttgcatttgt tgcagcaggt tgtggacaga cagaatcagg ttcgacttct     120
gattctaaac cacaagccga gacgctaaaa cataaagtaa gtaatgattc tattcgaata     180
gcactaaccg atccggataa tcctcgatga attagtgctc aaaaagatat tatttcttat     240
```

-continued

```
gttgatgaaa cagaggcagc aacttcaaca attacaaaaa accaggatgc acagaataac    300
tgactcactc agcaagctaa tttaagccca gcaccaaaag gatttattat tgcccctgaa    360
aatggaagtg gagttggaac tgctgttaat acaattgctg ataaaggaat tccgattgtt    420
gcctatgatc gactaattac tggatctgat aaatatgatt ggtatgtttc ttttgataat    480
gaaaaagttg gcgaattaca aggtctttca cttgcagcgg gtctattagg aaaagaagat    540
ggtgcttttg attcaattga tcaaatgaat gaatatctaa aatcacatat gccccaagag    600
acaatttctt tttatacaat cgcgggttcc caagatgata ataactccca atatttttat    660
aatggtgcaa tgaaagtact taaagaatta atgaaaaatt cgggaaataa gataattgat    720
ttatctcctg aaggcgaaaa tgctgtttat gtcccaggat gaaattatgg aactgccggt    780
caaagaatcc aatcttttct aacaattaac aaagatccag caggtggtaa taaaatcaaa    840
gctgttggtt caaaaccagc ttctattttc aaaggatttc ttgccccaaa tgatggaatg    900
gccgarcaag caatcaccaa attaaaactt gaaggatttg atacccaaaa aatctttgta    960
actggtcaag attataatga taaagccaaa acttttatca aagacggcga tcaaaatatg   1020
acaatttata aacctgataa agttttagga aaagttgctg ttgaagttct tcgggtttta   1080
attgcaaaga aaaataaagc atccagatca gaagtcgaaa acgaactaaa agcaaaacta   1140
ccaaatattt catttaaata tgataatcaa acatataaag tgcaaggtaa aaatattaat   1200
acaattttag taagtccagt aattgttaca aaagctaatg ttgataatcc tgatgcctaa   1260
```

```

<210> SEQ ID NO 2
<211> LENGTH: 419
<212> TYPE: PRT
<213> ORGANISM: Mycoplasma hyopneumoniae

<400> SEQUENCE: 2

Met Lys Lys Met Leu Arg Lys Lys Phe Leu Tyr Ser Ser Ala Ile Tyr
1               5                   10                  15

Ala Thr Ser Leu Ala Ser Ile Ile Ala Phe Val Ala Ala Gly Cys Gly
            20                  25                  30

Gln Thr Glu Ser Gly Ser Thr Ser Asp Ser Lys Pro Gln Ala Glu Thr
        35                  40                  45

Leu Lys His Lys Val Ser Asn Asp Ser Ile Arg Ile Ala Leu Thr Asp
    50                  55                  60

Pro Asp Asn Pro Arg Trp Ile Ser Ala Gln Lys Asp Ile Ile Ser Tyr
65                  70                  75                  80

Val Asp Glu Thr Glu Ala Ala Thr Ser Thr Ile Thr Lys Asn Gln Asp
                85                  90                  95

Ala Gln Asn Asn Trp Leu Thr Gln Gln Ala Asn Leu Ser Pro Ala Pro
            100                 105                 110

Lys Gly Phe Ile Ile Ala Pro Glu Asn Gly Ser Gly Val Gly Thr Ala
        115                 120                 125

Val Asn Thr Ile Ala Asp Lys Gly Ile Pro Ile Val Ala Tyr Asp Arg
    130                 135                 140

Leu Ile Thr Gly Ser Asp Lys Tyr Asp Trp Tyr Val Ser Phe Asp Asn
145                 150                 155                 160

Glu Lys Val Gly Glu Leu Gln Gly Leu Ser Leu Ala Ala Gly Leu Leu
                165                 170                 175

Gly Lys Glu Asp Gly Ala Phe Asp Ser Ile Asp Gln Met Asn Glu Tyr
            180                 185                 190

Leu Lys Ser His Met Pro Gln Glu Thr Ile Ser Phe Tyr Thr Ile Ala
```

195                 200                 205
Gly Ser Gln Asp Asp Asn Asn Ser Gln Tyr Phe Tyr Asn Gly Ala Met
    210                 215                 220

Lys Val Leu Lys Glu Leu Met Lys Asn Ser Gly Asn Lys Ile Ile Asp
225                 230                 235                 240

Leu Ser Pro Glu Gly Glu Asn Ala Val Tyr Val Pro Gly Trp Asn Tyr
                245                 250                 255

Gly Thr Ala Gly Gln Arg Ile Gln Ser Phe Leu Thr Ile Asn Lys Asp
            260                 265                 270

Pro Ala Gly Gly Asn Lys Ile Lys Ala Val Gly Ser Lys Pro Ala Ser
        275                 280                 285

Ile Phe Lys Gly Phe Leu Ala Pro Asn Asp Gly Met Ala Glu Gln Ala
    290                 295                 300

Ile Thr Lys Leu Lys Leu Glu Gly Phe Asp Thr Gln Lys Ile Phe Val
305                 310                 315                 320

Thr Gly Gln Asp Tyr Asn Asp Lys Ala Lys Thr Phe Ile Lys Asp Gly
                325                 330                 335

Asp Gln Asn Met Thr Ile Tyr Lys Pro Asp Lys Val Leu Gly Lys Val
            340                 345                 350

Ala Val Glu Val Leu Arg Val Leu Ile Ala Lys Lys Asn Lys Ala Ser
        355                 360                 365

Arg Ser Glu Val Glu Asn Glu Leu Lys Ala Lys Leu Pro Asn Ile Ser
    370                 375                 380

Phe Lys Tyr Asp Asn Gln Thr Tyr Lys Val Gln Gly Lys Asn Ile Asn
385                 390                 395                 400

Thr Ile Leu Val Ser Pro Val Ile Val Thr Lys Ala Asn Val Asp Asn
                405                 410                 415

Pro Asp Ala

<210> SEQ ID NO 3
<211> LENGTH: 3324
<212> TYPE: DNA
<213> ORGANISM: Mycoplasma hyopneumoniae

<400> SEQUENCE: 3
atgagtaaaa aatcaaaaac atttaaaatt ggtttgactg ccggaattgt tggtcttgga      60 gttttggtc taactgtcgg acttagcagc ttgcaaaaat acagatcaga aagtccacga     120
aagattgcaa atgattttgc cgcaaaagtt tcaacattag cttttagtcc ttatgctttt     180
gagactgatt ctgattataa aatagtcaaa aggtgactag ttgattctaa taacaatatt     240
agaaataaag aaaagttat tgattccttt tccttttta ctaaaaacgg tgatcagtta     300
gaaaaaatta attttcaaga tcctgaatat accaaggcga agataacttt tgagattctt     360
gaaattatcc ctgatgatgt caatcaaaat tttaaggtaa aatttcaggc attacaaaaa     420
cttcataatg gtgatattgc caaatctgat atttatgagc aaacagttgc ttttgccaaa     480
cagtcaaatc ttttagttgc cgaatttaat ttttcgctta aaaaaattac cgaaaaatta     540
aatcaacaaa ttgaaaattt atcaacaaaa attacaaatt ttgctgatga aaaaacaagc     600
agccaaaaag atccctcaac tctaagagct attgacttcc aatacgattt aaatacagcg     660
cgaaatcctg aggatttaga tataaagctt gctaattatt ttccagtact aaaaattta     720 ataaacagac taaataatgc tcctgagaat aaattaccta ataatttggg taatattttt     780
gaatttagct ttgcaaaaga tagttcaact aatcaatatg taagtatcca gaaccaaatt     840

```
ccttcgctgt ttttaaaagc agatcttagt caaagtgccc gtgaaatttt agctagccca      900
gatgaagttc agccagttat taacatttta agattaatga aaaaagataa ttcttcttat      960
tttctaaatt ttgaggattt tgttaataat ttaacactga aaatatgca aaaagaagat     1020
ttaaatgcaa agggtcaaaa tcttctgcc tatgaatttc tagcagatat aaatctgga      1080
tttttccctg gagacaagag atccagtcat accaaggcag aaattagtaa tcttttaaat     1140
aaaaagaaa atatttatga ctttggtaaa tacaatggaa aattcaacga ccgtcttaac      1200
tcgccaaatt tagaatatag cctagatgca gcaagcgcaa gtcttgataa aaagataaa      1260
tcaatagttt taattcccta ccgccttgaa attaaagata aattttttgc cgatgattta     1320
tatccagata caaaagataa tattctcgta aagaaggga ttcttaaatt aactggattt      1380
aaaaaaggct caaaaattga tctccctaat atcaatcagc aaatttttaa aaccgaatat     1440
ttaccatttt ttgaaaaagg taagaagaa caagcaaaat tagactatgg taatatctta     1500
aatccatata atactcaact tgccaaagtt gaagttgaag ctcttttaa agggaataaa      1560
aaccaagaaa tctatcaagc acttgatgga aattatgcct atgaattcgg ggcctttaaa     1620
tccgtgctta attcctgaac aggaaaaat cagcatcctg aaaaagctga tatccaaaga      1680
tttacaagac atttagaaca agttaaaatt ggttctaatt cagttttaaa tcaaccacaa     1740
acaacaaaag aacaagtaat ttcaagtctt aaaagtaata actttttaa aaatggacat      1800
caagttgcaa gttatttcca ggatttactc accaaggaca aattaacaat tttagagact     1860
ctttatgatc tagcaaaaaa atggggacta gaaactaaca gagcacaatt cccaaagggg     1920
gttttccaat atacaaaaga tattttttgca gaagcagata aattaaaatt tttggaattg    1980
aagaaaaagg atccttacaa tcagataaaa gaaattcacc aactttcctt taatattttta   2040
gcccgtaacg atgtaataaa atctgatgga ttttacggag ttttattatt gccccaaagt    2100
gtaaaaactg aattagaagg caaaaatgag gcgcaaattt ttgaagcgct taaaaagtat     2160
tctttaattg agaactcggc ttttaaaact actattttag ataaaaattt acttgaaggg     2220
actgattta aaaccttcgg tgatttttta aaagcatttt tccttaaagc agcccaattt      2280
aataatttg ctccttgagc aaaattagac gataatcttc agtattcatt tgaagctatc     2340
aaaaaaggg aaactacaaa agaaggtaaa agagaagaag tagataaaaa agttaaggaa      2400
ttggataata aaataaaagg tatattgcct cagcccccag cagcaaaacc agaagcagca    2460
aaaccagtag cggctaaacc agaaacaaca aaaccagtag cagctaaacc tgaagcagct    2520
aaacctgaag cagcaaaacc agtagcggct aaaccagaag cagcaaaacc agtagcggct    2580
aaaccagaag cagcaaaacc agtagcggct aaaccagaag cagcaaaacc agtagcggct    2640
aaaccagaag cagcaaaacc agttgctact aatactggct tttcacttac aaataaacca    2700
aaagaagact atttcccaat ggcttttagt tataaattag aatatactga cgaaaataaa    2760
ttaagcctaa aaacaccgga aattaatgta tttttagaac tagttcatca aagcgagtat    2820
gaagaacaag aaataataaa ggaactagat aaaactgttt taaatcttca atatcaattc    2880
caggaagtca aggtaactag tgaccaatat cagaaactta gccacccaat gatgaccgaa     2940
ggatcttcaa atcaaggtaa aaaaagcgaa ggaactccta accaaggtaa aaaagcagaa    3000
ggcgcgccta accaaggtaa aaaagccgaa ggaactccta accaagggaa aaaagcagag   3060
ggagcaccta gtcaacaaag cccaactacc gaattaacta attaccttcc tgacttaggt    3120
aaaaaaattg acgaaatcat taaaaaacaa ggtaaaaatt gaaaaacaga ggttgaacta    3180
atcgaggata atatcgctgg agatgctaaa ttgctatact ttatcctaag ggatgattca    3240
```

```
aaatccggtg atcctaaaaa atcaagtcta aaagttaaaa taacagtaaa acaaagtaat    3300
aataatcagg aaccagaatc taaa                                           3324
```

<210> SEQ ID NO 4
<211> LENGTH: 1108
<212> TYPE: PRT
<213> ORGANISM: Mycoplasma hyopneumoniae

<400> SEQUENCE: 4

```
Met Ser Lys Lys Ser Lys Thr Phe Lys Ile Gly Leu Thr Ala Gly Ile
1               5                   10                  15

Val Gly Leu Gly Val Phe Gly Leu Thr Val Gly Leu Ser Ser Leu Ala
            20                  25                  30

Lys Tyr Arg Ser Glu Ser Pro Arg Lys Ile Ala Asn Asp Phe Ala Ala
        35                  40                  45

Lys Val Ser Thr Leu Ala Phe Ser Pro Tyr Ala Phe Glu Thr Asp Ser
    50                  55                  60

Asp Tyr Lys Ile Val Lys Arg Trp Leu Val Asp Ser Asn Asn Asn Ile
65                  70                  75                  80

Arg Asn Lys Glu Lys Val Ile Asp Ser Phe Ser Phe Phe Thr Lys Asn
                85                  90                  95

Gly Asp Gln Leu Glu Lys Ile Asn Phe Gln Asp Pro Glu Tyr Thr Lys
            100                 105                 110

Ala Lys Ile Thr Phe Glu Ile Leu Glu Ile Ile Pro Asp Asp Val Asn
        115                 120                 125

Gln Asn Phe Lys Val Lys Phe Gln Ala Leu Gln Lys Leu His Asn Gly
    130                 135                 140

Asp Ile Ala Lys Ser Asp Ile Tyr Glu Gln Thr Val Ala Phe Ala Lys
145                 150                 155                 160

Gln Ser Asn Leu Leu Val Ala Glu Phe Asn Phe Ser Leu Lys Lys Ile
                165                 170                 175

Thr Glu Lys Leu Asn Gln Gln Ile Glu Asn Leu Ser Thr Lys Ile Thr
            180                 185                 190

Asn Phe Ala Asp Glu Lys Thr Ser Ser Gln Lys Asp Pro Ser Thr Leu
        195                 200                 205

Arg Ala Ile Asp Phe Gln Tyr Asp Leu Asn Thr Ala Arg Asn Pro Glu
    210                 215                 220

Asp Leu Asp Ile Lys Leu Ala Asn Tyr Phe Pro Val Leu Lys Asn Leu
225                 230                 235                 240

Ile Asn Arg Leu Asn Asn Ala Pro Glu Asn Lys Leu Pro Asn Asn Leu
                245                 250                 255

Gly Asn Ile Phe Glu Phe Ser Phe Ala Lys Asp Ser Ser Thr Asn Gln
            260                 265                 270

Tyr Val Ser Ile Gln Asn Gln Ile Pro Ser Leu Phe Leu Lys Ala Asp
        275                 280                 285

Leu Ser Gln Ser Ala Arg Glu Ile Leu Ala Ser Pro Asp Glu Val Gln
    290                 295                 300

Pro Val Ile Asn Ile Leu Arg Leu Met Lys Lys Asp Asn Ser Ser Tyr
305                 310                 315                 320

Phe Leu Asn Phe Glu Asp Phe Val Asn Asn Leu Thr Leu Lys Asn Met
                325                 330                 335

Gln Lys Asp Leu Asn Ala Lys Gly Gln Asn Leu Ser Ala Tyr Glu
            340                 345                 350
```

-continued

```
Phe Leu Ala Asp Ile Lys Ser Gly Phe Pro Gly Asp Lys Arg Ser
            355                 360                 365

Ser His Thr Lys Ala Glu Ile Ser Asn Leu Leu Asn Lys Lys Glu Asn
        370                 375                 380

Ile Tyr Asp Phe Gly Lys Tyr Asn Gly Lys Phe Asn Asp Arg Leu Asn
385                 390                 395                 400

Ser Pro Asn Leu Glu Tyr Ser Leu Asp Ala Ser Ala Ser Leu Asp
                405                 410                 415

Lys Lys Asp Lys Ser Ile Val Leu Ile Pro Tyr Arg Leu Glu Ile Lys
            420                 425                 430

Asp Lys Phe Phe Ala Asp Asp Leu Tyr Pro Asp Thr Lys Asp Asn Ile
        435                 440                 445

Leu Val Lys Glu Gly Ile Leu Lys Leu Thr Gly Phe Lys Lys Gly Ser
            450                 455                 460

Lys Ile Asp Leu Pro Asn Ile Asn Gln Gln Ile Phe Lys Thr Glu Tyr
465                 470                 475                 480

Leu Pro Phe Phe Glu Lys Gly Lys Glu Gln Ala Lys Leu Asp Tyr
                485                 490                 495

Gly Asn Ile Leu Asn Pro Tyr Asn Thr Gln Leu Ala Lys Val Glu Val
                500                 505                 510

Glu Ala Leu Phe Lys Gly Asn Lys Asn Gln Glu Ile Tyr Gln Ala Leu
        515                 520                 525

Asp Gly Asn Tyr Ala Tyr Glu Phe Gly Ala Phe Lys Ser Val Leu Asn
    530                 535                 540

Ser Trp Thr Gly Lys Ile Gln His Pro Glu Lys Ala Asp Ile Gln Arg
545                 550                 555                 560

Phe Thr Arg His Leu Glu Gln Val Lys Ile Gly Ser Asn Ser Val Leu
                565                 570                 575

Asn Gln Pro Gln Thr Thr Lys Glu Gln Val Ile Ser Ser Leu Lys Ser
                580                 585                 590

Asn Asn Phe Phe Lys Asn Gly His Gln Val Ala Ser Tyr Phe Gln Asp
        595                 600                 605

Leu Leu Thr Lys Asp Lys Leu Thr Ile Leu Glu Thr Leu Tyr Asp Leu
    610                 615                 620

Ala Lys Lys Trp Gly Leu Glu Thr Asn Arg Ala Gln Phe Pro Lys Gly
625                 630                 635                 640

Val Phe Gln Tyr Thr Lys Asp Ile Phe Ala Glu Ala Asp Lys Leu Lys
                645                 650                 655

Phe Leu Glu Leu Lys Lys Lys Asp Pro Tyr Asn Gln Ile Lys Glu Ile
            660                 665                 670

His Gln Leu Ser Phe Asn Ile Leu Ala Arg Asn Asp Val Ile Lys Ser
        675                 680                 685

Asp Gly Phe Tyr Gly Val Leu Leu Pro Gln Ser Val Lys Thr Glu
    690                 695                 700

Leu Glu Gly Lys Asn Glu Ala Gln Ile Phe Glu Ala Leu Lys Lys Tyr
705                 710                 715                 720

Ser Leu Ile Glu Asn Ser Ala Phe Lys Thr Thr Ile Leu Asp Lys Asn
                725                 730                 735

Leu Leu Glu Gly Thr Asp Phe Lys Thr Phe Gly Asp Phe Leu Lys Ala
            740                 745                 750

Phe Phe Leu Lys Ala Ala Gln Phe Asn Asn Phe Ala Pro Trp Ala Lys
        755                 760                 765

Leu Asp Asp Asn Leu Gln Tyr Ser Phe Glu Ala Ile Lys Lys Gly Glu
```

| | | | | | | | | | | | | |
|---|---|---|---|---|---|---|---|---|---|---|---|---|
| | | 770 | | | 775 | | | 780 | | | | |

Thr Thr Lys Glu Gly Lys Arg Glu Val Asp Lys Val Lys Glu
785             790             795             800

Leu Asp Asn Lys Ile Lys Gly Ile Leu Pro Gln Pro Ala Ala Lys
            805             810             815

Pro Glu Ala Ala Lys Pro Val Ala Ala Lys Pro Glu Thr Thr Lys Pro
                820             825             830

Val Ala Ala Lys Pro Glu Ala Ala Lys Pro Glu Ala Ala Lys Pro Val
            835             840             845

Ala Ala Lys Pro Glu Ala Ala Lys Pro Val Ala Ala Lys Pro Glu Ala
850             855             860

Ala Lys Pro Val Ala Ala Lys Pro Glu Ala Ala Lys Pro Val Ala Ala
865             870             875             880

Lys Pro Glu Ala Ala Lys Pro Val Ala Thr Asn Thr Gly Phe Ser Leu
                885             890             895

Thr Asn Lys Pro Lys Glu Asp Tyr Phe Pro Met Ala Phe Ser Tyr Lys
            900             905             910

Leu Glu Tyr Thr Asp Glu Asn Lys Leu Ser Leu Lys Thr Pro Glu Ile
            915             920             925

Asn Val Phe Leu Glu Leu Val His Gln Ser Glu Tyr Glu Glu Gln Glu
930             935             940

Ile Ile Lys Glu Leu Asp Lys Thr Val Leu Asn Leu Gln Tyr Gln Phe
945             950             955             960

Gln Glu Val Lys Val Thr Ser Asp Gln Tyr Gln Lys Leu Ser His Pro
                965             970             975

Met Met Thr Glu Gly Ser Ser Asn Gln Gly Lys Lys Ser Glu Gly Thr
            980             985             990

Pro Asn Gln Gly Lys Lys Ala Glu Gly Ala Pro Asn Gln Gly Lys Lys
            995             1000             1005

Ala Glu Gly Thr Pro Asn Gln Gly Lys Lys Ala Glu Gly Ala Pro
    1010             1015             1020

Ser Gln Gln Ser Pro Thr Thr Glu Leu Thr Asn Tyr Leu Pro Asp
    1025             1030             1035

Leu Gly Lys Lys Ile Asp Glu Ile Ile Lys Lys Gln Gly Lys Asn
    1040             1045             1050

Trp Lys Thr Glu Val Glu Leu Ile Glu Asp Asn Ile Ala Gly Asp
    1055             1060             1065

Ala Lys Leu Leu Tyr Phe Ile Leu Arg Asp Asp Ser Lys Ser Gly
    1070             1075             1080

Asp Pro Lys Lys Ser Ser Leu Lys Val Lys Ile Thr Val Lys Gln
    1085             1090             1095

Ser Asn Asn Asn Gln Glu Pro Glu Ser Lys
    1100             1105

<210> SEQ ID NO 5
<211> LENGTH: 1773
<212> TYPE: DNA
<213> ORGANISM: Porcine circovirus

<400> SEQUENCE: 5
ggtacctccg tggattgttc tccagcagtc ttccaaaatt gcaaagtagt aatcctccga      60
tagagagctt ctacagctgg gacagcagtt gaggagtacc attcctgggg ggcctgattg     120
ctggtaatca aaatactgcg ggccaaaaaa ggaacagtac ccccctttagt ctctacagtc    180

-continued

```
aatggatacc ggtcacacag tctcagtaga tcatcccaag gtaaccagcc ataaaaatca    240
tccaaaacaa caacttcttc tccatgatat ccatcccacc acttatttct actaggcttc    300
cagtaggtgt ccctaggctc agcaaaatta cgggcccact ggctcttccc acaaccgggc    360
gggcccacta tgacgtgtac agctgtcttc caatcacgct gctgcatctt cccgctcact    420
ttcaaaagtt cagccagccc gcggaaattt ctcacatacg ttacaggaaa ctgctcggct    480
acagtcacca aagaccccgt ctccaaaagg gtactcacag cagtagacag gtcgctgcgc    540
ttcccctggt tccgcggagc tccacactcg ataagtatgt ggccttcttt actgcagtat    600
tctttattct gctggtcggt tcctttcgct ttctcgatgt ggcagcgggc accaaaatac    660
cacttcacct tgttaaaagt ctgcttctta gcaaaattcg caaacccctg gaggtgagga    720
gttctaccct cttccaaacc ttcctcgcca caaacaaaat aatcaaaaag ggagattgga    780
agctcccgta ttttgttttt ctcctcctcg gaaggattat taagggtgaa cacccacctc    840
ttatggggtt gcgggccgct ttcttgcttg gcattttca ctgacgctgc cgaggtgctg    900
ccgctgccga agtgcgctgg taatactaca gcagcgcact tctttcactt ttataggatg    960
acgtatccaa ggaggcgtta ccgcagaaga agacaccgcc cccgcagcca tcttggccag   1020
atcctccgcc gccgcccctg gctcgtccac ccccgccacc gctaccgttg gagaaggaaa   1080
aatggcatct tcaacacccg cctctcccgc accttcggat atactgtcaa ggctaccaca   1140
gtcagaacgc cctcctgggc ggtggacatg atgagattta atattgacga ctttgttccc   1200
ccgggagggg ggaccaacaa aatctctata ccctttgaat actacagaat aagaaaggtt   1260
aaggttgaat tctggccctg ctccccccatc acccagggtg ataggggagt gggctccact   1320
gctgttattc tagatgataa ctttgtaaca aaggccacag ccctaaccta tgacccatat   1380
gtaaactact cctcccgcca tacaatcccc caacccttct cctaccactc ccgttacttc   1440
acacccaaac ctgttcttga ctccaccatt gattacttcc aaccaaataa caaaaggaat   1500
cagctttgga tgaggctaca aacctctaga aatgtggacc acgtaggcct cggcactgcg   1560
ttcgaaaaca gtatatacga ccaggactac aatatccgtg taaccatgta tgtacaattc   1620
agagaattta atcttaaaga ccccccactt aaaccctaaa tgaataaaaa taaaaaccat   1680
tacgatgtga taacaaaaaa gactcagtaa tttattttat atgggaaaag ggcacagggt   1740
gggtccactg cttcaaatcg gccttcgggt acc                                1773
```

<210> SEQ ID NO 6
<211> LENGTH: 702
<212> TYPE: DNA
<213> ORGANISM: Porcine circovirus

<400> SEQUENCE: 6

```
atgacgtatc caaggaggcg ttaccgcaga agaagacacc gcccccgcag ccatcttggc     60
cagatcctcc gccgccgccc ctggctcgtc cacccccgcc accgctaccg ttggagaagg    120
aaaaatggca tcttcaacac ccgcctctcc cgcaccttcg gatatactgt caaggctacc    180
acagtcagaa cgccctcctg ggcggtggac atgatgagat ttaatattga cgactttgtt    240
cccccgggag gggggaccaa caaaatctct ataccctttg aatactacag aataagaaag    300
gttaaggttg aattctggcc ctgctccccc atcacccagg gtgatagggg agtgggctcc    360
actgctgtta ttctagatga taactttgta acaaaggcca cagccctaac ctatgaccca    420
tatgtaaact actcctcccg ccatacaatc cccaaccct tctcctacca ctcccgttac    480
ttcacaccca aacctgttct tgactccacc attgattact tccaaccaaa taacaaaagg    540
```

```
aatcagcttt ggatgaggct acaaacctct agaaatgtgg accacgtagg cctcggcact    600
gcgttcgaaa acagtatata cgaccaggac tacaatatcc gtgtaaccat gtatgtacaa    660
ttcagagaat taatcttaa agacccccca cttaaaccct aa                        702
```

```
<210> SEQ ID NO 7
<211> LENGTH: 233
<212> TYPE: PRT
<213> ORGANISM: Porcine circovirus

<400> SEQUENCE: 7
```

Met Thr Tyr Pro Arg Arg Arg Tyr Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Phe Gly Tyr Thr Val Lys Ala Thr Thr Val Arg Thr
    50                  55                  60

Pro Ser Trp Ala Val Asp Met Met Arg Phe Asn Ile Asp Asp Phe Val
65                  70                  75                  80

Pro Pro Gly Gly Gly Thr Asn Lys Ile Ser Ile Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Thr Ala Leu Thr Tyr Asp Pro Tyr Val Asn Tyr
    130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Met Arg Leu Gln Thr Ser Arg Asn
            180                 185                 190

Val Asp His Val Gly Leu Gly Thr Ala Phe Glu Asn Ser Ile Tyr Asp
        195                 200                 205

Gln Asp Tyr Asn Ile Arg Val Thr Met Tyr Val Gln Phe Arg Glu Phe
    210                 215                 220

Asn Leu Lys Asp Pro Pro Leu Lys Pro
225                 230

```
<210> SEQ ID NO 8
<211> LENGTH: 1767
<212> TYPE: DNA
<213> ORGANISM: Porcine circovirus

<400> SEQUENCE: 8
ggtacctccg tggattgttc tccagcagtc ttccaaaatt gcaaagtagt aatcctccga    60
tagagagctt ctacagctgg gacagcagtt gaggagtacc attcctgggg ggcctgattg    120
ctggtaatca aaatactgcg ggccaaaaaa ggaacagtac ccccctttagt ctctacagtc    180 aatggatacc ggtcacacag tctcagtaga tcatcccaag gtaaccagcc ataaaaatca    240
tccaaaacaa caacttcttc tccatgatat ccatcccacc acttattttct actaggcttc    300 cagtaggtgt cgctaggctc agcaaaatta cgggcccact ggctcttccc acaaccgggc    360
```

```
gggcccacta tgacgtgtac agctgtcttc caatcacgct gctgcatctt cccgctcact    420
ttcaaaagtt cagccagccc gcggaaattt ctcacatacg ttacagggaa ctgctcggct    480
acagtcacca agaccccgt ctccaaaagg gtactcacag cagtagacag gtcgctgcgc    540
ttcccctggt tccgcggagc tccacactcg ataagtatgt ggccttcttt actgcagtat    600
tctttattct gctggtcggt tcctttcgct ttctcgatgt ggcagcgggc accaaaatac    660
cacttcacct tgttaaaagt ctgcttctta gcaaaattcg caaaccctg gaggtgagga    720 gttctaccct cttccaaacc ttcctctccg caaacaaaat aatcaaaaag ggagattgga    780
agctcccgta ttttgttttt ctcctcctcg aaggattat taagggtgaa cacccacctc    840
ttatggggtt gcgggccgct tttcctgctt ggcattttca ctgacgctgc cgaggtgctg    900
ccgctgccga gtgcgctgg taatactaca gcagcgcact tctttcactt ttataggatg    960
acgtatccaa ggaggcgtta ccgcagaaga agacaccgcc cccgcagcca tcttggccag    1020
atcctccgcc gccgccctg gctcgtccac cccgccacc gctaccgttg gagaaggaaa    1080
aatggcatct tcaacacccg cctctcccgc accttcggat atactgtcaa ggctaccaca    1140
gtcagaacgc cctcctgggc ggtggacatg atgagattta atattgacga ctttgttccc    1200
ccgggagggg ggaccaacaa aatctctata cccttgaat actacagaat aagaaaggtt    1260
aaggttgaat tctggccctg ctccccatc acccagggtg ataggggagt gggctccact    1320
gctgttattc tagatgataa cttgtaaca aaggccacag ccctaaccta tgacccatat    1380
gtaaactact cctcccgcca tacaatcgcc caacccttct cctaccactc ccgttacttc    1440
acacccaaac ctgttcttga ctccaccatt gattacttcc aaccaaataa caaaaggaat    1500
cagctttgga tgaggctaca aacctctaga aatgtggacc acgtaggcct cggcactgcg    1560
ttcgaaaaca gtatatacga ccaggactac aatatccgtg taaccatgta tgtacaattc    1620
agagaattta atcttaaaga cccccccactt aaacccctaaa tgaataaaaa taaaaaccat    1680
tacgatgtga taacaaaaaaa gactcagtaa ttatttttat atgggaaaag ggcacagggt    1740
gggtccactg cttcaaatcg gccttcg    1767
```

<210> SEQ ID NO 9
<211> LENGTH: 702
<212> TYPE: DNA
<213> ORGANISM: Porcine circovirus

<400> SEQUENCE: 9

```
atgacgtatc caaggaggcg ttaccgcaga agaagacacc gccccccgcag ccatcttggc    60 cagatcctcc gccgccgccc ctggctcgtc caccccgcc accgctaccg ttggagaagg    120
aaaaatggca tcttcaacac ccgcctctcc cgcaccttcg gatatactgt caaggctacc    180
acagtcagaa cgccctcctg ggcggtggac atgatgagat ttaatattga cgactttgtt    240
cccccgggag gggggaccaa caaaatctct atacccttg aatactacag aataagaaag    300
gttaaggttg aattctggcc ctgctccccc atcacccagg gtgataggg agtgggctcc    360 actgctgtta ttctagatga taactttgta caaaggcca cagccctaac ctatgaccca    420
tatgtaaact actcctcccg ccatacaatc gcccaacccct tctcctacca ctcccgttac    480
ttcacaccca aacctgttct tgactccacc attgattact tccaaccaaa taacaaaagg    540
aatcagcttt ggatgaggct acaaacctct agaaatgtgg accacgtagg cctcggcact    600
gcgttcgaaa acagtatata cgaccaggac tacaatatcc gtgtaaccat gtatgtacaa    660
```
ttcagagaat ttaatcttaa agacccccca cttaaaccct aa                                702

<210> SEQ ID NO 10
<211> LENGTH: 233
<212> TYPE: PRT
<213> ORGANISM: Porcine circovirus

<400> SEQUENCE: 10

```
Met Thr Tyr Pro Arg Arg Arg Tyr Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Phe Gly Tyr Thr Val Lys Ala Thr Thr Val Arg Thr
    50                  55                  60

Pro Ser Trp Ala Val Asp Met Met Arg Phe Asn Ile Asp Asp Phe Val
65                  70                  75                  80

Pro Pro Gly Gly Gly Thr Asn Lys Ile Ser Ile Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Thr Ala Leu Thr Tyr Asp Pro Tyr Val Asn Tyr
    130                 135                 140

Ser Ser Arg His Thr Ile Ala Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Met Arg Leu Gln Thr Ser Arg Asn
            180                 185                 190

Val Asp His Val Gly Leu Gly Thr Ala Phe Glu Asn Ser Ile Tyr Asp
        195                 200                 205

Gln Asp Tyr Asn Ile Arg Val Thr Met Tyr Val Gln Phe Arg Glu Phe
    210                 215                 220

Asn Leu Lys Asp Pro Pro Leu Lys Pro
225                 230
```

<210> SEQ ID NO 11
<211> LENGTH: 233
<212> TYPE: PRT
<213> ORGANISM: Porcine circovirus

<400> SEQUENCE: 11

```
Met Thr Tyr Pro Arg Arg Arg Tyr Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Phe Gly Tyr Thr Val Lys Ala Thr Thr Val Thr Thr
    50                  55                  60

Pro Ser Trp Ala Val Asp Met Met Arg Phe Asn Ile Asp Asp Phe Val
65                  70                  75                  80

Pro Pro Gly Gly Gly Thr Asn Lys Ile Ser Ile Pro Phe Glu Tyr Tyr
```

```
                85                  90                  95
Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Thr Ala Leu Thr Tyr Asp Pro Tyr Val Asn Tyr
130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Leu Arg Leu Gln Thr Ser Arg Asn
            180                 185                 190

Val Asp His Val Gly Leu Gly Thr Ala Phe Glu Asn Ser Lys Tyr Asp
        195                 200                 205

Gln Asp Tyr Asn Ile Arg Val Thr Met Tyr Val Gln Phe Arg Glu Phe
210                 215                 220

Asn Leu Lys Asp Pro Pro Leu Lys Pro
225                 230
```

<210> SEQ ID NO 12
<211> LENGTH: 713
<212> TYPE: DNA
<213> ORGANISM: Porcine circovirus

<400> SEQUENCE: 12

```
cagctatgac gtatccaagg aggcgttacc gcagaagaag acaccgcccc cgcagccatc     60
ttggccagat cctccgccgc cgcccctggc tcgtccaccc ccgccaccgc taccgttgga    120
gaaggaaaaa tggcatcttc aacacccgcc tctcccgcac cttcggatat actgtggaga    180
aggaaaaatg gcatcttcaa cacccgcctc tcccgcacct tcggatatac tgtgacgact    240
tgttccccc gggagggggg accaacaaaa tctctatacc ctttgaatac tacagaataa    300
gaaaggttaa ggttgaattc tggccctgct ccccatcac caggtgat aggggagtgg    360
gctccactgc tgttattcta gatgataact ttgtaacaaa ggccacagcc ctaacctatg    420
acccatatgt aaactactcc tcccgccata caatccccca acccttctcc taccactccc    480
gttacttcac acccaaacct gttcttgact ccactattga ttacttccaa ccaataaca    540
aaaggaatca gctttggctg aggctacaaa cctctagaaa tgtggaccac gtaggcctcg    600
gcactgcgtt cgaaaacagt aaatacgacc aggactacaa tatccgtgta accatgtatg    660
tacaattcag agaatttaat cttaaagacc ccccacttaa accctaaatg aat           713
```

<210> SEQ ID NO 13
<211> LENGTH: 233
<212> TYPE: PRT
<213> ORGANISM: Porcine circovirus

<400> SEQUENCE: 13

```
Met Thr Tyr Pro Arg Arg Arg Tyr Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Phe Gly Tyr Thr Val Lys Ala Thr Thr Val Thr Thr
```

```
                  50                  55                  60
Pro Ser Trp Ala Val Asp Met Met Arg Phe Asn Ile Asp Asp Phe Val
 65                  70                  75                  80

Pro Pro Gly Gly Gly Thr Asn Lys Ile Ser Ile Pro Phe Glu Tyr Tyr
                 85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Thr Ala Leu Thr Tyr Asp Pro Tyr Val Asn Tyr
    130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Leu Arg Leu Gln Thr Ser Arg Asn
            180                 185                 190

Val Asp His Val Gly Leu Gly Thr Ala Phe Glu Asn Ser Lys Tyr Asp
        195                 200                 205

Gln Asp Tyr Asn Ile Arg Val Thr Met Tyr Val Gln Phe Arg Glu Phe
    210                 215                 220

Asn Leu Lys Asp Pro Pro Leu Glu Pro
225                 230

<210> SEQ ID NO 14
<211> LENGTH: 713
<212> TYPE: DNA
<213> ORGANISM: Porcine circovirus

<400> SEQUENCE: 14
ccgccatgac gtatccaagg aggcgttacc gcagaagaag acaccgcccc cgcagccatc    60
ttggccagat cctccgccgc cgcccctggc tcgtccaccc ccgccaccgc taccgttgga   120
gaaggaaaaa tggcatcttc aacacccgcc tctcccgcac cttcggatat actgtcaagg   180
ctaccacagt cacaacgccc tcctgggcgg tggacatgat gagatttaat attgacgact   240
tgttcccccc ggggaggggg accaacaaaa tctctatacc ctttgaatac tacagaataa   300
gaaaggttaa ggttgaattc tggccctgct cccccatcac ccagggtgat aggggagtgg   360
gctccactgc tgttattcta gatgataact ttgtaacaaa ggccacagcc ctaacctatg   420
acccatatgt aaactactcc tcccgccata caatccccca cccttctccc taccactccc   480
gttacttcac acccaaacct gttcttgact ccactattga ttacttccaa ccaaataaca   540
aaaggaatca gctttggctg aggctacaaa cctctagaaa tgtggaccac gtaggcctcg   600
gcactgcgtt cgaaaacagt aaatacgacc aggactacaa tatccgtgta accatgtatg   660
tacaattcag agaatttaat cttaaagacc ccccacttga accctaagaa ttc          713

<210> SEQ ID NO 15
<211> LENGTH: 233
<212> TYPE: PRT
<213> ORGANISM: Porcine circovirus

<400> SEQUENCE: 15

Met Thr Tyr Pro Arg Arg Arg Tyr Arg Arg Arg His Arg Pro Arg
  1               5                  10                  15

Ser His Leu Gly Gln Ile Leu Arg Arg Arg Pro Trp Leu Val His Pro
```

```
                 20                  25                  30
Arg His Arg Tyr Arg Trp Arg Arg Lys Asn Gly Ile Phe Asn Thr Arg
            35                  40                  45

Leu Ser Arg Thr Phe Gly Tyr Thr Val Lys Ala Thr Thr Val Arg Thr
 50                  55                  60

Pro Ser Trp Ala Val Asp Met Met Arg Phe Asn Ile Asp Asp Phe Val
 65                  70                  75                  80

Pro Pro Gly Gly Gly Thr Asn Lys Ile Ser Ile Pro Phe Glu Tyr Tyr
                85                  90                  95

Arg Ile Lys Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
            115                 120                 125

Phe Val Thr Lys Ala Thr Ala Leu Thr Tyr Asp Pro Tyr Val Asn Tyr
            130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Ser Thr Ile Asp Tyr Phe Gln Pro
            165                 170                 175

Asn Asn Lys Arg Asn Gln Leu Trp Leu Arg Leu Gln Thr Ser Arg Asn
            180                 185                 190

Val Asp His Val Gly Leu Gly Thr Ala Phe Glu Asn Ser Ile Tyr Asp
            195                 200                 205

Gln Asp Tyr Asn Ile Arg Val Thr Met Tyr Val Gln Phe Arg Glu Phe
            210                 215                 220

Asn Leu Lys Asp Pro Pro Leu Lys Pro
225                 230

<210> SEQ ID NO 16
<211> LENGTH: 15450
<212> TYPE: DNA
<213> ORGANISM: Porcine reproductive and respiratory syndrome virus

<400> SEQUENCE: 16
atgacgtata ggtgttggct ctatgccacg gcatttgtat tgtcaggagc tgtggccatt      60
ggcacagccc aaaacttgct gcacggaaaa cgcccttctg tgacagcctt cttcagggga     120
gcttaggggt ctgtccctag caccttgctt ctggagttgc actgctttac ggtctctcca     180
ccccttcaac catgtctggg atacttgatc ggtgcacgtg cacccccaat gccagggtgt     240
ttatggcgga gggccaagtc tactgcacac gatgtctcag tgcacggtct ctccttcctc     300
tgaatctcca agttcctgag cttggggtgc tgggcctatt ttataggccc gaagagccac     360
tccggtggac gttgccacgt gcattcccca ctgtcgagtg ctcccctgcc ggggcctgct     420
ggctttctgc gatctttcca attgcacgaa tgaccagtgg aaacctgaac tttcaacaaa     480
gaatggtgcg gttgcagct  gagatttaca gagccggcca actcacccct gcagttttga     540
aggctctaca agtttatgaa cggggttgtc gctggtaccc cattgtcgga cctgtccctg     600
gagtggccgt ttacgccaac tccctacatg tgagtgacaa ccttttcccg ggagcaactc     660
atgtgttaac caacctaccg ctcccgcaga ggcccaagcc tgaagacttt gcccttttg      720 agtgtgctat ggctaacgtc tatgacattg ccataacgc cgtcatgtat gtggccagag     780
ggaaagtctc ctgggcccct cgtggcgggg atgaagtgaa atttgaaacc gtccccgaag     840
agttgaagtt gattgcgaac cgactccaca tctccttccc gccccaccac gcagtggaca     900
```

```
tgtctgagtt tgccttcata gcccctggga gtggtgtctc cttgcgggtc gagcaccaac    960
acggctgcct tcccgctgat actgtccctg atgggaactg ctggtggtac ttgtttgact   1020
tgctcccacc ggaagttcag aataaagaaa ttcgccgtgc taaccaattt ggctatcaaa   1080
ccaagcatgg tgtccatggc aagtacctac agcggaggct gcaagttaat ggtctccgag   1140
cagtgactga tacagatgga cctattgtcg tacagtactt ctctgttagg gagagttgga   1200
tccgccactt cagactggcg gaagaaccta gcctccctgg gtttgaagac ctcctcagaa   1260
taagggtaga gcctaatacg tcgccaatgg gtggcaaggg tgaaaaaatc ttccggtttg   1320
gcagtcacaa gtggtacggt gctggaaaga gagcaaggag agcacgctct ggtgcgactg   1380
ccacggtcgc tcaccgcgct tgcccgctc gcgaagccca gcaggccaag aagctcgagg   1440
ttgccagcgc caacagggct gagcatctca agtactattc cccgcctgcc gacgggaact   1500
gtggttggca ctgcatttcc gccattacca accggatggt gaattccaaa tttgaaacca   1560
ctcttcccga gagagtgaga ccttcagatg actgggctac tgacgaggat cttgtgaata   1620
ccatccaaat cctcaggctc cccgcggcct tggacaggaa cggtgcttgt gctggcgcca   1680
agtacgtgct caagctggaa ggtgagcact ggaccgtctc tgtgaccct gggatgaccc    1740 cttctttgct cccccttgaa tgtgttcagg ttgttgtga gcataagagc ggtcttggtt   1800
tcccagacgt ggtcgaagtt tccggatttg accctgcctg tcttgaccga cttgctgaga   1860
taatgcactt gcctagcagt gtcatcccag ctgctctggc cgagatgtcc gacgacttca   1920
atcgtctggc ttccccggcc gccactgtgt ggactgtttc gcaattcttt gcccgccaca   1980
gaggaggaga gcatcctgac caggtgtgct tagggaaaat tatcaaccct tgtcaggtga   2040
ttgaggaatg ctgctgttcc cggaacaaag ccaaccgggc taccccggaa gaggttgcgg   2100
caaaagttga ccagtacctc cgtggtgcag caagccttgg agaatgcttg ccaagcttg    2160 agagggctcg cccgccgagc gcgacggaca cctcctttga ttggaatgtt gtgcttcctg   2220
gggttgagac ggcgaatcag acaaccaaac agctccatgt caaccagtgc cgcgctctgg   2280
ttcctgtcgt gactcaagag ccttttggaca gagactcggt ccctctgacc gccttctcgc   2340
tgtccaattg ctactaccct gcacaaggtg acgaggtccg tcaccgtgag aggctaaact    2400
ccttgctctc taagttggag ggggttgttc gtgaggaata tgggctcacg ccaactggac   2460
ctggcccgcg acccgcactg ccgaacgggc tcgacgagct taaagaccag atggaggagg   2520
atctgctgaa attagtcaac gcccaggcaa cttcagaaat gatggcctgg gcagccgagc   2580
aggttgatct aaaagcttgg gtcaaaaatt acccacggtg gacaccgcca cccctccac    2640 caagagttca gcctcgaaaa acgaagtctg tcaagagctt gctagagaac aagcctgtcc   2700
ctgctccgcg caggaaggtc agatctgatt gtggcagccc gatttgatg ggcgacaatg    2760 ttcctaacgg ttgggaagat tcgactgttg gtggtccct tgatcttcg gcaccatccg     2820 agccgatgac acctctgagt gagcctgtac ttatttccag gccagtgaca tctttgagtg   2880
tgccggcccc agttcctgca ccgcgtagag ctgtgtcccg accgatgacg ccctcgagtg   2940
agccaatttt tgtgtctgca ctgcgacaca aatttcagca ggtggaaaaa gcaaatctgg   3000
cggcagcagc gccgatgtgc caggacgaac ccttagattt gtctgcatcc tcacagactg   3060
aatatgaggc ttccccccta acaccaccgc agaacgtggg cattctggag gtaagggggc   3120
aagaagctga ggaagttctg agtgaaatct cggatattct gaatgatacc aaccctgcac   3180
ctgtgtcatc aagcagctcc ctgtcaagtg ttaagatcac acgcccaaaa tactcagctc   3240
aagccattat cgactcgggc gggccctgca gtgggcacct ccaaagggaa aaagaagcat   3300
```

```
gcctccgcat catgcgtgaa gcttgtgatg cggccaagct tagtgaccct gccacgcagg   3360
aatggctttc tcgcatgtgg gatagggtgg acatgctgac ttggcgcaac acgtctgctt   3420
accaggcgtt tcgcacccta gatggcaggt ttgggtttct cccaaagatg atactcgaga   3480
cgccgccgcc ctaccgtgt  gggtttgtga tgttgcctca caccctgca  ccttccgtga   3540
gtgcagagag cgaccttacc attggttcag tcgccactga agatattcca cgcatcctcg   3600
ggaaaataga aaataccggt gagatgatca accaggacc  cttggcatcc tctgaggaag   3660
aaccggtata caaccaacct gccaaagact cccggatatc gtcgcggggg tctgacgaga   3720
gcacagcagc tccgtccgcg gtacaggtg  cgccggctt  atttactgat ttgccacctt   3780
cagacggcgt agatgcggac ggtgggggc  cgttgcagac ggtaagaaag aaagctgaaa   3840
ggctcttcga ccaattgagc cgtcaggttt ttaacctcgt ctcccatctc cctgttttct   3900
tctcacacct cttcaaatct gacagtggtt attctccggg tgattggggt tttgcagctt   3960
ttactctatt ttgcctcttt ttgtgttaca gctacccatt cttcggtttc gttccctct    4020
tgggtgtatt ttctgggtct tctcggcgtg tgcgcatggg ggttttggc  tgctggctgg   4080
cttttgctgt tggcctgttc aagcctgtgt ccgacccagt cggcactgct tgtgagtttg   4140
actcgccaga gtgcaggaac gtccttcatt cttttgagct tctcaaacct tgggaccctg   4200
ttcgcagcct tgttgtgggc cccgtcggtc tcggtcttgc cattcttggc aagttactgg   4260
gcggggcacg ctacatctgg catttttgc  ttaggcttgg cattgttgca gattgtatct   4320
tggctggagc ttatgtgctt tctcaaggta ggtgtaaaaa gtgctgggga tcttgtataa   4380
gaactgctcc taatgaaatc gccttcaacg tgttcccttt tacacgtgcg accaggtcgt   4440
cactcatcga cctgtgcgat cggttttgtg cgccaacagg catggacccc attttcctcg   4500
ccactgggtg gcgtgggtgc tggaccggcc gaagtcccat tgagcaaccc tctgaaaaac   4560
ccatcgcgtt cgcccagttg gatgaaaaga ggattacggc tagaactgtg gtcgctcagc   4620
cttatgatcc taatcaagcc gtgaagtgct tgcgggtgtt acaggcgggt ggggcgatgg   4680
tggccgaggc agtcccaaaa gtggccaaag tttctgctat tccattccga gcccctttt   4740
ttcccaccgg agtgaaagtt gatcccgagt gcaggatcgt ggttgacccc gatactttta   4800
ctacagccct ccggtctggt tactctacca caaacctcgt ccttggtgtg gggactttg    4860
cccagctgaa tggactaaag atcaggcaaa tttccaagcc ttcgggagga ggcccacacc   4920
tcattgctgc cctgcatgtt gcctgctcga tggcgttgca catgcttgct ggggtttatg   4980
taacttcagt ggggtcttgc ggtgccggca ccaacgatcc atggtgcact aatccgtttg   5040
ccgttcctgg ctacggacca ggctctctct gcacgtccag attgtgcatc tcccaacatg   5100
gccttaccct gcccttgaca gcacttgtgg cgggattcgg tcttcaggaa atcgccttgg   5160
tcgttttgat tttcgtttcc atcggaggca tggctcatag gttgagttgt aaggctgata   5220
tgctgtgcat tttacttgca atcgccagct atgtttgggt accccttacc tggttgcttt   5280
gtgtgtttcc ttgttggttg cgctggttct ctttgcaccc ccttaccatc ctatggttgg   5340
tgttttctt  gatttctgta aatatgcctt cgggaatctt ggccgtggtg ttattggttt   5400
ctctttggct tttgggacgt tatactaaca ttgctgtct  tgtcaccccc tatgatattc   5460
atcattacac cagtggcccc cgcggtgttg ccgccttggc taccgcacca gatggaacct   5520
acttggctgc cgtccgccgc gctgcgttga ctggtcgcac catgctgttc accccgtctc   5580
agcttgggtc ccttcttgag ggcgctttca gaactcgaaa gccctcactg aacaccgtca   5640
```

```
atgtggttgg gtcctccatg ggctctggtg gagtgttcac catcgacggg aaaattaggt    5700
gcgtgactgc cgcacatgtc cttacgggta attcggctag ggtttccgga gtcggcttca    5760
atcaaatgct tgactttgat gtgaaagggg acttcgccat agctgattgc ccgaattggc    5820
aaggagctgc tcccaagacc caattctgcg aggacggatg gactgccgt gcctattggc     5880
tgacatcctc tggcgtcgaa cccggtgtta ttgggaatgg attcgccttc tgcttcaccg    5940
cgtgcggcga ttccgggtcc ccagtgatca ccgaagctgg tgagattgtc ggcgttcaca    6000
caggatcaaa taaacaagga ggtggcatcg tcacgcgccc ttcaggccag ttttgtaacg    6060
tggcacccat caagctgagc gaattaagtg aattctttgc tggacccaag gtcccgctcg    6120
gtgatgtgaa ggttggcagc cacataatta agacacgtg cgaagtacct tcagatcttt     6180
gcgccttgct tgctgccaaa cctgaactgg agggaggcct ctccaccgtc caacttctgt    6240
gtgtgttttt cctactgtgg agaatgatgg gacatgcctg gacgcccttg gttgctgtgg    6300
ggttttcat tctgaatgag gttctcccag ctgtcctggt tcggagtgtt ttctcctttg     6360
ggatgttgt gctatcttgg ctcacaccat ggtctgcgca agttctgatg atcaggcttc     6420
taacagcagc tcttaacagg aacagatggt cacttgcctt ttacagcctt ggtgcggtga    6480
ccggttttgt cgcagatctt gcggtaactc aagggcaccc gttgcaggca gtaatgaatt    6540
tgagcaccta tgccttcctg cctcggatga tggttgtgac ctcaccagtc ccagtgattg    6600
cgtgtggtgt tgtgcaccta cttgccatca ttttgtactt gttcaagtac cgcggcctgc    6660
acaatgttct tgttggtgat ggagcgtttt ctgcagcttt cttcttgcga tactttgccg    6720
agggaaagtt gagggaaggg gtgtcgcaat cctgcggaat gaatcatgag tcattgactg    6780
gtgccctcgc tatgagactc aatgacgagg acttggactt ccttacgaaa tggactgatt    6840
ttaagtgctt tgtttctgcg tccaacatga ggaatgcagc aggccaattc atcgaggctg    6900
cctatgcaaa agcacttaga attgaacttg cccagttggt gcaggttgat aaggttcgag    6960
gtactttggc caagcttgag gcttttgctg ataccgtggc accccaactc tcgcccggtg    7020
acattgttgt tgctcttggc catacgcctg ttggcagcat cttcgaccta aaggttggtg    7080
gtaccaagca tactctccaa gtcattgaga ccagagtcct tgccgggtcc aaaatgaccg    7140
tggcgcgcgt cgttgaccca accccacgc ccccacccgc acccgtgccc atcccctcc      7200
caccgaaagt tctagagaat ggtcccaacg cctggggga tggggaccgt ttgaataaga     7260
agaagaggcg taggatggaa accgtcggca tctttgtcat gggtgggaag aagtaccaga    7320
aattttggga caagaattcc ggtgatgtgt tttacgagga ggtccatgac aacacagatg    7380
cgtgggagtg cctcagagtt ggtgaccctg ccgactttaa ccctgagaag ggaactctgt    7440
gtgggcatac tactattgaa gataaggatt acaaagtcta cgcctcccca tctggcaaga    7500
agttcctggt ccccgtcaac ccagagagcg gaagagccca atgggaagct gcaaagcttt    7560
ccgtggagca ggcccttggc atgatgaatg tcgacggtga actgacggcc aaagaagtgg    7620
agaaactgaa aagaataatt gacaaacttc agggccttac taaggagcag tgtttaaact    7680
gctagccgcc agcggcttga cccgctgtgg tcgcggcggc ttggttgtta ctgagacagc    7740
ggtaaaaata gtcaaatttc acaaccggac tttcacccta gggcctgtga atttaaaagt    7800
ggccagtgag gttgagctga aagacgcggt cgagcacaac caacacccgg ttgcaagacc    7860
ggttgacggt ggtgttgtgc tcctgcgttc cgcagttcct tcgcttatag atgtcctgat    7920
ctccggtgct gacgcatctc ctaagttact cgctcgtcac gggccgggga acactgggat    7980
cgatggcacg ctttgggact tgaggccgga ggccaccaaa gaggaaattg cgctcagtgc    8040
```

```
gcaaataata caggcttgtg acattaggcg cggtgacgca cctgaaattg gtctccctta    8100
caagctgtac cctgttaggg gcaaccctga gcgggtaaaa ggagttttac agaatacaag    8160
gtttggagac ataccttaca aaaccccag tgacactggg agcccagtgc acgcggctgc     8220
ctgcctcacg cccaatgcca ctccggtgac tgatgggcgc tccgtcttgg ctactaccat    8280
gccctccggt tttgaattgt atgtaccgac cattccagcg tctgtccttg attatcttga    8340
ctctaggcct gactgcccca aacagttgac agagcacggc tgtgaggatg ccgcattgag    8400
agacctctcc aagtatgact tgtccaccca aggctttgtt ttacctgggg ttcttcgcct    8460
tgtgcgtaag tacctgtttg cccacgtggg taagtgcccg cccgttcatc ggccttccac    8520
ttaccctgcc aagaattcta tggctggaat aaatgggaac aggtttccaa ccaaggacat    8580
tcagagcgtc cccgaaatcg acgttctgtg cgcacaggcc gtgcgagaaa actggcaaac    8640
tgttacccct tgtaccctca agaaacagta ttgtgggaag aagaagacta ggacaatact    8700
cggcaccaat aatttcattg cgttggccca ccgggcagcg ttgagtggtg tcacccaggg    8760
cttcatgaaa aaggcgttta actcgcccat cgccctcggg aaaaacaaat taaggagct     8820 acagactccg atcttaggca ggtgccttga agctgatctt gcatcctgtg atcgatccac    8880
acctgcaatt gtccgctggt ttgccgccaa ccttcttat gaacttgcct gtgctgaaga     8940
gcacctaccg tcgtacgtgc tgaactgctg ccatgaccta ttggtcacgc agtccggcgc    9000
agtgactaag aggggtggcc tgtcgtctgg cgacccgatc acttctgtgt ctaacaccat    9060
ttacagcttg gtgatatatg cacagcacat ggtgcttagt tactttaaaa gtggtcaccc    9120
tcatggcctt ctgttcctac aagaccagct gaagttcgag gacatgctca aagtccaacc    9180
cctgatcgtc tattcggacg acctcgtgct gtatgccgaa tctcccacca tgccgaacta    9240
ccactggtgg gtcgaacatc tgaatttgat gctgggtttt cagacggacc caaagaagac    9300
agccataacg gactcgccat catttctagg ctgtaggata taaatggac gccagctagt     9360 ccccaaccgt gacaggatcc tcgcggccct cgcttaccat atgaaggcaa acaatgtttc    9420
tgaatactac gccgcggcgg ctgcaatact catggacagc tgtgcttgtt tagagtatga    9480
tcctgaatgg tttgaagagc ttgtggttgg gatagcgcat tgcgcccgca aggacggcta    9540
cagctttccc ggcccgccgt tcttcttgtc catgtgggaa aaactcagat ccaatcatga    9600
ggggaagaag tccagaatgt gcgggtattg cggggccctg gctccgtacg ccactgcctg    9660
tggcctcgac gtctgtattt accacaccca cttccaccag cattgtccag tcacaatctg    9720
gtgtggccac ccggctggtt ctggttcttg tagtgagtgc aaaccccccc tagggaaagg    9780
cacaagccct ctagatgagg tgttagaaca agtcccgtat aagcctccac ggactgtaat    9840
catgcatgtg gagcagggtc tcacccctct tgacccaggc agataccaga ctcgccgcgg    9900
attagtctcc gttaggcgtg gcatcagagg aaatgaagtt gacctaccag acggtgatta    9960
tgctagcacc gccctactcc ccacttgtaa agagatcaac atggtcgctg tcgcctctaa    10020
tgtgttgcgc agcaggttca tcatcggtcc gcccggtgct gggaaaacat actggctcct    10080
tcagcaggtc caggatggtg atgtcattta cacaccgact caccagacca tgctcgacat    10140
gattagggct ttggggacgt gccggttcaa cgtcccagca ggtgcaacgc tgcaattccc    10200
tgccccctcc cgtaccggcc cgtgggttcg catcctagcc ggcggttggt gtcctggtaa    10260
gaattccttc ttggatgaag cagcgtattg taatcaccct gatgtcttga ggctccttag    10320
caaaaccacc ctcacctgtc tgggagactt caaacaactc cacccagtgg gttttgattc    10380
```

```
tcattgctat gttttgaca tcatgcctca gacccagttg aagaccatct ggagattcgg   10440
acagaacatc tgtgatgcca tccaaccaga ttacagggac aaacttgtgt ccatggtcaa   10500
cacaacccgt gtaacccacg tggaaaaacc tgtcaagtat gggcaagtcc tcacccctta   10560
ccacagggac cgagaggacg gcgccatcac aattgactcc agtcaaggcg ccacatttga   10620
tgtggtcaca ctgcatttgc ccactaaaga ttcactcaac aggcaaagag cccttgttgc   10680
tatcaccagg gcaagacatg ctatctttgt gtatgaccca cacaggcaat tgcagagcat   10740
gtttgatctt cctgcgaagg gcacacccgt caacctcgca gtgcaccgtg atgagcagct   10800
gatcgtactg gatagaaata ataaagaatg cacagttgct caggctctag caacggaga   10860 taaatttagg gccaccgaca agcgcgttgt agattctctc cgcgccattt gtgctgatct   10920
ggaagggtcg agctctccgc tccccaaggt cgcacacaac ttgggatttt atttctcacc   10980
tgatttgaca cagtttgcta aactcccggt agaccttgca ccccactggc ccgtggtgac   11040
aacccagaac aatgaaaagt ggccggatcg gctggttgcc agccttcgcc ctgtccataa   11100
gtatagccgt gcgtgcattg gtgccggcta tggtgggc ccctcggtgt ttctaggcac   11160
ccctggggtc gtgtcatact acctcacaaa atttgtcaag gcgaggctc aagtgcttcc   11220 ggagacagtc ttcagcaccg gccgaattga ggtggattgc cggagtatc ttgatgacag   11280 ggagcgagaa gttgctgagt ccctcccaca tgccttcatt ggcgacgtca aaggcaccac   11340
cgttggggga tgtcatcatg tcacctccaa ataccttccg cgcttccttc caaggaatc   11400 agtcgcggta gtcggggttt cgagccccgg gaaagccgca aaagcagtgt gcacattgac   11460
ggatgtgtac ctcccagacc ttgaggccta cctccaccca gagactcagt ccaagtgctg   11520
gaaagttatg ttggacttca aggaagttcg actgatggtc tggaaagaca agacggccta   11580
tttccaactt gaaggccgct atttcacctg gtatcagctt gcaagctacg cctcgtacat   11640
ccgtgttcct gtcaactcca cggtgtatct ggacccctgc atgggccctg cccttttgcaa   11700 cagaagagtt gtcgggtcca cccattgggg agctgacctc gcagtcaccc cttatgatta   11760
cggtgctaaa atcatcttgt ctagcgctta ccatggtgaa atgcctcctg gatacaagat   11820
tctggcgtgc gcggagttct cgctcgacga cccagtcaag tacaaacaca cctggggttt   11880
tgaatcggat acagcgtatc tgtatgagtt caccggaaac ggtgaggact gggaggatta   11940
caatgatgcg tttcgtgcgc gccagaaagg gaaaatttat aaggccactg ctaccagcat   12000
gaagttttat tttcccccgg gccccgtcat tgaaccaact ttaggcctga attgaaatga   12060 aatgggtct atacaaagcc tcttcgacaa aattggccag cttttttgtgg atgctttcac   12120 ggaatttttg gtgtccattg ttgatatcat catattttg gccattttgt ttggcttcac   12180
catcgccggt tggctggtgg tcttttgcat cagattggtt tgctccgcgg tattccgtgc   12240
gcgccctgcc attcaccctg agcaattaca gaagatccta tgaggccttt ctttctcagt   12300
gccgggtgga cattcccacc tggggggtaa acacccttt ggggatgttt tggcaccata   12360
aggtgtcaac cctgattgat gaaatggtgt cgcgtcgaat gtaccgcgtc atggataaag   12420
cagggcaagc tgcctggaaa caggtggtga gcgaggctac gctgtctcgc attagtagtc   12480
tggatgtggt ggctcatttt caacatcttg ccgccattga agccgagacc tgtaaatatt   12540
tggcttctcg actgccatg ctacacaacc tgcgcatgac agggtcaaat gtaaccatag   12600
tgtataatag cactttaaat caggtgtttg ctattttcc aacccctggt tcccggccaa   12660
agcttcatga ttttcagcaa tggctaatag ctgtacattc ctccatattt tcctctgttg   12720
cagcttcttg tactcttttt gttgtgctgt ggttgcgggt tccaatgcta cgtactgttt   12780
```

```
ttggtttccg ctggttaggg gcaattttc tttcgaactc atggtgaatt acacggtgtg   12840
tccaccttgc ctcacccgac aagcagccgc tgaggtcctt gaacccggta ggtctctttg   12900
gtgcaggata gggcatgacc gatgtgggga ggacgatcac gacgaactgg ggttcatggt   12960
tccgcctggc ctctccagcg aaagccactt gaccagtgtt tacgcctggt tggcgttcct   13020
gtccttcagc tacacggccc agttccatcc cgagatattt gggataggga acgtgagtga   13080
agtttatgtt gacatcaagc accaattcat ctgcgccgtt catgacgggc agaacaccac   13140
cttgcctcgc catgacaata tttcagccgt atttcagacc tactatcaac atcaggtcga   13200
cggcggcaat tggtttcacc tagaatggct gcgtcccttc ttttcctctt ggttggtttt   13260
aaatgtttcg tggtttctca ggcgttcgcc tgcaagccat gtttcagttc gagtctttca   13320
gacatcaaaa ccaacactac cgcagcatca ggctttgttg tcctccagga catcagctgc   13380
cttaggcatg gcgactcgtc ctttccgacg attcgcaaaa gctctcaatg ccgcacggcg   13440
atagggacac ctgtgtatat caccatcaca gccaatgtga cagatgagaa ttacttacat   13500
tcttctgatc tcctcatgct ttcttcttgc cttttctatg cttctgagat gagtgaaaag   13560
ggattcaagg tggtatttgg caatgtgtca ggcatcgtgg ctgtgtgtgt caactttacc   13620
agctacgtcc aacatgtcaa agagtttact caacgctcct tggtggtcga tcatgtgcgg   13680
ctgcttcatt tcatgacacc tgagaccatg aggtgggcaa ccgttttagc ctgtcttttt   13740
gccatcctac tggcaatttg aatgttcaag tatgttgggg aaatgcttga ccgcgggctg   13800
ttgctcgcga ttgctttctt tgtggtgtat cgtgccgttc tggtttgctg tgctcggcaa   13860
cgccaacagc agcagcagct ctcatttcca gttgatttat aacttgacgc tatgtgagct   13920
gaatggcaca gattggctgg cagaaaaatt tgattgggcg gtggagactt ttgtcatctt   13980
tcccgtgttg actcacattg tttcctattg tgcactcacc accagccatt ccttgacac    14040 agttggtctg gttactgtgt ccaccgccgg gttttatcac gggcggtatg tcttgagtag   14100
catctacgcg gtctgtgctc tggctgcgtt gatttgcttc gttattaggc ttgcgaagaa   14160
ctgcatgtcc tggcgctact cttgtaccag atataccaac ttccttctgg acactaaggg   14220
cagactctat cgttggcggt cgcccgttat catagaaaaa aggggtaagg ttgaggtcga   14280
aggtcatctg atcgacctca aaagagttgt gcttgatggt tccgtggcaa cccctttaac   14340
cagagtttca gcgaacaat  ggggtcgtct ctagacgact tttgccatga tagcactgct   14400
ccacaaaagg tgcttttggc gttttccatt acctacacgc cagtaatgat atatgctcta   14460
aaggtaagtc gcggccgact gctagggctt ctgcaccttt tgatctttct gaattgtgct   14520
tttaccttcg ggtacatgac attcgcgcac tttcagagca caaatagggt cgcgctcgct   14580
atgggagcag tagttgcact tctttggggg gtgtactcag ccatagaaac ctggaaattc   14640
atcacctcca gatgccgttt gtgcttgcta ggccgcaagt acattctggc ccctgcccac   14700
cacgtcgaaa gtgccgcggg ctttcatccg attgcggcaa atgataacca cgcatttgtc   14760
gtccggcgtc ccggctccat tacggttaac ggcacattgg tgcccgggtt gaaaagcctc   14820
gtgttgggtg gcagaaaagc tgttaaacag ggagtggtaa accttgtcaa atatgccaaa   14880
taacaacggc aagcagcaaa agaaaaagaa ggggaatggc cagccagtca accagctgtg   14940
ccagatgctg ggtaaaatca tcgcccagca aaaccagtcc agaggcaagg gaccgggcaa   15000
gaaaagtaag aagaaaaacc cggagaagcc ccatttttcct ctagcgaccg aagatgacgt   15060
caggcatcac ttcaccctg gtgagcggca attgtgtctg tcgtcgatcc agactgcctt   15120
```

```
taaccagggc gctggaactt gtaccctgtc agattcaggg aggataagtt acactgtgga    15180
gtttagtttg ccgacgcatc atactgtgcg cctgatccgc gtcacagcat caccctcagc    15240
atgatgggct ggcattcttt aggcacctca gtgtcagaat tggaagaatg tgtggtggat    15300
ggcactgatt gacattgtgc ctctaagtca cctattcaat tagggcgacc gtgtggggggt    15360 aaaatttaat tggcgagaac catgcggccg caattaaaaa aaaaaaaaaa aaaaaaaaaa    15420
aaaaaaaaaa aaaaaaaaaa aaaaaaaaaa                                    15450

<210> SEQ ID NO 17
<211> LENGTH: 2352
<212> TYPE: DNA
<213> ORGANISM: Porcine reproductive and respiratory syndrome virus

<400> SEQUENCE: 17
cctatcattg aaccaacttt aggcctgaat tgaaatgaaa tggggtctat gcaaagcctt      60
tttgacaaaa ttggccaact tttcgtggat gctttcacgg agttcttggt gtccattgtt     120
gatatcatta tattttggc cattgtgttt ggcttcacca tcgccggttg gctggtggtc      180
ttttgcatca gattggtttg ctccgcgata ctccgtgcgc gccctgccat tcactctgag     240
caattacaga agatcctatg aggcctttct ttctcagtgc caggtggaca ttcccacctg     300
gggaattaaa catcctttgg ggatgctttg gcaccataag gtgtcaaccc tgattgatga     360
aatggtgtcg cgtcgaatgt accgcatcat ggaaaaagca ggacaggctg cctggaaaca     420
ggtggtgagc gaggctacgc tgtctcgcat tagtagtttg gatgtggtgg ctcactttca     480
gcatcttgcc gccattgaag ccgagacctg taaatatttg gcctctcggc tgcccatgct     540
acacaacctg cgcatgacag ggtcaaatgt aaccatagtg tataatagta ctttgaatca     600
ggtgcttgct attttcccaa cccctggttc ccggccaaag cttcatgatt ttcagcaatg     660
gctaatagct gtacattcct ctatattttc ctctgttgca gcttcttgta ctcttttgt      720 tgtgctgtgg ttgcgggttc caatgctacg tattgctttt ggtttccgct ggttagggc      780 aattttttctt tcgaactcac agtgaactac acggtgtgtc caccttgcct cacccggcaa    840
gcagccacag aggcctacga acctggcagg tctcttggt gcaggatagg gtatgatcgc      900 tgtgggagg acgatcatga tgaactaggg tttgtggtgc cgtctggcct ctccagcgaa      960
ggccacttga ccagtgttta cgcctggttg gcgttcctgt ctttcagtta cagcccag     1020 ttccatcctg agatattcgg ataggggaat gtgagtcaag tttatgttga catcaggcat     1080
caattcattt gcgccgttca cgacgggcag aacgccactt gcctcgcca tgacaatatt     1140 tcagccgtgt tccagactta ttaccaacat caagtcgacg gcggcaattg gtttcaccta     1200
gaatggctgc gtcccttctt ttcctcttgg ttggttttaa atgtctcttg gtttctcagg     1260
cgttcgcctg caagccatgt tcagttcga gtcttgcaga cattaagacc aacaccaccg     1320
cagcggcagg ctttgctgtc ctccaagaca tcagttgcct taggtatcgc aactcggcct     1380
ctgaggcgtt tcgcaaaatc cctcagtgtc gtacggcgat agggacaccc atgtatatta     1440
ctgtcacagc caatgtaacc gatgagaatt atttgcattc ctctgacctt ctcatgcttt     1500
cttcttgcct tttctacgct tctgagatga gtgaaaaggg atttaaagtg gtatttggca     1560
atgtgtcagg catcgtggct gtgtgcgtca actttaccag ctacgtccaa catgtcaagg     1620
aatttaccca acgctccttg gtagtcgacc atgtgcggct gctccatttc atgacacctg     1680
agaccatgag gtgggcaact gttttagcct gtcttttgc cattctgttg gccatttgaa     1740
tgtttaagta tgttggggaa atgcttgacc gcgggctatt gctcgtcatt gcttttttgt     1800
```

```
tggtgtatcg tgccgtcttg gtttgttgcg ctcgccagcg ccaacagcag caacagctct    1860
catttacagt tgatttataa cttgacgcta tgtgagctga atggcacaga ttggttagct    1920
ggtgaatttg actgggcagt ggagtgtttt gtcattttc ctgtgttgac tcacattgtc     1980
tcctatggtg ccctcaccac cagccatttc cttgacacag tcggtctggt cactgtgtct    2040
accgccggct tttcccacgg gcggtatgtt ctgagtagca tctacgcggt ctgtgccctg    2100
gctgcgttga tttgcttcgt cattaggttt acgaagaatt gcatgtcctg gcgctactca    2160
tgtaccagat ataccaactt tcttctggac actaagggca gactctatcg ttggcggtcg    2220
cctgtcatca tagagaaaag gggtaaagtt gaggtcgaag gtcatctgat cgacctcaag    2280
agagttgtgc ttgatggttc cgcggcaacc cctataacca aagtttcagc ggagcaatgg    2340
ggtcgtcctt ag                                                        2352

<210> SEQ ID NO 18
<211> LENGTH: 886
<212> TYPE: DNA
<213> ORGANISM: Porcine reproductive and respiratory syndrome virus

<400> SEQUENCE: 18
atggggtcgt ccttagatga cttctgccat gatagcacgg ctccacaaaa ggtgcttttg      60
gcgttctcta ttacctacac gccagtgatg atatatgccc taaaagtaag tcgcggccga     120
ctgctagggc ttctgcacct tttgatcttc ctaaattgtg ctttcacctt cgggtacatg     180
acattcgtgc actttcagag cacaaacaag gtcgcgctca ctatgggagc agtagttgca     240
ctcctttggg gggtgtactc agccatagaa acctggaaat tcatcacctc cagatgccgt     300
ttgtgcttgc taggccgcaa gtacattttg gcccctgccc accacgttga aagtgccgca     360
ggctttcatc cgatagcggc aaatgataac cacgcatttg tcgtccggcg tcccggctcc     420
actacggtta acggcacatt ggtgcccggg ttgaaaagcc tcgtgttggg tggcagaaaa     480
gctgtcaaac agggagtggt aaaccttgtt aaatatgcca ataacaacg gcaagcagca     540 gaagaaaaag aaggggatg ccagccagt caatcagctg tgccagatgc tgggtaagat      600
catcgctcag caaaaccagt ccagaggcaa gggaccggga agaaaaaca agaagaaaaa      660 cccggagaag ccccatttc ctctagcgac tgaagatgat gtcagacatc acttcacctc      720
tggtgagcgg caattgtgtc tgtcgtcaat ccagacagcc tttaatcaag gcgctggaac      780
ttgtaccctg tcagattcag ggaggataag ttacactgtg gagtttagtt tgccgacgca      840
tcatactgtg cgcctgatcc gcgtcacagc gtcaccctca gcatga                    886
```

PCV/*MYCOPLASMA HYOPNEUMONIAE* COMBINATION VACCINE

CROSS-REFERENCE TO RELATED APPLICATIONS

This application claims the benefit of U.S. Provisional Application No. 61/620,175, filed Apr. 4, 2012, the contents of which are incorporated herein by reference in their entirety.

FIELD OF THE INVENTION

The present invention relates to porcine circovirus and *Mycoplasma hyopneumoniae* (*M. hyopneumoniae* or *M. hyo*). More particularly, the invention relates to a multivalent immunogenic composition including a soluble portion of an *M. hyo* whole cell preparation and a PCV2 antigen and its use in a vaccine for protecting pigs against enzootic pneumonia and Post-weaning Multisystemic Wasting Syndrome (PMWS).

BACKGROUND OF THE INVENTION

Enzootic pneumonia in swine, also called mycoplasmal pneumonia, is caused by *M. hyo*. The disease is a chronic, non-fatal disease affecting pigs of all ages. Infected pigs show only mild symptoms of coughs and fever, but the disease has significant economic impact due to reduced feed efficiency and reduced weight gain. Enzootic pneumonia is transmitted from pig to pig through the nasal passages by airborne organisms expelled from the lungs of infected pigs. The primary infection by *M. hyo* may be followed by secondary infection by other *mycoplasma* species (*Myoplasma hyorhinis* and *Mycoplasma flocculare*) as well as other bacterial pathogens.

*M. hyo* is a small, prokaryotic microbe capable of a free living existence, although it is often found in association with eukaryotic cells because it has absolute requirements for exogenous sterols and fatty acids. These requirements generally necessitate growth in serum-containing media. *M. hyo* is bounded by a cell membrane, but not a cell wall.

The physical association of *mycoplasmas* with the host cell surface is the basis for the development and persistence of enzootic pneumonia. *M. hyo* infects the respiratory tract of swine, colonizing the trachea, bronchi, and bronchioles. The *mycoplasma* produces a ciliostatic factor which causes the cilia lining the respiratory passages to stop beating. Eventually, the cilia degenerate, leaving the pig prone to infection by secondary pathogens. Characteristic lesions of purple to gray areas of consolidation are observed in infected animals. Surveys of slaughtered animals revealed lesions in 30 to 80% of swine. Results from 37 herds in 13 states indicated that 99% of the herds had hogs with pneumonia lesions typical of enzootic pneumonia. Therefore, the need for effective preventative and treatment measures are great.

Antibiotics such as tiamulin, trimethoprim, tetracyclines and lincomycin have some benefit, but are expensive and require prolonged use. Additionally, antibiotics have not been shown to effectively eliminate spread or reinfection of *M. hyo*. Prevention by maintaining pathogen-free herds is sometimes possible but reintroduction of *M. hyo* often occurs. Due to the serious economic consequences of swine pneumonia, vaccines against *M. hyo* have been sought. Vaccines containing preparations of mycoplasmal organisms grown in serum-containing medium have been marketed, but raise concerns regarding adverse reactions induced by serum components (such as immunocomplexes or non-immunogenic specific proteins) present in the immunizing material. Other attempts to provide *M. hyo* vaccines have been successful, but the disease remains widespread.

*M. hyo* and porcine circovirus type 2 (PCV2) are the two most prevalent pathogens that are encountered in the pig industry. Swine infected with PCV2 exhibit a syndrome commonly referred to as Post-weaning Multisystemic Wasting Syndrome (PMWS). PMWS is clinically characterized by wasting, paleness of the skin, unthriftiness, respiratory distress, diarrhea, icterus, and jaundice. In addition to PMWS, PCV2 has been associated with several other infections including pseudorabies, porcine reproductive and respiratory syndrome (PRRS), Glasser's disease, streptococcal meningitis, salmonellosis, postweaning colibacillosis, dietetic hepatosis, and suppurative bronchopneumonia. *M. hyo* is associated with enzootic pneumonia and has also been implicated as one of the major co-factors in the development of Porcine Circovirus Associated Disease (PCVAD).

Porcine reproductive and respiratory syndrome (PRRS) is caused by an arterivirus, which has a particular affinity for the macrophages particularly those found in the lung (alveolar macrophages). These macrophages ingest and remove invading bacteria and viruses, but not in the case of the PRRS virus (PRRSV). In the case of the PRRS virus, it multiplies inside the macrophages producing more virus and kills the macrophages. Once PRRSV has entered a herd, it tends to remain present and active indefinitely. Up to 40% of the macrophages are destroyed, which allows bacteria and other viruses to proliferate and do damage. A common example of this is the noticeable increase in severity of enzootic pneumonia in grower/finisher units when they become infected with PRRS virus. More than half of weaning-age PRRS virus-negative pigs become infected before going to market.

What is needed is a PCV2/*M. hyo* combination vaccine against both PCV2 and *mycoplasma* infection in swine. Preferably, this multivalent vaccine will be compatible with other porcine antigens, such as PRRS virus antigen. It would be highly desirable to provide a ready-to-use in one bottle, single-dose PCV2/*M. hyo* combination vaccine.

SUMMARY OF THE INVENTION

The present invention provides a multivalent immunogenic composition including a soluble portion of a *Mycoplasma hyopneumoniae* (*M. hyo*) whole cell preparation; and a porcine circovirus type 2 (PCV2) antigen, wherein the soluble portion of the *M. hyo* preparation is substantially free of both (i) IgG and (ii) immunocomplexes comprised of antigen bound to immunoglobulin. In one aspect, the soluble portion of the *M. hyo* whole cell preparation has been treated with protein-A or protein-G prior to being added to the immunogenic composition. In a further aspect, the composition is in the form of a ready-to-use liquid composition.

In one embodiment, the soluble portion of the *M. hyo* preparation includes at least one *M. hyo* protein antigen. In another embodiment, the soluble portion of the *M. hyo* preparation includes two or more *M. hyo* protein antigens.

In some embodiments, the composition of the present invention elicits a protective immune response against *M. hyo* and PCV2. In one embodiment, the PCV2 antigen is in the form of a chimeric type-1-type 2 circovirus, the chimeric virus including an inactivated recombinant porcine circovirus type 1 expressing the porcine circovirus type 2 ORF2 protein. In another embodiment, the PCV2 antigen is in the form of a recombinant ORF2 protein. In still another embodiment, the recombinant ORF2 protein is expressed from a baculovirus vector.

In some embodiments, the PCV2/*M. hyo* composition of the present invention further includes at least one additional antigen. In one embodiment, the at least one additional antigen is protective against a microorganism that can cause disease in pigs.

In one embodiment, the microorganism includes bacteria, viruses, or protozoans. In another embodiment, the microorganism is selected from, but is not limited to, the following: porcine reproductive and respiratory syndrome virus (PRRSV), porcine parvovirus (PPV), *Haemophilus parasuis, Pasteurella multocida, Streptococcum sills, Staphylococcus hyicus, Actinobacilllus pleuropneumoniae, Bordetella bronchiseptica, Salmonella eholeraesuis, Salmonella enteritidis, Erysipelothrix rhusiopathiae, Mycoplama hyorhinis, Mycoplasma hyosynoviae*, leptospira bacteria, *Lawsonia intracellularis*, swine influenza virus (SEN), *Escherichia coli* antigen. *Brachyspira hyodysenteriae*, porcine respiratory coronavirus. Porcine Epidemic Diarrhea (PED) virus, rotavirus, Torque teno virus (ITV). Porcine Cytomegalovirus, Porcine enteroviruses, Encephalomyocarditis virus, a pathogen causative of Aujesky's Disease, Classical Swine fever (CSF) and a pathogen causative of Swine Transmissable Gastroenteritis, or combinations thereof.

In some embodiments, the composition of the present invention further includes an adjuvant. In one embodiment, the adjuvant is selected from, but is not limited to, the following: an oil-in-water adjuvant, a polymer and water adjuvant, a water-in-oil adjuvant, an aluminum hydroxide adjuvant, a vitamin E adjuvant and combinations thereof. In another embodiment, the composition of the present invention further includes a pharmaceutically acceptable carrier.

In certain embodiments, the composition of the present invention elicits a protective immune response against both *M. hyo* and PCV2 when administered as a single dose administration. In further embodiments, the composition elicits a protective immune response against *M. hyo*, PCV2, and at least one additional microorganism that can cause disease in pigs when administered as a single dose administration. In still further embodiments, a composition of the present invention elicits a protective response against both *M. hyo* and PCV2 when administered as a two dose administration.

The present invention also provides a method of immunizing a pig against *M. hyo* and PCV2. This method includes administering to the pig an immunogenic composition including a soluble portion of a *Mycoplasma hyopneumoniae* (*M. hyo*) whole cell preparation; and a porcine circovirus type 2 (PCV2) antigen, wherein the soluble portion of the *M. hyo* preparation is substantially free of both (i) IgG and immunocomplexes comprised of antigen bound to immunoglobulin. In one embodiment, the soluble portion of the *M. hyo* preparation of the administered composition includes at least one *M. hyo* protein antigen.

In one embodiment of the method of the present invention, the composition is administered intramuscularly, intradermally, transdermally, or subcutaneously. In another embodiment of the method of this invention, the composition is administered in a single dose. In yet another embodiment of the method of this invention, the composition is administered as two doses.

In a further embodiment of the method of the present invention, the PCV2/*M. hyo* composition is administered in conjunction with at least one additional antigen that is protective against a microorganism that can cause disease in pigs, such as one or more of the microorganisms described above. Such other antigens can be given concurrently with the PCV2/*M. hyo* composition (i.e., as separate single vaccines) or combined in a ready-to-use vaccine.

In a further embodiment, the composition is administered to pigs having maternally derived antibodies against at least one of *M. hyo* and PCV2. In a still further embodiment, the composition is administered to pigs having maternally derived antibodies against both *M. hyo* and PCV2.

In one embodiment, the composition is administered to pigs at 3 weeks of age or older.

The present invention further provides a kit. This kit contains a bottle including an immunogenic composition. This immunogenic composition includes both a PCV2 antigen and the soluble portion of a *Mycoplasma hyopneumoniae* (*M. hyo*) whole cell preparation, wherein the soluble portion of the *M. hyo* preparation is substantially free of both (i) IgG and (ii) antigen/immunoglobulin immunocomplexes. In one embodiment, this kit further includes an instruction manual which contains the information to administer the immunogenic composition. In another embodiment, the immunogenic composition in the bottle is provided as a ready-to-use liquid composition.

Additionally, the present invention provides a method for preparing an immunogenic composition. This method includes: i) culturing *M. hyo* in a suitable media over periods ranging from 18-144 hours; ii) subsequently inactivating the *M. hyo* culture; iii) harvesting the inactivated culture fluid, wherein the inactivated culture fluid comprises an *M. hyo* whole cell preparation comprising both a soluble liquid fraction and insoluble cellular material; iv) separating the soluble liquid fraction from the insoluble cellular material; v) substantially removing both IgG and antigen/immunoglobulin immunocomplexes from the separated soluble liquid fraction to form a soluble portion of the *M. hyo* whole cell preparation; and vi) subsequently combining the soluble portion of the *M. hyo* whole cell preparation with a PCV2 antigen.

BRIEF DESCRIPTION OF THE DRAWINGS

FIG. 10 is a table showing the adjuvant evaluation for virucidal activity against PRRS virus.

BRIEF DESCRIPTION OF THE SEQUENCES

Figure 1:
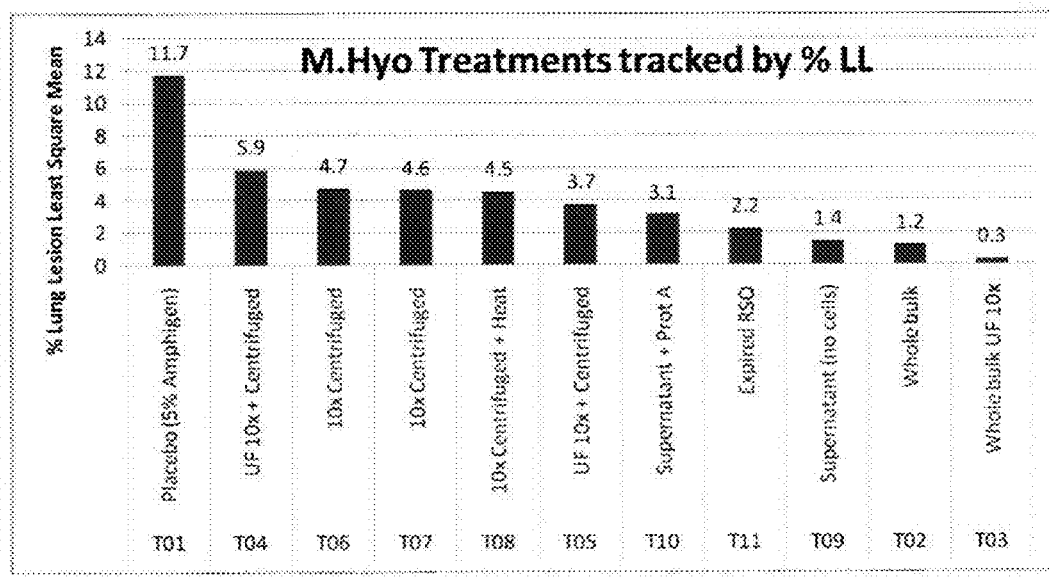
FIG. 1 is a graph showing the efficacy of *M. hyo* monovalent vaccines prepared with *M. hyo* antigens from different treatments (T02-T10 described in Example 3) vs. a placebo (T01). The results are presented as % Lung Lesion Least Square Mean values.

SEQ ID NO: 1 is one embodiment of a nucleotide sequence encoding p46 from the P-5722 strain of *M. hyo;*
SEQ ID NO: 2 is one embodiment of an amino acid sequence corresponding to p46 from the P-5722 strain of *M. hyo;*
SEQ ID NO: 3 is one embodiment of a nucleotide sequence encoding p97 from the P-5722 strain of *M. hyo;*
SEQ ID NO: 4 is one embodiment of an amino acid sequence corresponding to p97 from the P-5722 strain of *M. hyo;*
SEQ ID NO: 5 is one embodiment of a genomic sequence encoding a chimeric PCV1-2 virus:
SEQ ID NO: 6 is one embodiment of a nucleotide sequence corresponding to ORF2 of a porcine circovirus;
SEQ NO: 7 is one embodiment of an amino acid sequence corresponding to the ORF2 polypeptide of a porcine circovirus;
SEQ ID NO: 8 is one embodiment of a genomic sequence encoding a chimeric PCV1-2 virus;
SEQ ID NO: 9 is one embodiment of a nucleotide sequence corresponding to ORF2 of a porcine circovirus;
SEQ ID NO: 10 is one embodiment of an amino acid sequence corresponding to the ORF2 polypeptide of a porcine circovirus;
SEQ ID NO: 11 is one embodiment of an amino acid sequence corresponding to the ORF2 polypeptide of a porcine circovirus;
SEQ ID NO: 12 is one embodiment of a nucleotide sequence encoding the amino acid sequence of SEQ ID NO: 11;
SEQ ID NO: 13 is one embodiment of an amino acid sequence corresponding to the ORF2 polypeptide of a porcine circovirus;
SEQ ID NO: 14 is one embodiment of a nucleotide sequence encoding the amino acid sequence of SEQ ID NO: 13;
SEQ ID NO: 15 is one embodiment of an amino acid sequence corresponding, to the ORF2 polypeptide of a porcine circovirus;
SEQ ID NO: 16 is one embodiment of a genomic sequence of a non-virulent form of the North American PRRS virus isolate designated P129; and
SEQ ID NO: 17 is one embodiment of a nucleotide sequence corresponding to ORF2 to ORF5 of the PRRS virus isolate designated ISU-55.
SEQ ID NO: 18 is one embodiment of a nucleotide sequence corresponding to ORF6 and ORF7 of the PRRS virus isolate designated ISU-55.

DETAILED DESCRIPTION OF THE INVENTION

The present invention provides a multivalent immunogenic composition including a soluble portion of a *Mycoplasma hyopneumoniae* (*M. hyo*) whole cell preparation; and a porcine circovirus type 2 (PCV2) antigen, wherein the soluble portion of the *M. hyo* preparation is substantially free of both (i) IgG and (ii) immunocomplexes comprised of antigen bound to immunoglobulin. In one embodiment, the composition elicits a protective immune response in a pig against both PCV2 and *M. hyo*.

Applicants have surprisingly discovered that the insoluble fraction of the *M. hyo* whole cell preparation is non-immunogenic. In contrast, the IgG-free *M. hyo* soluble preparation is immunogenic and can be effectively combined with antigens from other pathogens, such as PCV2, without analytical or immunological interference between the antigens. This makes the *M. hyo* soluble preparation an effective platform for the multivalent vaccines of this invention, including one-bottle, ready-to-use formulations. Applicants have also surprisingly discovered that removing the immunoglobulin and the insoluble cell debris from the *M. hyo* preparation enhances the safety of the immunogenic composition.

As used in the specification and claims, the singular form "a", "an" and "the" include plural references unless the context clearly dictates otherwise. For example, the term "a protein antigen" includes a plurality of protein antigens, including mixtures thereof.

As used herein, the term "comprising" is intended to mean that the compositions and methods include the recited elements, but do not exclude other elements.

As defined herein, a soluble portion of an *M. hyo* whole cell preparation refers to a soluble liquid fraction of an *M. hyo* whole cell preparation after separation of the insoluble material and substantial removal of IgG and antigen-bound immunocomplexes. The *M. hyo* soluble portion may alternatively be referred to herein as the supernatant fraction, culture supernatant and the like. It includes *M. hyo*-expressed soluble proteins (*M. hyo* protein antigens) that have been separated or isolated from insoluble proteins, whole bacteria, and other insoluble *M. hyo* cellular material by conventional means, such as centrifugation, filtration, or precipitation. In addition to including *M. hyo*-specific soluble proteins, the soluble portion of the *M. hyo* whole cell preparation also includes heterologous proteins, such as those contained in the culture medium used for *M. hyo* fermentation.

The term "antigen" refers to a compound, composition, or immunogenic substance that can stimulate the production of antibodies or a T-cell response, or both, in an animal, including compositions that are injected or absorbed into an animal. The immune response may be generated to the whole molecule, or to a portion of the molecule (e.g., an epitope or hapten).

As defined herein, an "immunogenic or immunological composition", refers to a composition of matter that comprises at least one antigen which elicits an immunological response in the host of a cellular and or antibody-mediated immune response to the composition or vaccine of interest.

The term "immune response" as used herein refers to a response elicited in an animal. An immune response may refer to cellular immunity (CMI); Immoral immunity or may involve both. The present invention also contemplates a response limited to a part of the immune system. Usually, an "immunological response" includes, but is not limited to, one or more of the following elects: the production or activation of antibodies, B cells, helper T cells, suppressor T cells, and/or cytotoxic T cells and/or yd T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

As used herein, the term "immunogenicity" means capable of producing an immune response in a host animal against an antigen or antigens. This immune response forms the basis of the protective immunity elicited by a vaccine against a specific infectious organism.

An "adjuvant" as used herein means a composition comprised of one or more substances that enhances the immune response to an antigen(s). The mechanism of how an adjuvant operates is not entirely known. Some adjuvants are believed to enhance the immune response by slowly releasing the antigen, while other adjuvants are strongly immunogenic in their own right and are believed to function synergistically.

As used herein, the term "multivalent" means a vaccine containing more than one antigen whether from the same species (i.e., different isolates of *Mycoplasma hyopneumoniae*), from a different species (i.e., isolates from both *Pasteurella hemolytica* and *Pasteurella multocida*), or a vaccine containing a combination of antigens from different genera (for example, a vaccine comprising antigens from *Pasteurella multocida, Salmonella, Escherichia coli, Haemophilus somnus* and *Clostridium*).

The term "pig" or "piglet" as used herein means an animal of porcine origin, while "sow" refers to a female of reproductive age and capability, A "gilt" is a female pig who has never been pregnant.

As used herein, the term "virulent" means an isolate that retains its ability to be infectious in an animal host.

"Inactivated vaccine" means a vaccine composition containing an infectious organism or pathogen that is no longer capable of replication or growth. The pathogen may be bacterial, viral, protozoal or fungal in origin. Inactivation may be accomplished by a variety of methods including freeze-thawing, chemical treatment (for example, treatment with thimerosal or formalin), sonication, radiation, heat or any other convention means sufficient to prevent replication or growth of the organism while maintaining its immunogenicity.

The term "variant" as used herein refers to a polypeptide or a nucleic acid sequence encoding a polypeptide, that has one or more conservative amino acid variations or other minor modifications such that the corresponding polypeptide has substantially equivalent function when compared to the wild-type polypeptide.

"Conservative variation" denotes the replacement of an amino acid residue by another biologically similar residue, or the replacement of a nucleotide in a nucleic, acid sequence such that the encoded amino acid residue does not change or is another biologically similar residue. Examples of conservative variations include the substitution of one hydrophobic residue, such as isoleucine, valine, leucine or methionine for another hydrophobic residue, or the substitution of one polar residue, such as the substitution of arginine for lysine, glutamic acid for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

As used herein, the terms "pharmaceutically acceptable carrier" and "pharmaceutically acceptable vehicle" are interchangeable and refer to a fluid vehicle for containing vaccine antigens that can be injected into a host without adverse effects. Suitable pharmaceutically acceptable carriers known in the art include, but are not limited to, sterile water, saline, glucose, dextrose, or buffered solutions. Carriers may include auxiliary agents including, but not limited to, diluents, stabilizers sugars and amino acids), preservatives, wetting agents, emulsifying agents, pH buffering agents, viscosity enhancing additives, colors and the like.

As used herein, the term "vaccine composition" includes at least one antigen or immunogen in a pharmaceutically acceptable vehicle useful for inducing an immune response in a host. Vaccine compositions can be administered in dosages and by techniques well known to those skilled in the medical or veterinary arts, taking into consideration such factors as the age, sex, weight, species and condition of the recipient animal, and the route of administration. The route of administration can be percutaneous, via mucosal administration (e.g., oral, nasal, anal, vaginal) or via a parenteral route (intradermal, transdermal, intramuscular, subcutaneous, intravenous, or intraperitoneal). Vaccine compositions can be administered alone, or can be co-administered or sequentially administered with other treatments or therapies. Forms of administration may include suspensions, syrups or elixirs, and preparations for parenteral, subcutaneous, intradermal, intramuscular or intravenous administration (e.g., injectable administration) such as sterile suspensions or emulsions. Vaccine compositions may be administered as a spray or mixed in food and/or water or delivered in admixture with a suitable carrier, diluent, or excipient such as sterile water, physiological saline, glucose, or the like. The compositions can contain auxiliary substances such as wetting or emulsifying agents, pH buffering agents, adjuvants, gelling or viscosity enhancing additives, preservatives, flavoring agents, colors, and the like, depending upon the route of administration and the preparation desired. Standard pharmaceutical texts, such as "Remington's Pharmaceutical Sciences," 1990 may be consulted to prepare suitable preparations, without undue experimentation.

"North American PRRS virus" means any PRRS virus having genetic characteristics associated with a North American PRRS virus isolate, such as, but not limited to the PRRS virus that was first isolated in the United States around the early 1990's (see, e.g., Collins, J. E., et al., 1992, J. Vet. Diagn. Invest. 4:117-126); North American PRRS virus isolate MN-1b (Kwarig, J. et al, 1994, J. Vet, Diagn. Invest, 6:293-296); the Quebec LAF-exp91 strain of PRRS virus (Mardassi, H. et al., 1995, Arch. Virol. 140:1405-1418); and North American PRRS virus isolate VR 2385 (Meng, X.-J et al., 1994, J. Gen, Virol. 75:1795-1801). Additional examples of North American PRRS virus strains are described herein. Genetic characteristics refer to genomic nucleotide sequence similarity and amino acid sequence similarity shared by North American PRRS virus strains. Chinese PRRS virus strains generally evidence about 80-93% nucleotide sequence similarity with North American strains.

"European PRRS virus" refers to any strain of PRRS virus having the genetic characteristics associated with the PRRS virus that was first isolated in Europe around 1991 (see, e.g., Wensvoort, G., et al., 1991, Vet. Q. 13:121-130). "European PRRS virus" is also sometimes referred to in the art as "Lelystad virus". Further examples of European PRRS virus strains are described herein.

A genetically modified virus is "attenuated" if it is less virulent than its unmodified parental strain. A strain is "less virulent" if it shows a statistically significant decrease in one or more parameters determining disease severity. Such parameters may include level of viremia, fever, severity of respiratory distress, severity of reproductive symptoms, or number or severity of lung lesions, etc.

An "Infectious clone" is an isolated or cloned genome of the disease agent (e.g. viruses) that can be specifically and purposefully modified in the laboratory and then used to re-create the live genetically modified organism. A live genetically modified virus produced from the infectious clone can be employed in a live viral vaccine. Alternatively, inactivated virus vaccines can be prepared by treating the live virus derived from the infectious clone with inactivating agents such as formalin or hydrophobic solvents, acids, etc., by irradiation with ultraviolet light or X-rays, by heating, etc.

All currently available M. hyo and M. hyo combination vaccines are made from killed whole cell *mycoplasma* preparations (bacterins). In contrast, the present invention employs a soluble portion of a *Mycoplasma hyopneumoniae* (M. hyo) whole cell preparation for combination with the PCV2 antigen, wherein the soluble portion of the M. hyo preparation is substantially free of both (i) IgG and (ii) immunocomplexes comprised, of antigen bound to inummoglobulin.

M. hyo has absolute requirements for exogenous Sterols and fatty acids. These requirements generally necessitate growth of M. hyo in serum-containing media, such as porcine serum. Separation of the insoluble material from the soluble portion of the M. hyo whole cell preparation by centrifugation, filtration, or precipitation) does not remove the porcine IgG or immune complexes. In one embodiment of the present invention, the M. hyo soluble portion is treated with protein-A or protein-G in order to substantially remove the IgG and immune complexes contained in the culture supernatant. In this embodiment, it is understood that protein A treatment occurs post-M. hyo fermentation. This is alternatively referred to herein as downstream protein A treatment. In another embodiment, upstream protein A treatment of the growth media (i.e., before M. hyo fermentation) can be employed. Protein A binds to the Fc portion of IgG. Protein G binds preferentially to the Fc portion of IgG, but can also bind to the Fab region. Methods for purifying/removing total IgG from crude protein mixtures, such as tissue culture supernatant, serum and ascites fluid are known in the art.

In some embodiments, the soluble portion of the M. hyo preparation includes at least one M. hyo protein antigen. In other embodiments, the soluble portion of the M. hyo preparation includes two or more M. hyo protein antigens.

In one embodiment, the M. hyo supernatant fraction includes one or more of the following M. hyo specific protein antigens: M. hyo proteins of approximately 46 kD (p46), 64 kD (p64) and 97 kD (p97) molecular weights. In another embodiment, the supernatant fraction at least includes the p46, p64 and p97 M. hyo protein antigens. The M. hyo protein of approximately 64 kD (p64) may be alternatively referred to herein as the p65 surface antigen from M. hyo described by Kim et al. [Infect. Inumm, 58(8):2637-2643 (1990)], as well as in U.S. Pat. No. 5,788,962.

Futo et al. described the cloning, and characterization of a 46 kD surface protein from M. hyo, which can be employed in the compositions of this invention [J. Bad 177: 1915-1917 (1995)]. In one embodiment, the M. hyo culture supernatant includes the p46 whose corresponding nucleotide and amino acid sequences from the P-5722 strain are set forth in SEQ ID NOs: 1 and 2, respectively. It is further contemplated that variants of such p46 sequences can be employed in the compositions of the present invention, as described below.

Zhang et al, described and characterized a p97 adhesin protein of M. hyo [Infect. Immum 63: 1013-1019, 1995]. Additionally, King et al. described a 124 kD protein termed Mhp1 from the P-5722 strain of M. hyo and presented data suggesting that Mhp1 and p97 are the same protein [Vaccine 15:25-35 (1997)]. Such p97 proteins can be employed in the compositions of this invention. In one embodiment, the M. hyo culture supernatant includes the p97 whose corresponding nucleotide and amino acid sequences from the P-5722 strain are set forth in SEQ ID NOs: 3 and 4, respectively. It is further contemplated that variants of such p97 sequences can be employed in the compositions of the present invention, as described below.

The M. hyo culture supernatant may include further M. hyo specific protein antigens such as, but not limited to, proteins of approximately 41 kD (p41), 42 kD (p42), 89 kD (p89), and 65 kD (p65). See, Okada et al., 2000, J. Vet. Med. B 47:527-533 and Kim et al., 1990, Infect. Immun. 58(8):2637-2643. In addition, the M. hyo culture supernatant can include M. hyo specific protein antigens of approximately 102 kD (p102) and 216 kD (p216). See, U.S. Pat. Nos. 6,162,435 and 7,419,806 to Minnion et al.

Any M. hyo strain may be used as a starting material to produce the soluble portion of the M. hyo preparation of the compositions of the present invention. Suitable strains of M. hyo may be obtained from commercial or academic sources, including depositories such as the American Type Culture Collection (ATCC) (Manassas, Va.) and the NRRL Culture Collection (Agricultural Research Service, U.S. Department of Agriculture, Peoria, Ill.). The ATCC alone lists the following six strains of M. hyo for sale: M. hyo ATCC 25095, M. hyo ATCC 25617, M. hyo ATCC 25934, M. hyo ATCC 27714, M. hyo ATCC 27715, and M. hyo ATCC 25934D. A preferred strain of M. hyo for use in the embodiments of this invention is identified as strain P-5722-3, ATCC #5502, deposited on May 30, 1990 pursuant to the accessibility rules required by the U.S. Patent and Trademark Office. In view of the widespread dissemination of the disease, strains may also be obtained by recovering M. hyo from lung secretions or tissue from swine infected with known strains causing *mycoplasmal pneumonia* in swine.

It is understood by those of skill in the art that variants of the M. hyo sequences can be employed in the compositions of the present invention. Such variants could vary by as much as 10-20% in sequence identity and still retain the antigenic characteristics that render it useful in immunogenic compositions. Preferably, the M. hyo variants have at least 80%, preferably at least 85%, more preferably at least 90%, even more preferably at least 95% sequence identify with the full-length genomic sequence of the wild-type M. hyo strain. The antigenic characteristics of an immunological composition can be, for example, estimated by the challenge experiment as provided in the Examples. Moreover, the antigenic characteristic of a modified M. hyo antigen is still retained when the modified antigen confers at least 70%, preferably 80%, more preferably 90% of the protective immunity as compared to the wild-type M. hyo protein.

In one embodiment, M. hyo soluble p46 antigen is included in the compositions of the invention at a final concentration of about 1.5 µg/ml to about 10 µg/ml, preferably at about 2 µg/ml to about 6 µg/ml. It is noted that p46 is the protein used for the M. hyo potency test (see example section below). In another embodiment, the M. hyo antigen can be included in the compositions at a final amount of about 5.5% to about 35% of the M. hyo whole culture protein A-treated supernatant.

The M. hyo soluble preparation of the present invention is both safe and efficacious against M. hyo and is suitable for single dose administration. In addition, Applicants have surprisingly discovered that the M. hyo soluble preparation can be effectively combined with antigens from other pathogens, including PCV2, without immunological interference between the antigens. This makes the M. hyo soluble preparation an effective platform for multivalent vaccines, including the PCV2/M. hyo combination vaccine of this invention. The PCV2 antigen may be given concurrently with the M. hyo composition (i.e., as separate single vaccines), but is preferably combined in a ready-to-use, one-bottle vaccine.

In one embodiment, the immunogenic PCV2/*M. hyo* compositions of the present invention include at least one additional antigen. In one embodiment, the at least one additional antigen is protective against a microorganism that can cause disease in pigs.

In some embodiments, the at least one additional antigen component is protective against bacteria, viruses, or protozoans that are known to infect pigs. Examples of such microorganisms include, but are not limited to, the following: porcine reproductive and respiratory syndrome virus (PRRSV), porcine parvovirus (PPV), *Haemophilus parasuis, Pasteurella multocida, Sireptococcum suis, Staphylococcus hyicus, Actinobacilllus pleuropneumoniae, Bordetella bronehiseptica, Salmonella choleraesuis, Salmonella enteritidis, Erysipelothrix rhusiopathiae, Mycoplama hyorhinis, Mycoplama hyosynoviae*, leptospira bacteria, *Lawsonia intracellularis*, swine influenza virus (SIV), *Escherichia coli* antigen, *Brachyspira hyodysenteriae*, porcine respiratory coronavirus, Porcine Epidemic Diarrhea (PED) virus, rotavirus. Torque term virus (TTV), Porcine Cytomegalovirus, Porcine enteroviruses, Encephalomyocarditis virus, a pathogen causative of Aujesky's Disease. Classical Swine fever (CSF) and a pathogen causative of Swine Transmissable Gastroenteritis, or combinations thereof.

In one embodiment, a PCV2/*M. hyo* combination vaccine according to the present invention is provided as a single-dose, ready-to-use in one bottle vaccine. Such a ready-to-use combination vaccine requires no mixing of separate vaccines, so there is no risk of contamination or additional labor associated with mixing and no requirement to use the mixture within a few hours. Also, a one-bottle PCV2/*M. hyo* combination vaccine cuts waste and refrigerator storage space in half. Furthermore, one-dose administration eliminates the labor associated with administering a second dose to the animal. It is noted that although PCV2/*M. hyo* combination vaccines currently exist, they are provided as either a two-dose, ready-to-use vaccine (Circumvent®PCVM) or as a single-dose, 2-bottle vaccine which requires the simultaneous administration of separate vaccines (e.g., Ingelvac CircoFLEX® and Ingelvac MycoFLEX®). Preferably, the PCV2/*M. hyo* combination according to the present invention would be compatible with other antigens, such as PRRS virus antigen, such that all antigens can be administered in a single-dose.

In some embodiments, the PCV2 antigen component of an PCV2/*M. hyo* combination vaccine is in the form of a chimeric type-1-type 2 circovirus. The chimeric virus includes an inactivated recombinant porcine circovirus type 1 expressing the porcine circovirus type 2 ORF2 protein. Chimeric porcine circoviruses and methods for their preparation are described in WO 03/049703 A2, and also in U.S. Pat. Nos. 7,279,166 and 7,575,752, which are incorporated herein by reference in their entirety.

In one embodiment, the full-length DNA sequence of the genome of the chimeric PCV1-2 virus corresponds to SEQ ID NO: 5. or variants thereof as described below. In another embodiment, the immunogenic. ORF2 capsid gene of the chimeric PCV1-2 virus corresponds to SEQ ID NO: 6. In a further embodiment, the amino acid sequence of the immunogenic ORF2 protein expressed by the chimeric PCV1-2 virus corresponds to SEQ ID NO: 7.

In yet another embodiment, the full-length DNA sequence of the genome of the chimeric PCV1-2 virus corresponds to SEQ ID NO: 8. In one embodiment, the immunogenic ORF2 capsid gene of the chimeric PCV1-2 virus corresponds to SEQ ID NO: 9. In a further embodiment, the amino acid sequence of the immunogenic ORF2 protein expressed by the chimeric PCV1-2 virus corresponds to SEQ ID NO: 10.

However, the PCV2 ORF2 DNA and protein of the chimeric PCV1-2 virus are not limited to the sequences described above since PCV2 ORF2 DNA and protein is a highly conserved domain within PCV2 isolates.

In some embodiments, the PCV2 antigen component of an *M. hyo*/PCV2 combination vaccine is in the form of a recombinant ORF2 protein. In one embodiment, the recombinant ORF2 protein is expressed from a baculovirus vector. Alternatively, other known expression vectors can be used, such as including, but not limited to, parapox vectors.

In one embodiment, the recombinant PCV2 ORF2 protein is that of SEQ ID NO: 11, which is encoded by SEQ ID NO: 12 (GenBank Accession No. AF086834). In another embodiment, the recombinant ORF2 protein is that of SEQ ID NO: 13, which is encoded by SEQ ID NO: 14. In yet another embodiment, the recombinant ORF2 protein corresponds to SEQ ID NO: 15. In still another embodiment, the recombinant PCV2 ORF2 protein corresponds to SEQ ID NO: 7. In a still, further embodiment, the recombinant PCV2 ORF2 protein corresponds to SEQ ID NO: 10.

However, the present invention is not limited to the particular ORF2 DNA and protein sequences described above. Since PCV2 ORF2 DNA and protein is a highly conserved domain within PCV2 isolates, any PCV2 ORF2 is highly likely to be effective as the source of the PCV2 ORF2 DNA and/or polypeptide as used in the chimeric PCV1-2 virus or in the recombinant PCV2 protein.

An example of a suitable PCV2 isolate from which the PCV2 ORF2 DNA and protein sequences can be derived is PCV2 isolate number 40895 (deposited in the ATCC on Dec. 7, 2001 and assigned ATCC Patent Deposit Designation PTA-3914). The genomic (nucleotide) sequence of the PCV2 isolate number 40895 is available under GenBank accession number AF264042. Other examples of suitable PCV2 isolates from which the PCV2 ORF2 DNA and protein sequences can be derived include, but are not limited to, the following: Imp.999, Imp.1010-Stoon, Imp.1011-48121, and Imp.1011-48285. The GenBank accession numbers of the genomic sequences corresponding to these PCV2 isolates are AF055391, AF055392, AF055393 and AF055394, respectively.

In some forms, immunogenic portions of PCV2 ORF2 protein are used as the antigenic component in the composition. For example, truncated and/or substituted forms or fragments of PCV2 ORF2 protein may be employed in the compositions of the present invention.

It is understood by those of skill in the art that variants of the PCV2 sequences can be employed in the compositions of the present invention. Such variants could vary by as much as 10-20% in sequence identity and still retain the antigenic characteristics that render it useful in immunogenic compositions. Preferably, the PCV2 variants have at least 80%, preferably at least 85%, more preferably at least 90%, even more preferably at least 95% sequence identify with the full-length genomic sequence of the wild-type PCV2 isolate. The antigenic characteristics of an immunological composition can be, for example, estimated by the challenge experiment as provided in the Examples. Moreover, the antigenic characteristic of a modified PCV2 antigen is still retained when the modified antigen confers at least 70%, preferably 80%, more preferably 90% of the protective immunity as compared to the wild-type PCV2 ORF2 protein.

The PCV2 antigen component is provided in the immunogenic composition at an antigen inclusion level effective for inducing the desired immune response, namely reducing the incidence of or lessening the severity of clinical signs resulting from PCV2 infection.

In one embodiment, a chimeric PCV1-2 virus is included in the compositions of the invention at a level of at least 1.0≤RP≤5.0, wherein RP is the Relative Potency unit determined by ELISA antigen quantification (in vitro potency test) compared to a reference vaccine. In another embodiment, a chimeric PCV1-2 virus is included in the composition of the invention at a final concentration of about 0.5% to about 5% of 20-times (20×) concentrated bulk PCV1-2 antigen.

In another embodiment, the PCV2 ORF2 recombinant protein is included in the compositions of the invention at a level of at least 0.2 μg antigen/ml of the final immunogenic composition (μg/ml). In a further embodiment, the PCV2 ORF2 recombinant protein inclusion level is from about 0.2 to about 400 μg/ml. In yet another embodiment, the PCV2 ORF2 recombinant protein inclusion level is from about 0.3 to about 200 μg/ml, in a still further embodiment, the PCV2 ORF2 recombinant protein inclusion level is from about 0.35 to about 100 μg/ml. In still another embodiment, the PCV2 ORF2 recombinant protein inclusion level is from about 0.4 to about 50 μg/ml.

In one embodiment, an immunogenic composition of the present invention includes the inventive combination of at least one M. hyo soluble antigen (e.g., two or more) and a porcine circovirus type 2 (PCV2) antigen, as well as a PRRS virus antigen. In another embodiment, the composition elicits a protective immune response in a pig against M. hyo, PCV2 and PRRS virus.

In one embodiment, a PCV2/M. hyo/PRRS combination vaccine is provided as a single-dose, 2-bottle vaccine. For example, in some embodiments, a PCV2/M. hyo combination is provided as a stable liquid composition in a first bottle and a PRRS virus is provided in a lyophilized state in a second bottle. In some embodiments, additional porcine antigens can be added to either the first or the second bottle.

In one embodiment, the PRRS virus component is provided as a lyophilized, genetically modified live virus. Prior to administration, the PCV2/M. hyo liquid from a first bottle can be used to re-hydrate the PRRS virus in a second bottle so that all three antigens can be administered to the animal in a single-dose. It is noted that although PCV2/M. hyo/PRRS combination vaccines currently exist, they are provided as a single-dose, 3-bottle vaccine which requires the simultaneous administration of three separate vaccines (e.g. Ingelvac CircoFLEX®, Ingelvac MycoFLEX® and Ingelvac®PRRS MLV).

The PRRS etiological agent was isolated for the first time in The Netherlands, and named as Lelystad virus. This virus was described in WO 92/21375 (Stichting Centraal Diegeneeskundig Instituut). An isolate of the European PRRS virus was deposited in the Institut Pasteur of Paris, number 1-1102. The North American type was isolated almost simultaneously with the isolation of the European type virus, and is described in WO-93/03760 (Collins et al.) An isolate of the North American type virus was deposited in the American Type Culture Collection (ATCC), number VR-2332.

Different strains have been isolated from both the European and North American virus types. WO 93/07898 (Akzo) describes a European strain, and vaccines derived from it, deposited in CNCM (Institut Pasteur), number 1-1140. Also, WO 93/14196 (Rhone-Merieux) describes a new strain isolated in France, deposited in CNCM (Institut Pasteur), number 1-1153. Furthermore, EP0595436 B1 (Solvay) describes a new North American type strain, more virulent than the one initially described, and vaccines thereof. This strain has been deposited in ATCC, but the deposit number is not detailed in the patent application. In addition, ES2074950 BA (Cyanamid Iberia) and its counterpart GB2282811 B2 describe a so-called "Spanish strain", that is different from other European and North American strains. This "Spanish strain" has been deposited in European Animal Cell Culture Collection (FACCC), number V93070108.

Suitable PRRS virus antigens for use in the PCV2/M. hyo/ PRRS compositions of the present invention include North American PRRS virus isolates. Chinese PRRS virus strains, and European PRRS virus strains, as well as genetically modified versions of such isolates/strains. In one embodiment, the PRRS virus antigen component employed in the compositions according to the present invention is a North American PRRS virus.

In some embodiments, the PRRS virus antigen component employed in the compositions of this invention is the North American PRRS virus isolate designated P129 or a live, genetically modified version thereof. Preferably, the genetically modified PRRS virus is unable to produce a pathogenic infection yet is able to elicit an effective immunoprotective response against, infection by the wild-type PRRS virus.

A genetically modified PRRS virus for use in the compositions of the invention can be produced from an infectious clone. The preparation of an infectious cDNA clone of the North American PRRS virus isolate designated P129 is described in U.S. Pat. No. 6,500,662 which is hereby incorporated fully by reference. The sequence of P129 cDNA is disclosed in Genbank Accession Number AF494042 and in U.S. Pat. No. 6,500,662.

In one embodiment, the nucleotide sequence of a non-virulent form of P129 for use in the compositions of the present invention is represented by SEQ ID NO: 16. However, the present invention is not limited to this sequence. This sequence and the sequences of other non-virulent forms of P129 are described in International Application No. PCT/IB2011/055003, filed Nov. 9, 2011, the contents of which (including any US National Stage filings based on this International Application) are incorporated herein by reference in their entirety. Preferably, the PRRS virus is modified to prevent downregulation of interferon-mediated function.

In other embodiments, the PRRS virus antigen component employed in the compositions of the invention is the PRRS virus isolate designated ISU-55. The ISU-55 isolate was deposited in the American Type Culture Collection (ATCC), under the accession number VR2430. The nucleotide sequence of the ORF2 to ORF5 genes of the ISU-55 isolate is represented by SEQ NO:17. The nucleotide sequence of the ORF6 and ORF7 genes of the ISU-55 isolate is represented by SEQ ID NO: 18.

Another suitable North American PRRS virus isolate which can be used in the compositions is ISU 12, which was deposited in the ATCC under the accession numbers VR2385 [3× plaque purified] and VR2386 [non-plaque purified]. Still other suitable North American PRRS virus isolates which can be employed in the compositions of this invention are the following: ISU-51, ISU-3927, ISU-1894, ISU-22 and ISU-79, which were deposited in the ATCC under the accession numbers VR2498, VR2431, VR2475, VR2429 and VR2474, respectively. Genetically modified versions of any of these ISU isolates can be employed in the compositions of this invention. These ISU isolates and the ISU-55 isolate are described in detail in the following U.S. patents to Paul, et al: U.S. Pat. Nos. 5,695,766, 6,110,467, 6,251.397, 6,251,404, 6,380,376, 6,592,873, 6,773,908, 6,977,078, 7,223,854, 7,764,802, 7,264,957, and 7,517,976, all of which are incorporated herein by reference in their entirety.

In still other embodiments, the PRRS virus antigen component employed in the compositions according to the present invention is the North American type deposited in the American Type Culture Collection (ATCC), number VR-2332 or a genetically modified version thereof. For example, the PRRS virus can be a modified live virus based on the isolate identified as ATCC VR2332, which is employed in INGELVAC® PRRS ATP and INGELVAC® PRRS MLV, from Boehringer Ingelheim Vetmedica, Inc.

In still other embodiments, the PRRS virus antigen component employed in the compositions of the present invention is a European PRRS virus isolate or Lelystad virus or a genetically modified version thereof. An example of a suitable PRRS virus strain is identified as deposit No. I-1102, described above. Nucleotide and amino acid sequences corresponding to the I-1102 deposit are described in U.S. Pat. No. 5,620,691 to Wensvoort et al, which is hereby fully incorporated herein by reference. The preparation of an infectious clone of as European PRRS virus isolate or Lelystad virus is described in U.S. Pat. No. 6,268,199 which is hereby fully incorporated herein by reference. Other examples of suitable PRRS virus isolates include, but are not limited to, those described above. Also, live, genetically modified versions of the PRRS virus isolates can be employed in the compositions of the present invention. An infectious clone can be used to re-create such live genetically modified organisms.

It is understood by those of skill in the art that variants of the PRRS virus sequences can be employed in the compositions of the present invention. Such variants could vary by as much as 10-20% in sequence identity and still retain the antigenic characteristics that render it useful in immunogenic compositions. Preferably, the PRRS virus variants have at least 80%, preferably at least 85%, more preferably at least 90%, even more preferably at least 95% sequence identify with the full-length genomic sequence of the wild-type PPRS virus isolate. The antigenic characteristics of an immunological composition can be, for example, estimated by challenge experiments. Moreover, the antigenic characteristic of a modified PRRS virus antigen is still retained when the modified antigen confers at least 70%, preferably 80%, more preferably 90% of the protective immunity as compared to the wild-type PRRS virus antigen.

In one embodiment, the PRRS virus antigen component is a genetically modified, live virus which is included in the compositions of the invention at a level of at least $2.1 \geq TCID_{50} \geq 5.2$, wherein $TCID_{50}$ is the tissue culture infectious dose 50% determined by antigen quantification (in vitro potency test)

The PCV2 antigen component of the PCV2/*M. hyo*/PRRS compositions of the invention can be in the form of a chimeric type-1-type 2 circovirus, the chimeric virus including an inactivated recombinant porcine circovirus type 1 expressing the porcine circovirus type 2 ORF2 protein. In another embodiment, the PCV2 antigen component of the PCV2/*M. hyo*/ PRRS compositions of the invention is in the form of a recombinant ORF2 protein Suitable PCV2 antigens for use in the PCV2/*M. hyo*/PRRS compositions can be derived from any of the PCV2 isolates described above, as well as other PCV2 isolates. Suitable PCV2 antigens to be employed in the compositions of the invention include, but are not limited to, the PCV2 sequences described above and variants thereof.

Vaccines of the present invention can be formulated following accepted convention to include acceptable carriers for animals, including humans (if applicable), such as standard buffers, stabilizers, diluents, preservatives, and/or solubilizers, and can also be formulated to facilitate sustained release. Diluents include water, saline, dextrose, ethanol, glycerol, and the like. Additives for isotonicity include sodium chloride, dextrose, mannitol, sorbitol, and lactose, among others. Stabilizers include albumin, among others. Other suitable vaccine vehicles and additives, including those that are particularly useful in formulating modified live vaccines, are known or will be apparent to those skilled in the art. See, e.g., Remington's Pharmaceutical Science, 18th ed., 199 Mack Publishing, which is incorporated herein by reference.

Vaccines of the present invention can further comprise one or more additional immunomodulatory components such as, e.g., an adjuvant or cytokine, among others. Types of suitable adjuvants for use in the compositions of the present invention include the following: an oil-in-water adjuvant, a polymer and water adjuvant, a water-in-oil adjuvant, an aluminum hydroxide adjuvant, a vitamin E adjuvant and combinations thereof. Some specific examples of adjuvants include, but are not limited to, complete Freund's adjuvant, incomplete Freund's adjuvant, *Corynebacterium* parvum, *Bacillus* Calmette Guerin, aluminum hydroxide gel, glucan, dextran sulfate, iron oxide, sodium alginate, Bacto-Adjuvant, certain synthetic polymers such as poly amino acids and co-polymers of amino acids, Block copolymer (CytRx, Atlanta, Ga.), QS-21 (Cambridge Biotech Inc., Cambridge Mass.), SAF-M (Chiron, Emeryville Calif.), APHIGEN® adjuvant, saponin, Quil A or other saponin fraction, monophosphoryl lipid A, and Avridine lipid-amine adjuvant (N,N-dioctadecyl-N',N'-bis(2-hydroxyethyl)-propanediamine), "REGRESSIN" (Vetrepharm, Athens, Ga.), paraffin oil, RIBI adjuvant system (Ribi Inc., Hamilton, Mont.), muramyl dipeptide and the like.

Non-limiting examples of oil-in-water emulsions useful in the vaccine of the invention include modified SEAM62 and SEAM 1/2 formulations. Modified SEAM62 is an oil-in-water emulsion containing 5% (v/v) squalene (Sigma), 1% (v/v) SPAN® 85 detergent (ICI Surfactants), 0.7% (v/v) TWEEN® 80 detergent (ICI Surfactants), 2.5% (v/v) ethanol, 200 μg/ml Quil A, 100 μg/ml cholesterol, and 0.5% (v/v) lecithin. Modified SEAM 1/2 is an oil-in-water emulsion comprising 5% (v/v) squalene, 1% (v/v) SPAN® 85 detergent, 0.7% (v/v) Tween 80 detergent, 2.5% (v/v) ethanol, 100 μg/ml Quil A, and 50 μg/ml cholesterol.

Another example of an adjuvant useful in the compositions of the invention is SP-oil. As used in the specification and claims, the term "SP oil" designates an oil emulsion comprising a polyoxyethylene-polyoxypropylene block copolymer, squalane, polyoxyethylene sorbitan monooleate and a buffered salt solution. Polyoxyethylene-polyoxypropylene block copolymers are surfactants that aid in suspending solid and liquid components. These surfactants are commercially available as polymers under the trade name Plutonic®. The preferred surfactant is poloxamer 401 which is commercially available under the trade name Plutonic® L-121. In general, the SP oil emulsion is an immunostimulating adjuvant mixture which will comprise about 1 to 3% vol/vol of block copolymer, about 2 to 6% vol/vol of squalane, more particularly about 3 to 6% of squalane, and about 0.1 to 0.5% vol/vol of polyoxyethylene sorbitan monooleate, with the remainder being a buffered salt solution. In one embodiment, the SP-oil emulsion is present in the final composition in v/v amounts of about 1% to 25%, preferably about 2% to 15%, more preferably about 5% to 12% v/v.

Yet another example of a suitable adjuvant for use in the compositions of the invention is AMPHIGEN™ adjuvant which consists of de-oiled lecithin dissolved in an oil, usually light liquid paraffin.

Other examples of adjuvants useful in the compositions of the invention are the following proprietary adjuvants: Microsol Diluvac Forte® duel emulsion adjuvant system, Emunade adjuvant, and Xsolve adjuvant. Both the Emunade and Xsolve adjuvants are emulsions of light mineral oil in water, but Emunade also contains alhydrogel, and d,l-α-tocopheryl acetate is part of the XSolve adjuvant. A still further example of a suitable adjuvant for use in the compositions of the invention is ImpranFLEX™ adjuvant (a water-in-oil adjuvant). A still further example of a suitable adjuvant is a Carbomer (Carbopol®) based adjuvant. Preferred Carbopol® adjuvants include Carbopol® 934 polymer and Carbopol®941 polymer.

In one embodiment, the adjuvant or adjuvant mixture is added in an amount of about 100 µg to about 10 mg per dose. In another embodiment, the adjuvant/adjuvant mixture is added in an amount of about 200 µg to about 5 mg per dose. In yet another embodiment, the adjuvant/adjuvant mixture is added in an amount of about 300 µg to about 1 mg/dose.

The adjuvant or adjuvant mixture is typically present in the vaccine composition of the invention in v/v amounts of about 1% to 25%, preferably about 2% to 15%, more preferably about 5% to 12% v/v.

Other "immunomodulators" that can be included in the vaccine include, e.g., one or more interleukins, interferons, or other known cytokines. In one embodiment, the adjuvant may be a cyclodextrin derivative or a polyanionic polymer, such as those described in U.S. Pat. Nos. 6,165,995 and 6,610,310, respectively.

A further aspect relates to a method for preparing an immunogenic composition according to the present invention. This method comprises i) culturing M. hyo in a suitable media over periods ranging from 18-144 hours; ii) subsequently inactivating the M. hyo culture; iii) harvesting the inactivated culture fluid, wherein the inactivated culture fluid comprises an M. hyo whole cell preparation comprising both a soluble liquid fraction and insoluble cellular material; iv) separating the soluble liquid fraction from the insoluble cellular material; v) substantially removing both IgG and antigen/immunoglobulin immunocomplexes from the separated soluble liquid fraction to form a soluble portion of the M. hyo whole cell preparation; and vi) subsequently combining the soluble portion of the M. hyo whole cell preparation with a PCV2 antigen.

An example of a suitable media for culturing M. hyo is PPLO Broth (Mycoplasma Broth Base), which when supplemented with nutritive enrichments, is used for isolating and cultivating Mycoplasma.

In some embodiments, the culture of M. hyo is grown until late log phase growth, after which the culture is inactivated. In some other embodiments, the culture is inactivated by raising the pH (e.g., to about 7.8). This occurs by exposing the production culture to an inactivation agent, such as binary ethyleneimine (BEI). The BEI is generated in situ during incubation of L-bromoethylamine hydrobromide (BEA) in the production culture. Subsequently, the pH of the inactivated culture is neutralized, such as by adding an equivalent amount of an agent that neutralizes the inactivation agent within the solution. In some embodiments, the inactivation agent is BEI and the neutralization agent is sodium thiosulfate. In one embodiment, the pH of the inactivated culture is adjusted to about 7.4 by adding sodium thiosulfate.

In some embodiments, the soluble liquid fraction of the M. hyo whole cell preparation is separated from the insoluble cellular material using conventional methods. In one embodiment, this separation is by a filtration step. In another embodiment, this separation is by a centrifugation step. In yet another embodiment, the separation is by a precipitation step.

In one embodiment, the soluble liquid fraction of an inactivated, neutralized M. hyo whole cell preparation is treated with Protein A resin to substantially remove both the IgG and antigen/immunoglobulin immunocomplexes therein. In other embodiments, Protein G resin can be used to substantially remove both the IgG and antigen/immunoglobulin immunocomplexes contained in the soluble liquid fraction. Methods for removing both IgG and antigen/immunoglobulin immunocomplexes with either Protein A or Protein G resins are well known in the art.

According to a further aspect, the method for preparing a multivalent immunogenic composition according to the present invention comprises preparing the soluble M. hyo antigen as described above and mixing this with a PCV2 antigen, a suitable adjuvant, and one or more pharmaceutically-acceptable carriers. This method optionally includes adding at least one additional porcine antigen, such as, but not limited to, PRRS virus antigen as described above.

A further aspect of the present invention relates to a kit. A "kit" refers to a plurality of components which are grouped together. In one embodiment, a kit according to the present invention includes a bottle (or other suitable receptable) comprising an immunogenic composition. This immunogenic composition includes both a PCV2 antigen, and the soluble portion of a Mycoplasma hyopneumoniae (M. hyo) whole cell preparation, wherein the soluble portion of the M. hyo preparation is substantially free of both (i) IgG and (ii) antigen/immunoglobulin immunocomplexes. Optionally, the kit can further include an instruction manual. The instruction manual includes the information to administer the immunogenic composition.

In some embodiments, the PCV2/M. hyo combination in the bottle of the kit is provided as a ready-to-use liquid composition. In other embodiments, the kit includes a second bottle comprising PRRS virus antigen. In some embodiments, the PRRS virus antigen is in the form of a genetically modified, live virus which is provided in a lyophilized state. In such instances, the instruction manual will include the directions for re-hydrating the PRRS virus component with the liquid contents from bottle containing the PCV2/M. hyo combination. The instruction manual will also include the information to administer the resultant PCV2/M. hyo/PRRS trivalent formulation(s).

In some embodiments, an immunogenic composition according to this invention is administered to pigs having maternally derived antibodies against M. hyo. In other embodiments, an immunogenic composition of the present invention is administered to pigs having maternally derived antibodies against both M. hyo and PCV2.

In some embodiments, a multivalent immunogenic composition according to the present invention is administered to a piglet aged 3 weeks or older. However, it is contemplated that a multivalent vaccine composition according to the invention may also be used to re-vaccinate gilts pre-breeding. As is known in the art, a gilt is a female pig that has never been pregnant. Vaccinated gills will pass maternally derived antibodies onto their suckling newborns via colostrum.

It is further contemplated that a multivalent vaccine according to the invention can be used to annually re-vaccinate breeding herds. Preferably, a multivalent vaccine according to the present invention is administered to pigs (e.g., piglets or gilts) in one dose. In one embodiment, a multivalent vaccine according to the present invention does not require mixing of separate monovalent vaccines prior to administration. i.e., it is provided as a ready-to-use PCV2/M. hyo formulation contained in one bottle. In another embodiment, a multivalent formulation requires mixing of a divalent vaccine according to the present invention contained in a first bottle with a monovalent vaccine contained in a second bottle. In one embodiment, the monovalent vaccine contained in the second bottle includes PRRS virus antigen. Optionally, additional antigens can be added to either of these bottles.

In some embodiments, the onset of immunity is from 2-3 weeks post-vaccination with a multivalent vaccine composition according to the present invention. In other embodiments, the duration of immunity is about 17-23 weeks post-vaccination with a multivalent vaccine composition according to the present invention.

The following examples set forth preferred materials and procedures in accordance with the present invention. However, it is to be understood that these examples are provided by way of illustration only, and nothing therein should be deemed a limitation upon the overall scope of the invention.

EXAMPLES

Example 1

*Mycoplasma Hyopneumoniae* Production Methods for PCV2 Combinable *M. hyo* Antigen

*M. hyo* Fermentation and Inactivation

Media for seed scale and antigen production was prepared as follows. Porcine heart derived Pleuropenumonia-like Organism (PPLO) Broth (BD Biosciences catalog No. 21498) was made per manufacturer's directions (i.e., 21 g/l) and yeast extract solution was made at 21 g/L in USP. Yeast extract solution was then added to the PPLO at 6.25% and the mixture was sterilized by heating to 121° C. for ≥30 minutes. Cysteine hydrochloride was prepared at 90 g/L and filter sterilized. Dextrose solution was made by adding 450 g of dextrose per liter of USP water followed by heat sterilization. To prepare the final medium, porcine serum was added to the base medium at 10% followed by cysteine at 0.01% and dextrose at 1.0%. The medium was inoculated with a 10% v:v of a log phase culture of *M. hyopeumoniae* (strain P-5722-3). The culture was held at 37° C. and pH and dO were maintained at 7.0 and 25%, respectively. At late log phase growth, the culture was inactivated was inactivated by binary ethylenimine (BEI), an aziridine compound, produced from 2-bromoethylamine hydrobromide. Specifically, the inactivation occurred by raising the pit to 7.8 by adding 2-bromoethylaminehydrobromide (BEA) to a final concentration of 4 mM and incubating for 24 hours. The BEI was neutralized by addition of sodium thiosulfate at a 1:1 molar ratio followed by additional 24 hour incubation. The inactivated culture fluid was held at 2-8° C. until further processing.

Example 2

Chimeric Porcine Circovirus (cPCV)1-2 Production Methods

The cPCV1-2 was constructed by cloning the immunogenic capsid gene of the pathogenic porcine circovirus type 2 (PCV2) into the genomic backbone of the nonpathogenic porcine circovirus type 1 (PCV1). The procedure for construction of the chimeric DNA clone is described, for example, in U.S. Pat. No. 7,279,166, which is incorporated herein by reference in its entirety. An infectious stock of the chimeric virus was acquired from Dr. X. J. Meng, Virginia Polytechnic Institute and State University, Blacksburg, Va., and was used to infect Porcine Kidney (PK)-15 cells grown in Minimum Essential Medium (MEM) supplemented with 0.05% lactalbumin hydrolysate (LAM, 30 µg/mL gentamicin sulfate, and 5% fetal bovine serum. The resulting cPCV1-2 infected PK-15 cells were further expanded by serial passing four more times using the same growth medium except with 2-3% fetal bovine serum. The fifth passage was frozen, thawed and filtered, and the resulting lysates were used to prepare a pre-master seed and subsequent master seed.

The medium which was used for producing virus seeds was the same as that used in producing virus stock. For the growth medium, MEM, OptiMEM, or equivalent is the basal medium which can be used for planting the PK-15 cell line for outgrowth. The growth medium can be supplemented with up to 10% bovine serum, up to 0.5% lactalbumin hydrolysate, up to 0.5% bovine serum albumin, and up to 30 µg/mL gentamicin. For the virus propagation medium, MEM, OptiMEM, or equivalent is used. The virus propagation medium can be supplemented with up to 0.5% lactalbumin hydrolysate, up to 2% bovine serum, up to 0.5% bovine serum albumin, and up to 30 µg/mL gentamicin. Up to 5 g/L glucose and up to 5 mmol/L L-glutamine can be added to the growth medium and/or the virus propagation medium as required to sustain the cells.

The cPCV1-2 master seed virus are added to a cell suspension of PK-15 cells and adsorbed for up to 3 hours. Seed virus is diluted in growth basal medium to provide a multiplicity of infection (MOI) of 0.1-0.0001.

Cultures of PK-15 cells are initially inoculated with working seed virus at the time of cell planting, or when cells reach approximately 20% to 50% confluency. This initial passage may be referred as "One-Step infection Method" for the production of antigen stock, or may be further used for serial passages. For serial passages, the cPCV1-2 infected PK-15 cells are further expanded up to passage 7 by serial splits at the ratio of 1:5-20 for virus propagation. Culture medium containing an infected cell suspension from the previous passage serves as seed material for the next passage. The cPCV1-2 infected cells are incubated for three (3) to 14 days for each passage at 36±2° C. when cells reach ≥90% confluency. The cPCV1-2 virus causes observable cytopathic changes during viral replication. At harvest, rounding of cells and considerable floating debris is observed. Cultures are also observed for visual evidence of bacterial or fungal contamination. The incubation time between harvests for the cPCV antigen is provided in Table 1 below:

TABLE 1

Minimum and Maximum Times for Harvesting cPCV Antigen

| Method | Minimum/ Maximum Time | Temperature Range |
|---|---|---|
| One-Step Infection | 5 to 16 days | 36 ± 2° C. |
| Serial Passage (MSV + 3 to MSV + 7) | 16 to 36 Days | 36 ± 2° C. |

The cPCV1-2 culture fluids are harvested into sterile vessels and are sampled for *mycoplasma* testing using known methods. Multiple harvests may be conducted from roller bottles, bioreactors and perfusion vessels.

Prior to inactivation of the harvested cPCV1-2 virus, one or more antigen lots may be concentrated (e.g., up to 60×) by ultrafiltration. The concentrates may be washed with balanced salt solution to reduce serum proteins.

The method of inactivation, attenuation, or detoxification of the cPCV1-2 virus will now be described. After cPCV antigen concentration, Beta-propiolactone (BPL) is added to the pooled cPCV1-2 viral material to obtain an approximate concentration of 0.2% v/v. The pooled viral fluids are then agitated for a minimum of 15 minutes and then the inactivating bulk antigen thuds are transferred to a second sterile vessel. The transferred antiven fluids are maintained at 2-7° C., with constant agitation, for a minimum of 24 hours. After a minimum of 24 hours, a second addition of 0.2% v/v of BPL is added to the pooled suspension. The contents are subsequently agitated, transferred to a third vessel, and maintained at 2-7° C., with constant agitation, for an additional time of not less than 84 hours. In general, the total inactivation time is not less than 108 hours and not more than 120 hours. The inactivation method is summarized in Table 2 below.

TABLE 2

Inactivation Method

| Inactivant | Final Concentration | Temp. Range | Time-Hours (Min/Max) |
|---|---|---|---|
| Beta-propiolactone (BPL) | 0.4% v/v(2 × 0.2% v/v additions) | 2-7° C. (w/Agitation) | 108-120 |

The inactivation is terminated by the addition of a final concentration of not more than 0.1 M solution of sodium thiosulfate. The pH of the inactivated antigen stock is adjusted to about 6.8 using NaOH or HCl. Following inactivation, a representative sample is taken from the pool and tested for completion of inactivation. The inactivated cPCV1-2 antigen product is standardized to a meet a target of greater than 1.0 RP as measured via potency ELISA.

Example 3

Down Stream Processing of M. hyo Antigens and Analytical Testing of these Processed Antigens Down Stream Processing of M. hyo Antigens:

Inactivated fermentation fluid (prepared as described above in Example 1) was treated for each indicated group as follows. These processed M. hyo antigens were employed in Example 4 below.

T02: (Whole Bulk) not processed.

T03: (10×UF concentrated) Concentrated via tangential flow filtration via a 100 KDa molecular weight cutoff membrane (hollow fiber), Final volume reduction was equal to 10×.

T04& T05: (10×UF concentrated & centrifuged) Concentrated mycoplasma cells (from T03) were collected and washed one time with PBS via centrifugation at ~20,000×g (Sorvall model RC5B).

T06 & T07: (10× centrifuged) Inactivated fermentation fluid was centrifuged at ~20,000×g (Sorvali RC5B) and washed one time by resuspending the cells in PBS followed by an additional centrifugation. Final volume reduction was equal to 10×.

T08: (10× centrifuged & Heated) Mycoplasma cells were concentrated and washed per T06 and heated to 65° C. for 10 minutes.

T09: (Cell-free supernatant) Supernatant collected from the first centrifugation as described for TO was filter sterilized through a 0.2 micron filter (Nalgene).

T10: (Cell-free supernatant-Protein-A treated) Sterile supernatant (prepared per T09) was mixed with Protein A resin (Protein A Sepharose, Pharmacia Inc) at a 10:1 volume ratio for 4 hours. Resin was removed sterile filtration and filtered fluid was stored at 2-8° C. This process uses post-fermentation "downstream" protein A treatment to remove antibodies and immunocomplexes. Although the present invention does not preclude upstream protein A treatment, the present inventors have found that in the case of M. hyo, upstream protein A treatment of the growth media led to p46 results which were lower and inconsistent as compared to untreated media (data not shown).

Analytical Testing of M. hyo Downstream Processed Antigens

The downstream processed M. hyo antigens preparations (prepared as described above) were tested for the recovery of M. hyo specific p46 antigen, and the presence of PCV2 antibody. In addition, these M. hyo antigen preparations were tested for the presence of Torque Teno Virus (TTV), including genotype 1 (g1TTV) and genotype 2 (g2TTV). The results are presented below in Table 3.

TABLE 3

Characterization of M.hyo Downstream Processed Antigens

| Treatment | Bulk M.Hyo p46 RU/mL | PCV2 ab S/P ratio | qPCR DNA g1TTV | qPCR DNA g2TTV |
|---|---|---|---|---|
| Whole bulk | 809 | 0.248 | 1.00E+03 | 1.78E+03 |
| 10× UF concentrated | 6666 | 0.819 | 1.00E+03 | 9.94E+03 |
| 10× UF conc. + Centrifuge | 614 | 0.019 | 0 | 0 |
| 10× Centrifuged | 763 | −0.015 | 1.90E+02 | 1.91E+02 |
| 10× Centrifuged + Heated | 690 | −0.012 | 0 | 2.07E+02 |
| Cell-free supe | 719 | 0.242 | 4.20E+02 | 3.23E+03 |
| Cell-free supe (Prot A) | 826 | −0.014 | 0 | 2.06E+03 |

With reference to Table 3 above, recovery of the M. hyo-specific p46 antigen was demonstrated for each of the M. hyo downstream processed antigen preparations. In addition, the following treatments successfully removed PCV2 antibody; 10×UF concentrated & centrifuged, 10× centrifuged, 10× centriftiged & heated and Cell-free supernatant (Protein-A treated). With respect to TTV, the following treatments successfully removed g1TTV: 10×UF concentrated & centrifuged, 10× centrifuged & heated, and Cell-free supernatant (Protein-A treated). Only the treatment designated 10×UF concentrated & centrifuged removed g2TTV. Torque teno virus isolates, including genotypes 1 and 2 are described in US20110150913, which is incorporated herein by reference in its entirety.

Since it is known in the art that Protein A binds IgG, it is understood by those of ordinary skill in the art that not only PCV2 antibody, but other swine antibodies, including PRRS antibody, HPS antibody, and SIV antibody will be effectively removed by the Protein-A treatment. This makes the Cell-free Protein-A treated M. hyo supernatant of this invention compatible not only with PCV2 antigen, but also with other porcine antigens due to the lack of immunological interference between the antigens. Additionally, the removal of the non-protective cell debris and removal of the immunoglobulin and antigen/immunoglobulin complexes is reasonably expected to make a safer vaccine.

Example 4

Preparation of M. hyo Experimental Vaccine Formulations

All experimental M. hyo vaccines were formulated with a final concentration of 5% Amphigen adjuvant. In addition, all vaccines were standardized with a p46 ELISA and preserved with thimerosol. The experimental vaccine formulations were prepared with *M. hyo* antigens processed according to treatments T02-T10 above. In addition, Treatment T01 corresponded to a placebo (no *M. hyo* antigen, only 5% Amphigen adjuvant) whereas Treatment T11 is a positive control corresponding to an expired bacterin-based *M. hyo* vaccine (RespiSure-ONE®, Pfizer Animal Health). These formulations are described in Table 4 below.

TABLE 4

*M.hyo* Experimental Vaccine Formulations

| Treatment | IVP Serial* | Target p46 units/ds | M Hyo antigen (mL) | Adjuvant (mL) | Formulation Vol. (mL) |
|---|---|---|---|---|---|
| T01 | 123639 (Placebo) | 5% Amphigen only, No Antigen | | | |
| T02 | L100211A | 452 | 279.36 | 250 | 1000 |
| T03 | L100211B | 452 | 6.78 | 50 | 200 |
| T04 | L100211C | 452 | 73.62 | 50 | 200 |
| T05 | L100211D | 816 | 132.90 | 50 | 200 |
| T06 | L100211E | 452 | 59.24 | 50 | 200 |
| T07 | L100211F | 816 | 106.95 | 50 | 200 |
| T08 | L100211G | 452 | 65.51 | 50 | 200 |

TABLE 4-continued

*M.hyo* Experimental Vaccine Formulations

| Treatment | IVP Serial* | Target p46 units/ds | M Hyo antigen (mL) | Adjuvant (mL) | Formulation Vol. (mL) |
|---|---|---|---|---|---|
| T09 | L100211H | 452 | 62.87 | 50 | 200 |
| T10 | L100211J | 452 | 54.72 | 50 | 200 |
| T11 | A827870 | Expired "RespiSure" vaccine | | | |

*Investigational Veterinary Product (IVP) Serial

Example 5

Evaluation of the In Vivo Efficacy of *M. hyo* Vaccines with *M. hyo* Antigens from Different Downstream Processes This study was conducted to evaluate the in vivo efficacy of *Mycoplasma hyopnelononiae* (*M. hyo*) vaccines with *M. hyo* antigens from different downstream processes (DSP). Pigs at 3 weeks of age were intramuscularly inoculated with a single dose of the different vaccine formulations described in Table 4 above. Sixteen animals were included in each of the treatment groups. Animals were challenged 21 days after vaccination with a virulent *M. hyo* field isolate. Animals were necropsied 28 days after challenge and the lungs were removed and scored for consolidation consistent with *M. hyo* infection. The primary criterion for protection against *M. hyo* challenge was lung consolidation scores. It is generally accepted that there is a relationship between the size of the lung lesions caused by enzootic pneumonia and an adverse effect on growth rate. Table 5 below contains the lung lesion scores for the respective treatment groups. Statistical significance was determined by a Mixed Model Analysis of lung scores for each group.

TABLE 5

Lung Lesion Results

| Treatment | Description | p46 RP Target/Observed | % Lung Lesions Back Transformed LS Means | Range % Lung with Lesions | Contrast | p-value | Significant |
|---|---|---|---|---|---|---|---|
| T01 | Placebo (5% Amphigen) | N/A | 11.7 | 1.2-44.3 | N/A | N/A | N/A |
| T02 | Whole bulk | 13/15.6 | 1.2 | 0.1-18.5 | T01 vs 02 | 0 | Yes |
| T03 | Whole bulk UF 10x | 13/11.9 | 0.3 | 0.0-2.8 | T01 vs 03 | 0 | Yes |
| T04 | UF 10x + Centrifuged | 13/28.1 | 5.9 | 0.0-40.5 | T01 vs 04 | 0.1589 | No |
| T05 | UF 10x + Centrifuged | 24/48.2 | 3.7 | 0.0-42.3 | T01 vs T05 | 0.0309 | Yes |
| T06 | 10x Centrifuged | 13/30.4 | 4.7 | 0.0-23.6 | T01 vs 06 | 0.0388 | Yes |
| T07 | 10x Centrifuged | 24/57.4 | 4.6 | 0.3-37.3 | T01 vs T07 | 0.0323 | Yes |
| T08 | 10x Centrifuged + Heat | 13/17.7 | 4.5 | 0.3-21.7 | T01 vs T08 | 0.0137 | Yes |
| T09 | Supernatant (no cells) | 13/14.1 | 1.4 | 0.0-33.0 | T01 vs T09 | 0.0004 | Yes |
| T10 | Supernatant + Prot A | 13/12.1 | 3.1 | 0.0-25.8 | T01 vs T10 | 0.0094 | Yes |
| T11 | Expired RSO | 13/12.5 | 2.2 | 0.1-32.1 | T01 vs T11 | 0.0009 | Yes |

With reference to Table 5 above, the results with *M. hyo* antigens from different downstream processes indicated that all experimental vaccines except T04 significantly differed from the placebo. These *M. hyo* lesion results are depicted graphically in FIG. 1. As shown in FIG. 1, T04 gave unacceptable results. All other treatments differed significantly from the placebo (T01). The lung consolidation scores indicated that T02, T03 and T09-T11 gave the most efficacious protection against *M. hyo* challenge.

The p46 relative potency of the experimental vaccines was assessed by using a double antibody sandwich enzyme-linked immunosorbent assay (DAS ELBA). The p46 DAS ELISA results presented in Table 5 above indicate that all the experimental vaccines exceeded the target potency. In addition, the p46 relative potency was either maintained or increased during storage of the vaccines over a one-month period (data not shown). A perceived increase in potency over time was observed in centrifuged antigens with the exception of those antigens that were subjected to heat. While not wishing to be bound by any one theory, it is likely that cell "carcasses" are breaking up over time and released more of the membrane bound p46 antigen in the case of the centrifuged antigens.

Example 6

Evaluation of the Compatibility of the Experimental M. hyo Vaccines with PCV2 Antigen This study was conducted to evaluate the compatibility of the M. hyo experimental vaccines with M. hyo antigens from different downstream processes with PCV2 antigen. The M. hyo experimental vaccine formulations are described in Tables 4 and 5 above. The Observed p46 relative potencies for these vaccines are described in Table 5 above. These M. hyo experimental vaccines were each combined with PCV2 antigen. In this example, the PCV2 antigen was a killed PCV Type 1-Type 2 chimeric virus (Fostera PCV) prepared as described above in Example 2. The chimeric virus was included in the compositions at an initial level of about 1.6≤RP, wherein the RP is the Relative Potency unit determined by PCV2 ELISA antigen quantification (in vitro potency test) compared to an efficacious reference vaccine.

Figure 2:
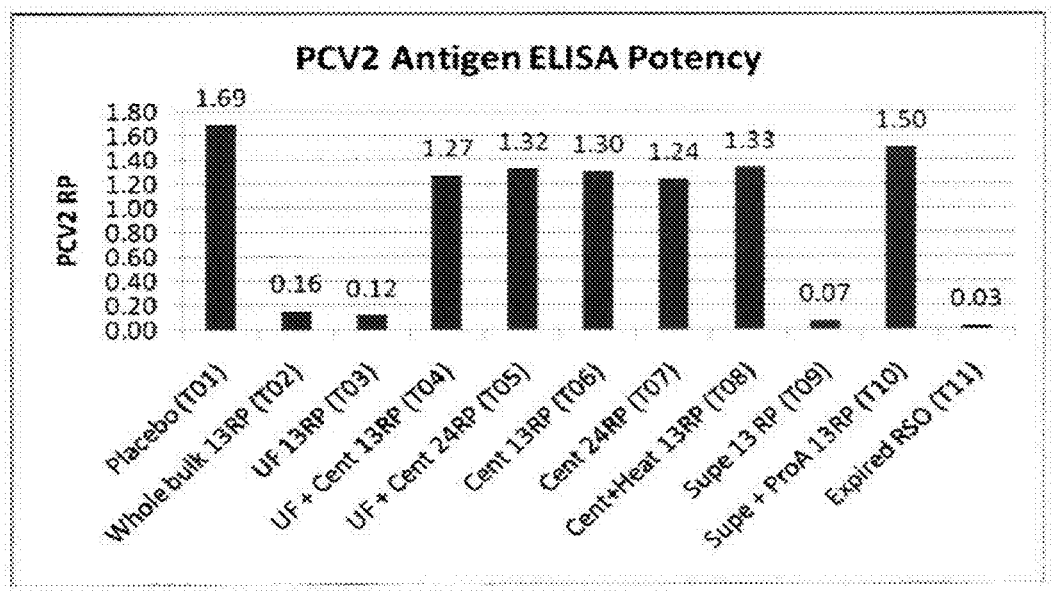
FIG. 2 is a graph showing the PCV2 antigen potency results (PCV2 antigen ELISA) of *M. hyo* vaccines in combination with killed PCV Type1-Type2 chimeric virus. The chimeric virus was included in the compositions at an initial level of about 1.6≤RP. The status of each sample is expressed as relative potency (RP).

The experimental M. hyo/PCV2 combination formulations were evaluated by PCV2 ELBA. The results are presented in FIG. 2. As shown in FIG. 2, only the M. hyo antigen preparations from the following downstream processes were compatible with the PCV2 antigen: Ultrafiltration & Centrifugation (T04 & T05), Centrifugation (T06 & T07). Centrifugation plus heat (T08) and Protein A-treated Supernatant (T10). Of these, the M. hyo Protein A-treated supernatant was the most compatible with PCV2 antigen when compared to the placebo control which included the chimeric virus and Amphigen adjuvant, but no M. hyo antigen. The level of chimeric PCV virus in the Protein-A treated supernatant was 1.5 RP as compared to 1.69 RP for the placebo. It was therefore concluded that there is no or minimal immunological interference between the Protein-A treated M. hyo soluble antigen preparation and PCV2 antigen of the chimeric virus.

The in vivo efficacy of the Protein-A treated M. hyo supernatant demonstrated in Example 5 above together with the results described in the present example indicated that the Protein-A treated supernatant was a potentially effective platform for M. hyo-PCV2 combinations.

Example 7

Evaluation f PCV2 Efficacy of 1-Bottle PCV2/M. hyo Combination Vaccine in Different Adjuvant Formulations This study was designed to evaluate the PCV2 efficacy in a 1-bottle PCV2/M. hyo combination vaccine in different adjuvant formulations. In this example, the PCV2 antigen was a killed PCV Type 1-Type 2 chimeric virus (Fostera PCV). The chimeric virus was combined with an M. hyo soluble antigen preparation that was substantially free of IgG (i.e., Protein A-treated supernatant).
Processing of Fluids:
Inactivated M. hyo fermentation fluid (described above in Example 1) was treated for each indicated group as follows.
T02-T04: Whole fermentation fluid containing live M. hyopneumoniae cells (described above) was centrifuged at ~20,000×g (Sorvall RC5B) and the supernatant collected and sterilized through a 0.2 µM filter, rProtein A Sepharose (part number 17-5199-03, GE Healthcare) was packed into a 1 L chromatography column. After removal of the storage buffer and treatment with 2 column volumes of 1 M acetic acid, the resin was equilibrated with 5 column volumes of 50 mM NaPO$_4$/1M NaCl buffer, pH 7.04. Approximately 2 liters of the clarified/filtered M. hyopneumoniae antigen containing fluids were passed through the Protein A resin at a flow rate of 100 cm/hr. The flow through was collected and sterilized via 0.2 µM filter.

T05: This is a positive control corresponding to a Fostera PCV-like formulation (no M. hyo antigen). The level of the chimeric virus in this Fostera PCV-like formulation was approximately at Minimum Immunizing Dose (MID) formulation levels. The chimeric virus was included in the PCV2/M. hyo experimental vaccines at similar fbrmulation levels.

All experimental PCV2/M. hyo vaccines were formulated with different adjuvant formulations. The experimental vaccine formulations were prepared with M. hyo antigens processed according to treatments T02-T04 above. In addition. Treatment T01 corresponded to a placebo (sterile saline).

All vaccines were standardized with a p46 ELISA and preserved with thimerosol.

These experimental formulations are described in Table 6 below, wherein the symbol * indicates the M. hyo antigen from global M. hyo seed, Protein A treated supernatant and the symbol ** indicates Investigational Veterinary Product (IVP) serial.

TABLE 6

PCV2/M.hyo Experimental Vaccine Formulations Used for PCV2 Efficacy Study

| Treatment | IVP Serial** | PCV1-2 Ag | M Hyo* Ag | Adjuvant | Other |
|---|---|---|---|---|---|
| T01 | 87-244-DK (Placebo) | | NA | | Sterile Saline |
| T02 | L0411RK08 | 1.6 RP | 7.5 RP | 10% SP Oil | NA |
| T03 | L0411RK09 | | | 5% Amphigen | |
| T04 | L0611RK03 | | | 5% Amphigen + 5% SLCD | |
| T05 | L0611RK04 | | NA | 20% SLCD | |

Pigs at 3 weeks of age were intramuscularly inoculated with a single dose of the different vaccine formulations described in Table 6 above. Sixteen animals were included in each of the treatment groups. Animals were challenged 21 days after vaccination with a virulent PCV2 field isolate.

Figure 3:
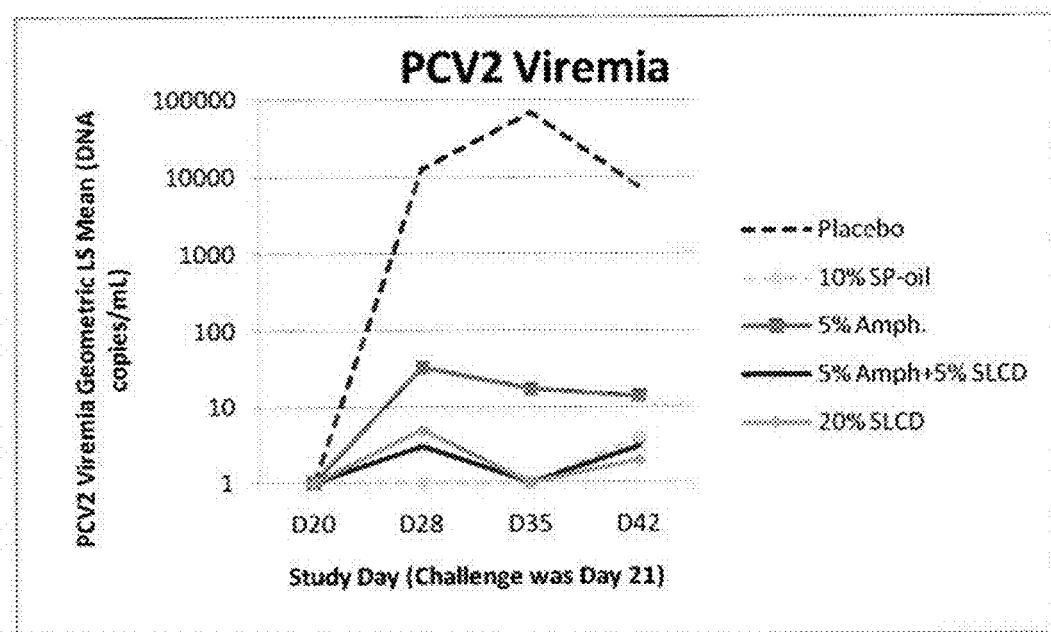
FIG. 3 is a graph showing the PCV2 viremia results (PCV2 Quantitative PCR) observed with PCV/*M. hyo* vaccine formulations employing different adjuvant platforms.

FIG. 3 is a graph showing the PCV2 viremia results (PCV2 Quantitative PCR) observed with the different adjuvant platforms. It is noted that PCV2 viremia was used as the primary efficacy variable. The PCV2 viremia results are presented as DNA copies/ml. As shown in FIG. 3, all treatments had significantly less viremia compared to the placebo on days 28, 35 and 42 (challenge was day 21). The 10% SP-oil adjuvant had significantly less viremia compared to 5% Amphigen at Days 28 and 35. The 5% Amphigen plus 5% SLCD adjuvant had significantly less viremia compared to 5% Amphigen at Days 28 and 35. The 20% SLCD adjuvant platform had significantly less viremia compared to 5% Amphigen at Days 28, 35 and 42.

PCV2 Serology, PCV2 fecal shed, PCV2 nasal shed, Cell Mediated Immune (CMI) responses, lymphoid depletion, and Immunohistochemistry (IHC) were also monitored as secondary efficacy variables. These results will now be described below.

Figure 4:
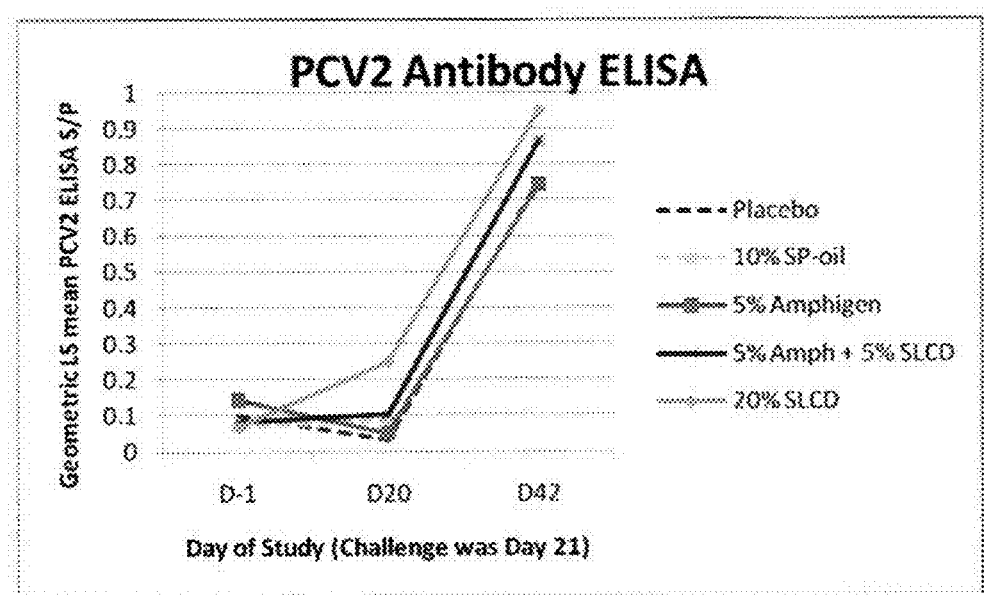
FIG. 4 is a graph showing the PCV2 antibody ELISA (S/P) serological, results observed with PCV/*M. hyo* vaccine formulations employing different adjuvant platforms on days 1, 20, and 42 of challenge.

FIG. 4 is a graph showing the PCV2 ELISA results on days 1, 20 and 42 of the study (challenge was day 21). The status of each sample was expressed as a sample to positive ratio (S/P). As shown in FIG. 4, 20% SLCD was the only treatment which was significantly different from the placebo (T01) at both day 20 and day 42. Also, 5% Amphigen was the only treatment not significantly different from the placebo at day 20.

Figure 5:
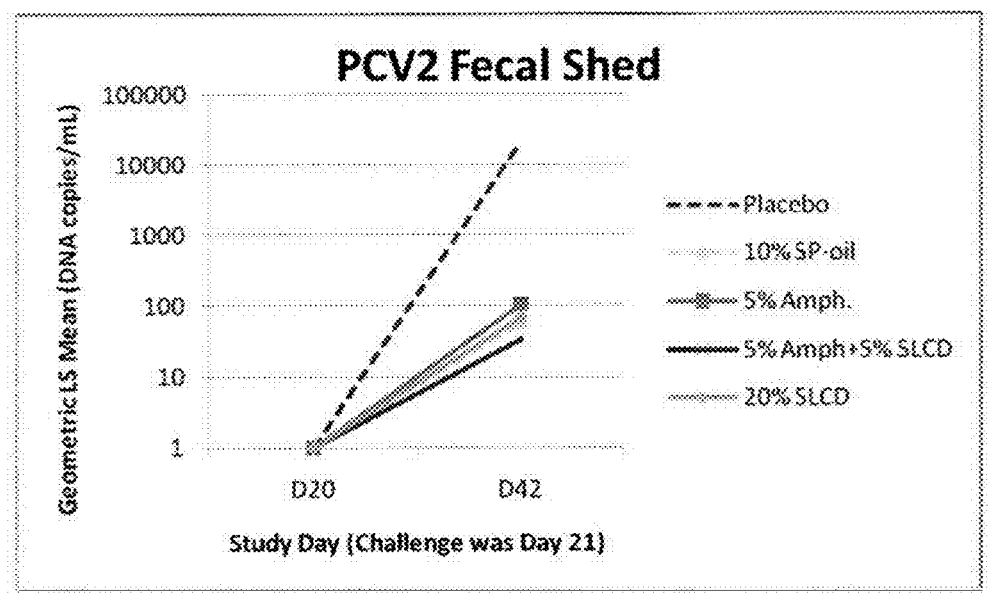
FIG. 5 is a graph showing the PCV2 fecal shed obtained with the T02-T04 treatments described in Example 7 vs. a placebo (T01). The results are expressed as PCV2 DNA copies/ml.

FIG. 5 is a graph showing the PCV2 fecal shed obtained with the T02-T04 treatments vs. the placebo (T01). These results are expressed as PCV2 DNA copies/ml. The results in FIG. 5 indicate that all treatments had significantly less fecal shed when compared to the placebo at day 42. In addition, 5% Amphigen & 5% SLCD (T04) had significantly less fecal shed as compared to 5% Amphigen (T03) at day 42. No other treatment differences were noted.

Figure 6:
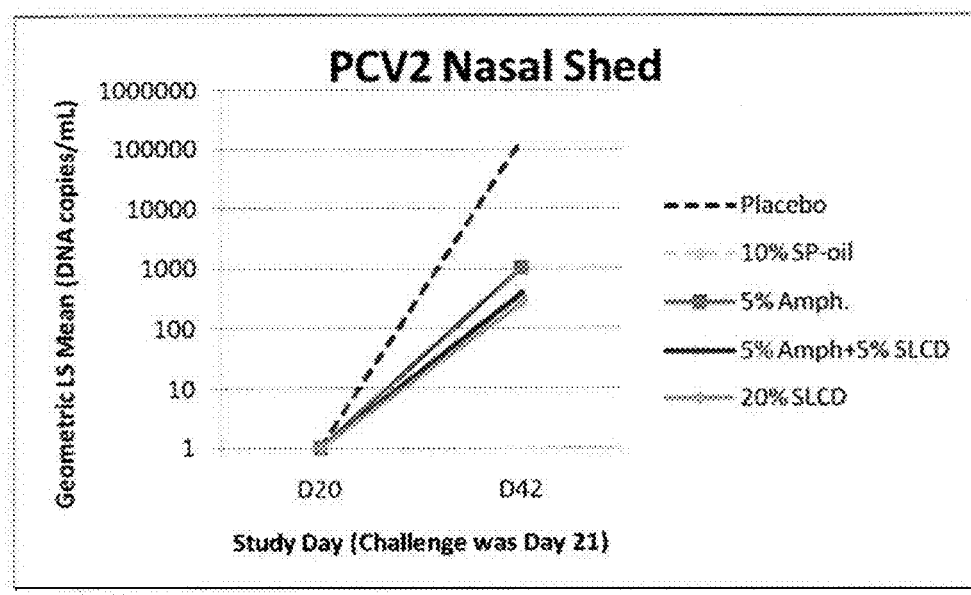
FIG. 6 is a graph showing the PCV2 nasal shed obtained with the T02-T04 treatments described in Example 7 vs. the placebo (T01). The results are expressed as PCV2 DNA copies/ml.

FIG. 6 is a graph showing the PCV2 nasal shed obtained with the T02-T04 treatments vs. the placebo (T01). These results are expressed as PCV2 DNA copies/ml. The results in FIG. 6 indicate that all treatments had significantly less nasal shed when compared to the placebo at day 42. In addition, 20% SLCD (T05) had significantly less nasal shed compared to 5% Amphigen (T03) at day 42. No other treatment differences were noted.

Figure 7A:
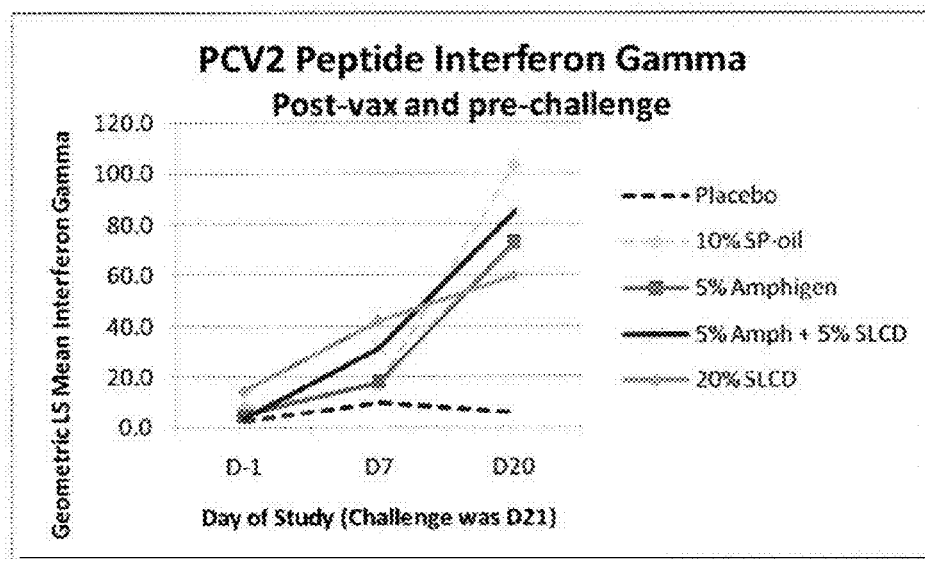
FIGS. 7 (A & B) are graphs showing the results of an interferon-gamma (IFN-γ) test that measures PCV2-specific cellular mediated immune (CMI) responses. The results of pos-vaccination/pre-challenge are presented in FIG. 7A, and the results of post-vaccination/post-challenge are presented in FIG. 7B. Stimulation of 5×10⁶ cells was considered significant.
Figure 7B:
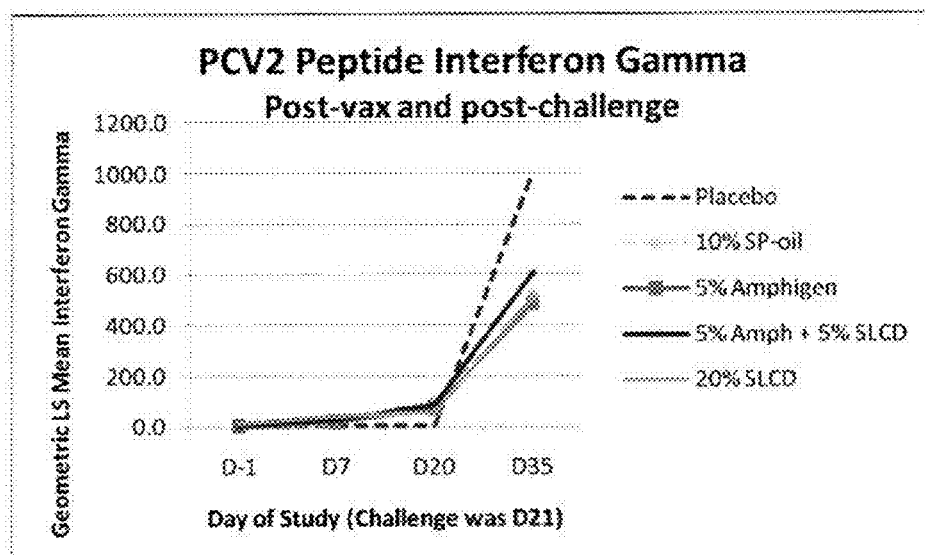

FIGS. 7 (A & B) are of two graphs showing the results of an interferon-gamma (IFN-γ) test that measures PCV2-specific cellular mediated immune (CMI) responses. The CMI results are shown post-vaccination/pre-challenge (FIG. 7A), and post-vaccination/post-challenge (FIG. 7B). In these graphs, stimulation of $5 \times 10^6$ cells was considered significant ( . . . ). All PCV2/*M. hyo* experiment vaccines gave a detectable IFN-γ response post-vaccination. The 10% SP-oil (T02) drove the strongest IFN-γ response post-vaccination. The 20% SLCD (T05) induced an earlier response, but the lowest response at day 20. There was a large post-challenge response, especially seen in the placebo group. Additionally, the post-challenge response was lower in the vaccinated pig treatment groups as compared to the placebo group.

Table 7 below shows the lymphoid depletion obtained with the experimental treatments contrasted to the placebo.

TABLE 7

PCV2 Histopathology (Lymphoid Depletion)

| Treatment | Lymphoid Depletion | | | Contrasted to Placebo | |
|---|---|---|---|---|---|
| | Positive | Negative | % Ever Pos. | P-value | Significant |
| Placebo | 9 | 7 | 56% | NA | NA |
| 10% SP-oil | 1 | 15 | 6% | 0.0059 | Yes |
| 5% Amphigen | 1 | 15 | 6% | 0.0059 | Yes |
| 5% Amph + 5% SLCD | 0 | 16 | 0% | 0.0008 | Yes |
| 20% SLCD | 1 | 15 | 6% | 0.0059 | Yes |

The results presented in Table 7 above show that all vaccines afforded strong protection against lymphoid depletion. Also, no statistically significant vaccine treatment contrasts were observed. Table 8 below shows the immunohistochemistry obtained with the experimental treatments contrasted to the placebo.

TABLE 8

PCV2 Histopathology (Immunohistochemistry)

| Treatment | Immunohistochemistry | | | Contrasted to Placebo | |
|---|---|---|---|---|---|
| | Positive | Negative | % Ever Pos. | P-value | Significant |
| Placebo | 12 | 4 | 75% | NA | NA |
| 10% SP-oil | 0 | 16 | 0% | 0.0001 | Yes |
| 5% Amphigen | 1 | 15 | 6% | 0.0002 | Yes |
| 5% Amph + 5% SLCD | 0 | 16 | 0% | 0.0001 | Yes |
| 20% SLCD | 0 | 16 | 6% | 0.0001 | Yes |

The results presented in Table 8 above show that all vaccines afforded strong protection against PCV2 colonization as evidenced by immunohistochemistry. Also, no statistically significant vaccine treatment contrasts were observed.

In conclusion, the results presented in this example demonstrate that the *M. hyo* soluble antigen preparation does not interfere with PCV2 efficacy. The results also show that all the PCV/*M. hyo* experimental vaccine formulations provide efficacy against PCV2 challenge. Additionally, the results indicate that there are some statistical and numerical differences obtained with the different adjuvant formulations, with 10% SP-oil yielding the strongest efficacy.

Example 8

Evaluation of *M. hyo* Efficacy of a 1-Bottle PCV2/*M. hyo* Combination Vaccine in with Different Adjuvant Formulations This study was designed to evaluate the *M. hyo* efficacy of a 1-bottle PCV2/*M. hyo* combination vaccine with different adjuvant formulations. The *M. hyo* antigen was combined with Porcine Circovirus (Type 1-Type 2 Chimera, or PCV1-2, killed virus) in one bottle.

Processing of Fluids:

Inactivated *M. hyo* fermentation fluid (described above in Example 1) was treated for each indicated group as follows.

T02-T04: These treatments were the same as those described for treatment groups T02-T04 in Example 7 above.

T05: This was formulated with inactivated *M. hyo* cells (*M. hyo* bacterin) as described in Example 1 above under the heading "Fermentation and Inactivation".

All experimental PCV2/*M. hyo* vaccines were formulated with different adjuvant formulations. The experimental vaccine formulations were prepared with *M. hyo* antigens processed according to treatments T02-T04. In addition, Treatment T01 corresponded to a placebo (sterile saline). Treatment T05 is a positive control corresponding to an expired RespiSure® vaccine, which is an *M. hyo* bacterin-based vaccine (Pfizer Animal Health).

These experimental formulations are described in Table 9 below, wherein the symbol * indicates the *M. hyo* antigen from global *M. hyo* seed, Protein A treated supernatant and the symbol ** indicates Investigational Veterinary Product (IVP) serial.

TABLE 9

PCV2/M.hyo Experimental Vaccine Formulations Used for M.hyo Efficacy Study in Different Adjuvant Formulations

| Treatment | IVP Serial ** | PCV1-2 Ag | M Hyo* Ag | Adjuvant | Other |
|---|---|---|---|---|---|
| T01 | 87-244-DK (Placebo) | | | NA | Sterile Saline |
| T02 | L0411RK08 | 1.6 RP | 7.5 RP | 10% SP Oil | NA |
| T03 | L0411RK09 | | | 5% Amphigen | |
| T04 | L0611RK03 | | | 5% Amphigen + 5% SLCD | |
| T05 | A827870 | | | Expired "RespiSure" vaccine | |

Pigs at 3 weeks of age were intramuscularly inoculated with a single dose of the different vaccine formulations described in Table 9 above. Fourteen animals were included in both the placebo and 10% SP-oil groups, thirteen animals were included in the positive control group, and sixteen animals were included in both the 5% Amphigen and 5% Amphigen+5% SLCD groups.

Animals were challenged 21 days after vaccination with a virulent M. hyo field isolate. Animals were necropsied 28 days after challenge and the lungs were removed and scored for consolidation consistent with M. hyo infection. Table 10 below contains the lung lesion scores for the respective treatment groups. Statistical significance was determined by a Mixed Model Analysis of lung scores fix each group.

TABLE 10

M.hyo Lung Lesions

| Treatment | # Animal | LS Mean Lung Lesion | Range % Lung Lesion |
|---|---|---|---|
| Placebo (T01) | 14 | 13.1% | 0.1-50.5 |
| 10% SP-oil (T02) | 14 | 4.3% | 0.0-50.8 |
| 5% Amphigen (T03) | 16 | 4.7% | 0.0-38.5 |
| 5% Amph + 5% SLCD (T04) | 16 | 12.0% | 0.1-55.8 |
| Expired RSO (T05) | 13 | 2.28% | 0.0-34.5 |

As indicated in Table 10 above, the placebo group had a mean lung lesion score of 13.1%, as compared to the 10% SP-oil and 5% Amphigen treatment groups which had mean lung scores of 4.3% and 4.7%, respectively. Roth the 10% SP-oil and 5% Amphigen formulations reduced and/or prevented lung lesions. Thus, the experimental PCV/M. hyo vaccines formulated with 10% SP-oil or 5% Amphigen were considered efficacious. The PCV2 antigen did not appear to interfere with the M. hyo efficacy of these formulations.

In contrast, the 5% Amphigen-1-5% SLCD group had a mean lung lesion score of 12.0%, which was an unacceptable result in that it was not different as compared to the placebo. Consequently, the experiment PCV/M. hyo vaccine formulated with 5% Amphigen+5% SLCD was not considered as efficacious.

It is noted that due to the reduced animal number and high variability in Ring lesion scoring, no statistical treatment effect could be conclusively demonstrated in this study. For this reason, it was decided that another study would be designed w test the M. hyo efficacy of the PCV/M. hyo experimental formulations in 10% SP-oil. This repeat study is presented in Example 9 below.

Example 9

Evaluation of M. hyo Efficacy of a 1-Bottle PCV2/M. hyo Combination Vaccine in 10% SP-Oil This study is a proof of concept designed to evaluate the M. hyo fraction efficacy of four experimental PCV2/M. hyo vaccines (Serials L0711RK11, L0711RK12, L0711RK13 and L0711RK14 in Table 11 below) prepared by different M. hyo manufacturing processes which utilize Protein A for IgG removal compared to control vaccines prepared with the standard M. hyo manufacturing process. Each of these four experimental PCV2/M. hyo vaccines included 10% SP-oil as the adjuvant.

Processing of Fluids:

T02: inactivated M. hyopnueumoniae antigen as described under "Fermentation and Inactivation" in Example 1 above.

T03 and T04: Formulated with inactivated M. hyopneumoniae cells as described under "Fermentation and Inactivation" in Example 1 above.

T05: Protein A treatment of medium used to grow M. hyopneumoniae. PPLO (porcine heart derived) was made per manufacturer's directions (i.e., 21 g/L) and yeast extract solution was made at 21 g/L in USP. Yeast extract solution was added to the PPLO at 6.25% and the mixture was sterilized by heating to 121° C. for ≥30 minutes. Cysteine hydrochloride was prepared at 90 g/L and filter sterilized. Dextrose solution was made by adding 450 g of dextrose per liter of USP water followed by heat sterilization. To prepare the final medium, porcine serum was added to the base medium at 10% followed by cysteine at 0.01% and dextrose at 1.0%. Antibodies in the complete PPLO media were removed by treatment with protein A. Briefly, one liter of rProtein A Sepharose (part number 17-5199-03 GE Healthcare) was packed into a glass column (10×11.5 cm). After removal of storage buffer, the column was treated with 2 column volumes of 1M acetic acid. The resin was equilibrated with 5 column volumes of 50 mM NaPO4, 1M NaCl buffer (pH 7.0). Fifteen liters of complete PPLO medium was loaded onto the resin at a linear flow rate of 140 cm/hour. The column flow through was collected and filter sterilized through a 0.2 micron filter (Sartorius). The treated medium was used propagate M. hyopneumoniae cells as described under "Fermentation and Inactivation" above. Whole inactivated culture (including cells) was formulated into the final vaccine.

T06: Inactivated M. hyopneumoniae cells were prepared as described under "Fermentation and Inactivation" in Example 1 above. The inactivated fermentation fluid was centrifuged at ~20,000×g (Sorvall RC5B) for 30 min. and the supernatant was sterilized via 0.2 uM filtration. One hundred fifteen rids of rProtein A resin (part number 12-1279-04, MAbSelect, GE Healthcare) was packed into a chromatography column (5×6 cm). After removal of the storage buffer and treatment with 2 column volumes of 1M acetic acid, the resin was equilibrated with 5 column volumes of 50 mM NaPO4/1M NaCl buffer, pH 7.01. Approximately 1.2 liters of the clarified/filtered M. hyopneumoniae antigen containing fluids were passed through the resin at a flow rate of 120 cm/hr. The flow through was collected and sterilized via 0.2 μM filter.

T07: Inactivated M. hyopneumoniae cells ere prepared as described under "Fermentation and Inactivation" in Example 1 above. The inactivated fermentation fluid was clarified by via tangential flow filtration. Briefly, a polyether sulfone filter (GE HealthCare, part number 56-4102-71) with nominal pore size of 0.2 μM was sanitized with 0.5N sodium hydroxide solution followed by extensive rinsing with sterile USP water. Inactivated mycoplasma culture fluid was introduced to the apparatus at a recirculation rate targeted to 14.6 L/minute and a transmembrane pressure of 2-3.4 PSI. Clarification was performed at room temperature. Filter permeate was collected and stored at 2-8 C until further processing. One hundred fifteen mls of rProtein A resin (part number 12-1279-04, MAbSelect, GE Healthcare) was packed into a chromatography column (5×6 cm). After removal of the storage buffer and treatment with 2 column volumes of 1M acetic acid, the resin was equilibrated with 5 column volumes of 50 mM NaPO4/1M NaCl buffer, pH 7.01. Approximately 2.3 liters of the clarified/filtered *M. hyopneumoniae* antigen containing fluids were passed through the resin at a flow rate of 120 cm/hr. The flow through was collected and sterilized via 0.2 µM filter.

T08: Inactivated *M. hyopneumoniae* cells were prepared as described under "Fermentation and Inactivation" above. The inactivated fermentation fluid was centrifuged at ~20,000×g (Sorvall RC5B) for 30 min. and the supernatant was sterilized via 0.2 uM filtration. One hundred fifteen ails of rProtein A Sepharose (part number 17-5199-03 GE, Healthcare) was packed into a chromatography column (5×6 cm). After removal of the storage buffer and treatment with 2 column volumes of 1M acetic acid, the resin was equilibrated with 5 column volumes of 50 niM NaPO4/1M NaCl buffer, pH 7.01. Approximately 1.2 liters of the clarified/filtered *M. hyopneumoniae* antigen containing fluids were passed through the resin at a flow rate of 120 cm/hr. The flow through was collected and sterilized via 0.2 uM filter.

The experimental vaccine formulations were prepared with *M. hyo* antigens processed according to treatments T02-T08 above. T02, T03 and T04 corresponded to positive controls. In addition, Treatment T01 corresponded to a placebo (sterile saline).

These experimental formulations are described in Table 11 below. The *M. hyo* antigen corresponds to the *M. hyo* antigen from global *M. hyo* seed, Protein A treated supernatant. The information in the "Protein A Treatment" column indicates whether the *M. hyo* supernatant was treated with Protein A either before or after fermentation.

Figures 8A, 8B:
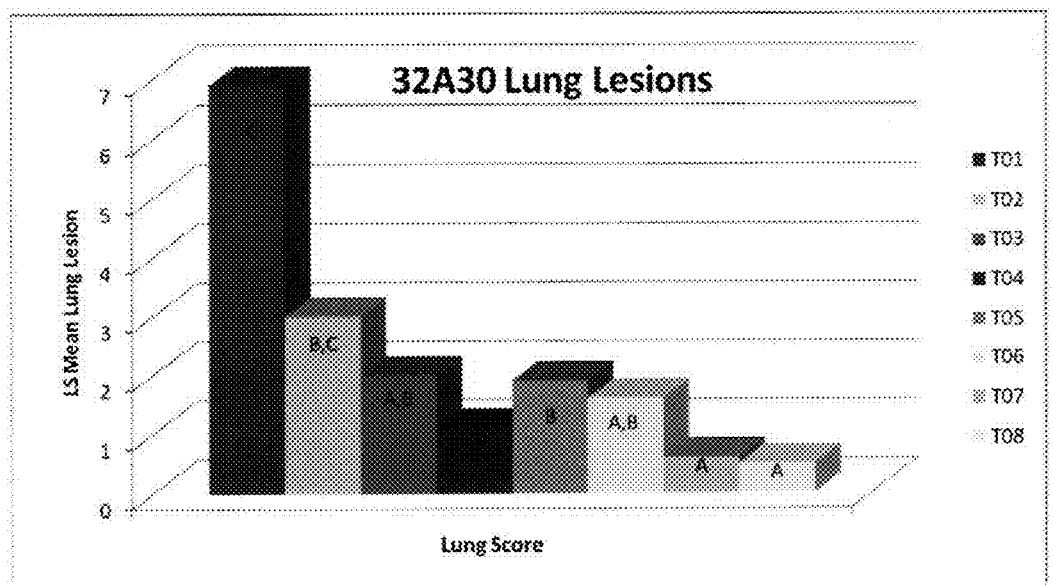
FIG. 8 depicts the *M. hyo* efficacy of the PCV experimental vaccine formulations in SP-oil. The lung scores thr formulations employing *M. hyo* treatments T02-T08 vs. a placebo (T01) are depicted graphically in FIG. 8A. The table in FIG. 5B depicts the contrast of treatments T02-T08 with the placebo.

The lung lesion results depicted in FIGS. 8A and 8B indicate that of all the treatments, only two (T07 and T08) had 100% of pigs in the <5% lung lesion category. It is noted that strong statistical difference were observed in this study.

The results in the present example demonstrate significant *M. hyo* efficacy in a 1-bottle PCV2/*M. hyo* experimental formulation employing the Protein A-treated *M. hyo* supernatant and utilizing SP-oil as the adjuvant. Additionally, Example 7 above demonstrated PCV2 efficacy in a 1-bottle PCV2/*M. hyo* formulation employing the Protein A-treated *M. hyo* supernatant and utilizing SP-oil as the adjuvant. Taken together, both *M. hyo* and PCV2 efficacy have been demonstrated in the 1-bottle PCV2/*M. hyo* combinations employing Protein A-treated *M. hyo* supernatant.

Example 10

In Vivo Safety of Experimental PCV2/*M. hyo* Experimental Vaccines

This study was conducted to evaluate in vivo safety of experimental PCV2-*M. hyo* vaccines formulated at maximum antigen dose in various adjuvant formulations in the host animal when given at the youngest age (3 weeks of age). Different adjuvant platforms were evaluated in order to determine which of these platforms provided an acceptable safety profile based on temperature, injection site reactions and clinical observations. A 20% SLCD/10% SP-oil formulation was used as a positive ("unsafe") control due to historic issues with injection site reactions observed by this investigative group and others.

Processing of Fluids:

All vaccines were prepared with inactivated *M. hyopneumoniae* antigen as described under "Fermentation and Inactivation" in Example 1. *M. hyo* whole bulk antigen was used since it was known to contain soluble and insoluble *M. hyo* antigens, in addition to the immunoglobulins and immunocomplexes that would be removed upon protein A treatment.

TABLE 11

PCV2/*M. hyo* Experimental Vaccine Formulations Used for *M. hyo* Efficacy Study in SP-Oil Adjuvant

| Treatment | Serial No. | PCV1-2 Ag | M. hyo Ag | Protein A Treatment | Supernatant Clarification Method | Protein A Brand | Adjuvant | Other |
|---|---|---|---|---|---|---|---|---|
| T01 | L0311AS11 | | | NA | | | | Sterile Saline |
| T02 | A828718 | NA | 13 | Expired RespiSure One | | | Amphigen | NA |
| T03 | L0711RK09 | 1.5 RP | 7.5 RP | M. hyo without Protein A treatment and with PCV-2 | | | 10% SP Oil | |
| T04 | L0711RK10 | NA | | M. hyo without Protein A treatment and without PCV-2 | | | | |
| T05 | L0711RK11 | 1.5 RP | | Before | NA | Sepharose | | |
| T06 | L0711RK12 | | | After | Centrifuge | MAbSelect | | |
| T07 | L0711RK13 | | | After | Filter | MAbSelect | | |
| T08 | L0711RK14 | | | After | Centrifuge | Sepharose | | |

Pigs at 3 weeks of age were intramuscularly inoculated with a single dose of the different vaccine formulations described in Table 11 above. There were 18 pigs included in each treatment group. Animals were challenged 21 days after vaccination with a virulent *M. hyo* field isolate. Animals were necropsied 28 days after challenge and the lungs were removed and scored for consolidation consistent with *M. hyo* infection. FIGS. 8 (A & B) show the lung lesion scores for the respective treatment groups. Statistical significance was determined by a Mixed Model Analysis of lung scores for each group.

It is reasonable to conclude that removal of insoluble cell debris and immunuoglobulins and immunocomplexes will only further enhance the safety of the vaccine formulations. The intention of this study was to stringently test the safety of the various adjuvant formulations containing PCV2 antigen and *M. hyo* antigen. The PCV2 and *M. hyo* antigens were formulated at maximum release levels to further assess safety. These experimental formulations are described in Table 12 below. IVP indicates Investigational Veterinary Product (IVP).

TABLE 12

PCV2/M.hyo Experimental Vaccine Formulations Used for Safety Study

| IVP Serial | PCV1-2 Ag | M Hyo* Ag | Adjuvant | Other | Minimum Vaccine Vol. (mL) |
|---|---|---|---|---|---|
| 87-244-DK (Placebo) | | NA | | Sterile Saline | NA |
| L0411RK15 | 7.8 RP | 13 RP | 10% SP Oil | NA | 200 |
| L0411RK16 | | | 5% Amphigen | | 200 |
| L0611RK05 | | | 5% Amphigen + 5% SLCD | | 200 |
| L0611RK06 | | | 20% SLCD + 10% SP Oil | | 200 |

*M hyo antigen = from global M hyo seed (whole bulk antigen).

The safety parameters employed in this study were rectal temperature profile and injection site reaction. The results of this study indicated that all candidate adjuvant platforms provided an acceptable safety profile in terms of rectal temperature profile and clinical observations (results not shown). Only the 20% SLCD+10% SP-oil (i.e., positive control) was significantly different than the placebo vaccine and had a number of severe injection site reactions (results not shown).

Example 11

Preparation of Protein A Treated M. hyo Antigen for Pivotal Studies

Figure 9:
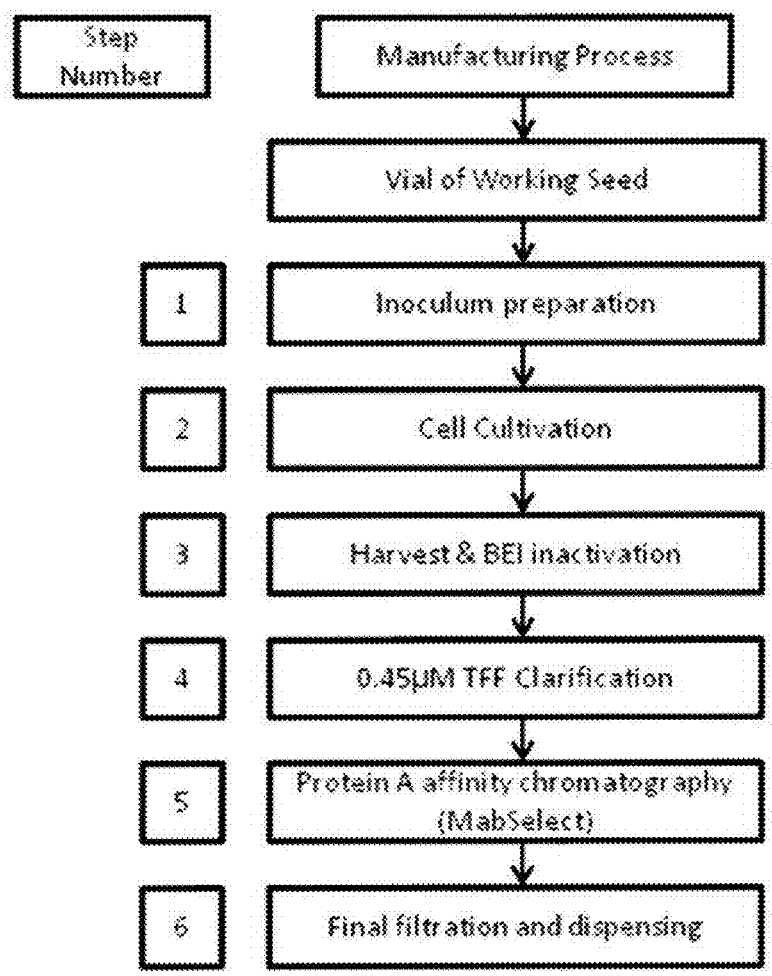
FIG. 9 is a flowchart which shows one embodiment of a manufacturing process used to prepare PCV2-compatible Protein-A treated *M. hyo* antigen.

FIG. 9 is a flowchart which snows one embodiment of a manufacturing process used to prepare PCV2 compatible Protein-A treated M. hyo antigen. Inactivated whole cultures of M. hyo were clarified of cells via tangential flow filtration. Briefly, a polyether sulfone filter (GE Healthcare, part number 56-4102-49) with nominal pore size of 0.45 µM was sanitized with 0.5N sodium hydroxide solution followed by extensive rinsing with sterile USP water. Inactivated *mycoplasma* culture fluid was introduced to the apparatus at a recirculation rate targeted to 11.0 L/minute and a transmembrane pressure of ~5 PSI. Clarification was performed at room temperature. Filter permeate was collected and stored at 2-8° C. until further processing.

Following clarification, antigen containing fluids were treated with protein A resin to reduce antibody levels. Briefly, MAbSeleet protein A resin (GE Healthcare) was packed into a glass column to a height of 12 cm. The resin was equilibrated with 5 column volumes of 50 mM sodium phosphate, 250 mM NaCl buffer (pH 7.0). Antigen containing fluid, equivalent to 10 column volumes, was loaded onto the resin at a linear flow rate of 100 cm/hour. The column for through was collected and filter sterilized through a 0.2 micron filter. Regeneration of the column was achieved by flowing 3 column volumes of 25 mM acetate solution at pH 3.7 followed by 4 column volumes of 1M acetic acid solution. Anti-PCV2 antibodies and M. hyopneumoniae antigen levels were measured in the final antigen fluid via PCV2 specific antibody ELISA and p46 antigen quantification ELISA, respectively.

Example 12

Efficacy of the PCV1-2 Chimeric Fraction Following Intramuscular Administration of a 1-Bottle PCV2/M. hyo Combination Vaccine in 10% SP-Oil The study presented in this example was designed to evaluate the efficacy of the PCV1-2 chimera, killed virus fraction of an experimental 1-Bottle PCV2/M. hyo combination vaccine, administered once to pigs of 21±3 days of age and challenged with a virulent PCV2 isolate at approximately 6 weeks of age.

Four experimental bivalent PCV1-2/M. hyo vaccines at different, but balanced, antigen dose levels and one experimental monovalent M. hyo (negative control) vaccine were formulated with the highest passage antigen. The M. hyo antigen control lot was prepared as described in Example 11 above. The PCV2 antigen was a killed cPCV1-2 antigen prepared as described in Example 2 above. Prior to inactivation of the chimeric virus, the PCV2 antigen lot was concentrated 20× and the concentrates were washed with a balanced salt solution. The final experimental vaccine formulations were adjuvanted using 10% SP oil. These experimental formulations are described below and in Table 13, wherein the antigen dose (% of the PCV2 and M. hyo antigen lots) is provided.

T01: Experimental preparation (L1211RK11) of M. hyo antigen (14.1%-High) without PCVType1-Type2 chimera, killed virus fraction (0%). This corresponds to a negative control (monovalent M. hyo).

T02: Experimental preparation (L1211RK09) of high passage PCVType1-Type2 chimera, killed virus (1.375%-High) and M. hyo antigen (14.1%-High).

T03: Experimental preparation (L1211RK15) of high passage PCVType1-Type2 chimera, killed virus (0.688%-Medium) and M. hyo antigen (9.4%-Medium).

T04: Experimental preparation (L0112RK03) of high passage PCVType1-Type2 chimera, killed virus (0.344%-Low) and M. hyo antigen (4.7%-Low).

T05: Experimental preparation (L1211RK17) of high passage PCVType1-Type2 chimera, killed virus (0.172%-Very Low) and M. hyo antigen (2.32%-Very Low).

TABLE 13

Experimental Design

| | | | Vaccination | | | | |
|---|---|---|---|---|---|---|---|
| Group | N | CR or IVP[1] | Serial/ Lot No. | Antigen Dose (PCV2/M hyo) | Adjuvant | Dose | Route |
| T01 | 24 | Placebo | L1211RK11 | None/High | 10% SP Oil | 2 mL | IM. Right neck |
| T02 | 24 | PCV2-M hyo | L1211RK09 | High/High | | | |
| T03 | 24 | PCV2-M hyo | L1211RK15 | Medium/Medium | | | |
| T04 | 24 | PCV2-M hyo | L0112RK03 | Low/Low | | | |

TABLE 13-continued

Experimental Design

| | | | Vaccination | | | | |
|---|---|---|---|---|---|---|---|
| Group | N | CR or IVP[1] | Serial/ Lot No. | Antigen Dose (PCV2/M hyo) | Adjuvant | Dose | Route |
| T05 | 24 | PCV2-M hyo | L1211RK17 | Very low/ Very low | | | |

[1]IVP = Porcine Circovirus Type 1-Type 2 Chimera (PCV2), Killed Virus vaccine-*Mycoplasma Hyopneumoniae* (M hyo) Bacterial Extract
CP = *Mycoplasma Hyopneumoniae* bacterial extract adjuvanted with SP-oil 10% (without Porcine Circovirus Type 1 - Type 2 Chimera fraction)
IM = Intramuscularly On Day 0 (3 weeks of age) a single 2 mL dose of the assigned vaccine was administered by IM injection in the right neck of each pig enrolled in the study. No adverse events were observed post vaccination. A serum sample was collected from all pigs weekly prior to challenge. Any pig detected with PCV2 viremia prior to challenge was removed from the study. On the day prior to challenge fecal swabs and serum samples were collected. The pigs were subsequently challenged with a PCV2a challenge virus. Challenge was conducted around 3 weeks after the vaccination (Day 21). Each pig was inoculated with a total 3 ml, of PCV2a challenge virus (Isolate #40895, pre-diluted to 5.10 $\log_{10}$ $FAID_{50}$/mL) with 2 mL intranasally and 1 mL intramuscularly in the left neck. A reserved aliquot of the challenge virus was titrated following the challenge to confirm the actual challenge dose. The undiluted hulk was prediluted 2-fold and the back-titer results achieved a 5.10 $\log_{10}$ $FAID_{50}$/mL challenge level. Prior to necropsy, serum and fecal swabs were collected weekly during the three-week challenge phase. At three weeks post challenge all pigs were euthanized and necropsied. Serum samples and fecal swabs were collected, along with 4 different lymphoid tissues. During necropsy, sections of three lymph nodes (tracheobronchial, mesenteric, inguinal), and tonsil were collected for each pig and individually identified and fixed in 10% buffered formalin solution. The results of testing are provided below.

Vaccine Potency Testing

The L1211RK15 PCV/M. hyo vaccine serial described above was considered to be the reference candidate. Consequently, relative potency for both the M. hyo fraction and the PCV2 fraction were determined versus this candidate reference. These results are presented in Table 14 below. Serial L1211RK11 corresponds to the placebo (no PCV2 fraction).

TABLE 14

Potency Results

Reference L1211RK15

| Serial | M. hyo Potency | PCV Potency |
|---|---|---|
| L1211RK11 | 1.57 | 0.00 |
| L1211RK09 | | 2.08 |
| L1211RK15 | | 1.05 |
| L0112RK03 | | 0.56 |
| L1211RK17 | | 0.27 |

Results shown for each serial are averages of all replicates tested.

PCV2 Viremia

Following challenge, when compared to the placebo group, all vaccinated groups had a significant reduction in the percent of viremic pigs [P≤0.05], and throughout the study at least 47% of pigs in the treated groups (T02-T05) stayed negative for PCV2 viremia (Table 15 below). Similarly, all vaccine groups had significantly lower (P=0.0001) PCV2 DNA copy numbers than the placebo group post challenge (data not shown).

TABLE 15 qPCR Qualitative Serum Viremia - Percent Ever Positive and Estimate of Prevented Fraction

| | | Ever Positive? | | | | Total | |
|---|---|---|---|---|---|---|---|
| | | Pos | | Neg | | Observations | |
| Trt | Vaccine | # | % | # | % | Number | P-Value |
| T01 | L1211RK11 | 23 | 95.8 | 1 | 4.2 | 24 | |
| T02 | L1211RK09 | 2 | 8.3 | 22 | 91.7 | 24 | <0.0001 |
| T03 | L1211RK15 | 7 | 31.8 | 15 | 68.2 | 22 | 0.0006 |
| T04 | L0112RK03 | 12 | 52.2 | 11 | 47.8 | 23 | 0.0063 |
| T05 | L1211RK17 | 7 | 29.2 | 17 | 70.8 | 24 | 0.0004 |

PCV2 Fecal Shedding

Post-challenge fecal swabs revealed 83.3% of the placebo group pigs (T01) were positive for PCV2 fecal shedding. In contrast, all vaccine groups (T02-T05) had a significant reduction in the percent of pigs shedding PCR detectable PCV2 DNA (P≤0.00611. These results are presented in Table 16 below. Similarly, all vaccine groups bad significantly lower PCV2 DNA copy number than the placebo group post challenge (data not shown).

TABLE 16

Fecal Shedding Ever Present after Challenge (Day > 21)

| | | Fecal Ever Positive? | | | | Total | |
|---|---|---|---|---|---|---|---|
| | | Pos | | Neg | | Observations | |
| Trt | Vaccine | # | % | # | % | Number | P-Value |
| T01 | L1211RK11 | 20 | 83.3 | 4 | 16.7 | 24 | |
| T02 | L1211RK09 | 6 | 25.0 | 18 | 75.0 | 24 | 0.0002 |
| T03 | L1211RK15 | 9 | 40.9 | 13 | 59.1 | 22 | 0.0049 |
| T04 | L0112RK03 | 10 | 43.5 | 13 | 56.5 | 23 | 0.0061 |
| T05 | L1211RK17 | 6 | 25.0 | 18 | 75.0 | 24 | 0.0002 |

Serum Antibody Response

All pigs were PCV2 seronegative prior to vaccination. Pigs in the Placebo group remained seronegative prior to challenge. In contrast, pigs in all vaccine groups except for the T05 group showed significant increases (P≤0.0287) of PCV2 antibody titer on Day 20 post vaccination when compared to placebo, indicating the active immune response to PCV2 following vaccination, PCV2 ELISA antibody titers are summarized in Table 17 below. Pre-challenge titers indicated a significant difference (P≤0.0393) in the T02 and T03 groups from the T01 group on Days 7-20 and between the T01 and T04 groups on Day 20 (P≤0.0287). On Days 28 through 42, all vaccine groups had significantly higher titers than T01 (P≤0.0129; Table 17 below).

TABLE 17

PCV2 ELISA S/P Titers Treatment Comparison by Study Day

| Contrast | Day −1 | Day 07 | Day 14 | Day 20 | Day 28 | Day 35 | Day 42 |
|---|---|---|---|---|---|---|---|
| T01 vs T02 | ns | 0.0229 | 0.0005 | 0.0001 | <0.0001 | <0.0001 | 0.0056 |
| T01 vs T03 | ns | 0.0302 | 0.0393 | 0.0060 | <0.0001 | <0.0001 | 0.0024 |
| T01 vs T04 | ns |  | ns | 0.0287 | <0.0001 | <0.0001 | 0.0114 |
| T01 vs T05 | ns |  | ns | ns | <0.0001 | <0.0001 | 0.0129 |

*When contrast is significant (≤0.05) a P-value is reported, P-values > 0.05 are designated as ns (not significant)

Lymphoid Lesions and Colonization

At the time of necropsy, when compared to the placebo group, all vaccinated groups had a significant reduction in total amount of PCV2 antigen detected in tissues. The data concerning PCV2 infection in Lymphoid Tissues (IHC scores) are summarized in Table 18 below. As show Table 18, all vaccine groups had significantly lower IHC scores than the T01 placebo group.

TABLE 18

PCV2 IHC Scores: If lymphoid or tonsil tissues ever abnormal

| Treatment | LSM | Compared to L12111RK11 P-value |
|---|---|---|
| L1211RK11 | 0.75 |  |
| L1211RK09 | 0.15 | 0.0003 |
| L1211RK15 | 0.30 | 0.0055 |
| L0112RK03 | 0.34 | 0.0106 |
| L1211RK17 | 0.41 | 0.0273 |

*Animal was considered abnormal if score was >0 in any lymphoid tissue or tonsil sample.

All vaccinated groups also saw a significant reduction in PCV2 Lymphoid Depletion as shown in Table 19 below.

TABLE 19

PCV2 Lymphoid Depletion: If lymphoid or tonsil tissues ever abnormal

| Treatment | LSM | Compared to L12111RK11 P-value |
|---|---|---|
| L1211RK11 | 0.48 |  |
| L1211RK09 | 0.04 | 0.0053 |
| L1211RK15 | 0.13 | 0.0181 |
| L0112RK03 | 0.08 | 0.0069 |
| L1211RK17 | 0.11 | 0.0116 |

*Animal was considered abnormal if score was >0 in any lymphoid tissue or tonsil sample.

Additionally, all vaccinated groups saw a significant reduction in Histiocytic Replacement as shown in Table 20 below.

TABLE 20

PCV2 Histiocytic Replacement: if lymphoid or tonsil tissues ever abnormal

| Treatment | LSM** | Compared to L12111RK11 P-value |
|---|---|---|
| L1211RK11 | ND |  |
| L1211RK09 | ND | 0.0006 |
| L1211RK15 | ND | 0.0098 |
| L0112RK03 | ND | 0.0098 |
| L1211RK17 | ND | 0.0173 |

* Animal was considered abnormal if score was >0 in any lymphoid tissue or tonsil sample.
** Fisher exact test was used due to non-convergence, therefore least square means were not determined (ND).

The data presented in this Example indicates; that the vaccine groups:
  Significantly protected and aided in the prevention of PCV2 viremia post-challenge;
  Significantly aided in the prevention of fecal shedding of PCV2 post-challenge in all vaccinated animals;
  Elicited a statistically significant serological response 28 days post vaccination in groups T02-T05. In addition, T02 and T03 demonstrated a statistically significant response as early as 7 days post-vaccination when compared to T01;
  Significantly reduced microscopic lesions (Lymphoid Depletion and Histiocytic replacement) in all vaccinated animals; and
  All vaccines proved to be efficacious and vaccine serial L1211RK15 was selected as a reference candidate.

Example 13

Efficacy of the M. hyo Fraction Following Intramuscular Administration of a 1-Bottle PCV2/M. hyo Combination Vaccine in 10% SP-Oil The objective of the study presented in this example was to evaluate efficacy of the *Mycoplasma hyopneumoniae* (*M. hyopneumoniae*) fraction of an experimental Porcine Circovirus (PCV) Type 1-Type 2 Chimera, Killed Virus-*Mycoplasma Hyopneumoniae* (*M. hyo*) Bacterial Extract, administered intramuscularly once to pigs of 21±3 days of age and challenged with a virulent lung homogenate of *M. hyopneumaniae* at 7 weeks after vaccination.

Four experimental bivalent PCV1-2/M. hyo vaccines at different, but balanced, antigen dose levels and one experimental monovalent PCV2 (negative control) vaccine were formulated. The *M. hyo* antigen control lot was prepared as described in Example 11 above. The PCV2 antigen was as killed cPCV1-2 antigen prepared as described in Example 2 above. Prior to inactivation of the chimeric virus, the PCV2 antigen lot was concentrated 20× and the concentrates were washed with a balanced salt solution. The final experimental vaccine formulations were adjuvanted using 10% SP oil. These experimental formulations are described below and in Table 21 below, wherein the antigen dose (% of the PCV2 and *M. hyo* antigen lots) is provided.

T01: Experimental preparation (L1211RK10) of high passage PCVType1-Type2 chimera, killed virus (1.375%-High) without *M. hyo* fraction (0%). This corresponds to to negative control (monovalent PCV2).

T02: Experimental preparation (L1211RK09) of high passage PCVType1-Type2 chimera, killed virus (1.375%-High) and *M. hyo* antigen (14.1%-High).

T03: Experimental preparation (L1211RK15) of high passage PCVType1-Type2 chimera, killed virus (0.688%-Medium) and M. hyo antigen (9.4%-Medium).

TABLE 21

Experimental Design

| Group | N | CP or IVP[1] | Serial/Lot No. | Antigen dose RP (PCV2/M hyo) | Adjuvant | Dose | Route |
|---|---|---|---|---|---|---|---|
| NTX | 9 | Sentinel | NA | | No Vaccination | | |
| T01 | 38 | Placebo-PCV2 | L1211RK10 | High/None | 10% SP | 2 mL | IM, Left neck |
| T02 | 38 | PCV2-M hyo | L1211RK09 | High/High | Oil | | |
| T03 | 38 | PCV2-M hyo | L1211RK15 | Medium/Medium | | | |

[1]IVP = Investigational Veterinary Product = Porcine Circovirus Type 1-Type 2 Chimera (PCV2), Killed Virus vaccine-Mycoplasma Hyopneumoniae (M hyo) Bacterial Extract
CP = Control Product = Killed Chimeric PCV1-2 fraction adjuvanted with SP-oil 10% adjuvanted (with M. hyopneumoniae fraction)
IM = Intramuscularly On Day 0, 123 clinically healthy susceptible pigs were enrolled in this study at three weeks of age. Pigs were blocked by litter and randomly assigned to a sentinel (NIX) group or one of the three treatment groups (T01-T03); administered intramuscularly 2 mL of either an experimental PCV1-2/M. hyopneumoniae vaccine at the minimum immunizing dose (MID), an experimental PCV1-2/M. hyopneumoniae vaccine at a dose slightly higher than MID or a placebo containing PCV1-2 only at MID. Seven weeks after vaccination the sentinel pigs were euthanized and necropsied to confirm absence of M. hyopneumoniae and all treated pigs were challenged twice (on two successive days) with a live, virulent M. hyopneumoniae lung homogenate. All retraining pigs were euthanized and necropsied four weeks after challenge. At necropsy lungs were scored for lesions typical of M. hyopneumoniae. Post-challenge lung lesions are the primary outcome variable. Vaccination is considered effective if the lower 95% confidence interval of the mitigated fraction is >0.

Vaccine Potency Testing

The L1211RK15 PCV/M. hyo vaccine serial described above was considered to be the reference candidate. Consequently, relative potency for both the M. hyo fraction and the PCV2 fraction used in this M. hyo efficacy study were determined versus this candidate reference. These results are presented in Table 22 below. Serial L1211RK10 corresponds to the placebo (no M. hyo fraction

TABLE 22

Potency Results

Reference L1211RK15

| Serial | M. hyo[1] Potency | PCV Potency[2] |
|---|---|---|
| L1211RK10 | 0.00 | 2.33 |
| L1211RK09 | 1.48 | 2.20 |
| L1211RK15 | 1.00 | 1.07 |

Results shown for each serial are averages of all replicates tested.
[1]M. hyopneumoniae potency tested in five replicates.
[2]PCV potency tested in one replicate (L1211RK10), or five (L1211RK09, L1211RK15) replicates.

Serology

M. hyo antibody titers indicated that all pigs were serologically M. hyopneumoniae negative on Day 0 and remained negative prior to challenge. At all time points post vaccination (Days 21, 47 and 75) T02 and T03 had significantly higher (P≤0004) geometric least squares mean M. hyopneumoniae antibody titers compared to T01 (serology data not shown).

Percentage of Total Lung with Lesions

Frequency distributions of lung lesion scores for each lung lobe were calculated by treatment. Percentage of total lung with lesions was calculated using the following formula: Percentage of total lung with lesions={(0.10×left cranial)+(0.10×left middle)+(0.25×left caudal)+(0.10×right cranial)+(0.10×right middle)+(0.25×right caudal)+(0.10×accessory)}. The arcsine square root transformation was applied to the percentage of total lung with lesions prior to analysis. Percentage of Total Lung with Lesions was analyzed using a mixed linear model. Pair-wise comparisons were made between treatment groups if the treatment effect was significant. Back transformed least squares means of percentage of total lung with lesions, and their 95% confidence intervals were calculated as well as the minimums and maximums. Lung lesions were summarized with the stratified mitigated fraction and 95% confidence limits. The lung lesion results are presented in Table 23 below.

TABLE 23

Analysis of Percent of Total Lung with Lesion
Summary of Least Squares Means

| | | | % Lung with | | Mitigated Fraction | |
|---|---|---|---|---|---|---|
| Group | Serial | N | Lesion[1] | Range | Contrast vs T01 | 95% CI[4] |
| NTX | | 9 | 0.1 | 0.0 to 0.8 | | |
| T01 | L1211RK10 | 36 | 6.1[b] | 0.0 to 32.3 | | |
| T02 | L1211RK09 | 36 | 2.7[a] | 0.0 to 23.5 | 40.9 | 13.3 to 61.8 |
| T03 | L1211RK15 | 38 | 2.6[a] | 0.0 to 49.0 | 46.9 | 18.2 to 68.3 |

[1]Back Transformed Least Squares Mean
[a]Confidence Interval
Treatment groups with the same letter are not significantly different at P-value 0.05.

A few low percentage lung lesions were observed in the NIX pig lungs which were attributed to a known incidence of Bordetella in this herd. Bacterial culture on lung tissue swabs confirmed several pigs were B. bronchiseptica culture positive and M. hyopneumoniae culture confirmed all NIX pigs were M. hyopneumoniae culture negative prior to challenge administration.

The protocol met the validity criteria in that the LS mean lung lesions for T01 were >4%. The LS Mean lung lesions for T02 and T03 were significantly (P≤0.05) lower than T01 and both met the mitigated fraction criteria that the lower 95% confidence interval was >0. The validity requirements of this study were met in that there was no evidence of pre-challenge exposure to M. hyopneumoniae. The challenge was valid in that the back-transformed mean lung lesion scores in placebo pigs (T01) was >4%.

Compared to the negative control group (T01), treatment groups T02 and T03 demonstrated a significant reduction (P≤0.05) in percent lung with lesion compared to T01. The mitigated fractions for T02 and T03 compared to T01 met the protocol criteria for efficacy.

Under the conditions of this study, both vaccines (T02 & T03) helped to mitigate lung lesions, the primary variable for efficacy. The results in the present example demonstrate significant *M. hyo* efficacy in a 1-bottle PCV2/*M. hyo* experimental formulation.

Example 14

Evaluation of Virucidal Activity Against PRRS Virus

The studies presented in this example were designed to evaluate the various adjuvant platforms for virucidal activity against PRRS virus. Initial experiments focused on adjuvant alone (i.e., the formulations did not contain PCV or *M. hyo* antigens). The adjuvant evaluation for PRRS virucidal activity is presented in FIG. 10. Preliminary virucidal assessment indicated that 10% SP-oil, 0.2% Carbopol and 2.5% Amphigen are non-virucidal to PRRS virus. In contrast, the 20% SLCD adjuvant appeared to be virucidal to PRRS virus.

Further studies were performed to evaluate whether the PCV/*M. hyo* formulations adjuvanted with the different adjuvant platforms were non-virucidal to PRRS virus. These results are presented in Table 24 below, wherein the symbol * indicates those vaccine serials which were virucidal to PRRS virus.

TABLE 24

Results of PRRS Virucidal Assay with Different Formulations

| Vaccine Serial | | | Potency | | PRRS Virucidal | |
|---|---|---|---|---|---|---|
| Used in Studies of Examples 7, 8, 10 | | | p46 RP | PCV2 NVSL | | |
| Study | Description | Serial # | (ru/ds) | RP | A | B |
| Examples 7, 8, 10 | Sterile Saline (0.9% Sodium chloride) | 87-244-DK (Placebo) | | | | |
| Examples 7, 8 | cPCV (RP 1.6) + *M Hyo* Prot A treated (RP 7.5) in 10% SP Oil | L0411RK08 | 7.1 | 1.29 | −0.10 | −0.13 |
| Examples 7, 8 | cPCV (RP 1.6) + *M Hyo* Prot A treated (RP 7.5) in 5% Amphigen | L0411RK09 | 7.3 | 1.33 | −0.10 | +0.14 |
| Examples 7, 8 | cPCV (RP 1.6) + *M Hyo* Prot A treated (RP 7.5) in 5% Amph + 5% SLCD | L0611RK03 | 6.9 | 1.15 | −0.36 | −0.33 |
| Example 7 | cPCV (RP 1.6) monovalent in 20% SLCD | L0611RK04 | | 1.50 | −1.86* | −0.50 |
| Example 8 | Expired RespiSure One serial | A827870 | 12.6 | | | |
| Example 10 | cPCV (RP 7.8) + *M Hyo* Whole Bulk (RP 13.3) in 10% SP Oil | L0411RK15 | 14 | 1.03 | −0.32 | −0.03 |
| Example 10 | cPCV (RP 7.8) + *M Hyo* Whole Bulk (RP 13.3) in 5% Amphigen | L0411RK16 | 15.5 | 1.12 | −0.36 | −0.53 |
| Example 10 | cPCV (RP 7.8) + *M Hyo* Whole Bulk (RP 13.3) in 5% Amph + 5% SLCD | L0611RK05 | 17.5 | 1.50 | −0.54 | −0.33 |
| Example 10 | cPCV (RP 7.8) + *M Hyo* Whole Bulk (RP 13.3) in 20% SLCD + 10% SP Oil | L0611RK06 | 15.9 | 1.13 | −1.93* | −0.99* |

*Indicates Virucidal (>0.7 log loss)
A-Virucidal assay control GMT ~5.53 log/mL
B-Virucidal assay control GMT ~6.42 log/mL The results presented in Table 24 above indicate that 10% SP-oil is non-virucidal to PRRS virus. Further PCV/*M. hyo* vaccine serials were prepared using 10% SP-oil as the adjuvant (Table 25). The antigenic potency of these vaccine serials was compared to a Reference PCV/*M. hyo* vaccine serial (L1211RK15) described above. The results shown in Table 25 below flintier indicate that 10% SP-oil is non-virucidal to PRRS virus. The test sample values in Table 25 were each higher (+sign) than the virucidal assay control, which had a geometric mean titer (GMT) of about 5.9±0.5 log/ml.

TABLE 25

Results of Virucidal Assay with Different PCV/*M.hyo* Formulations Adjuvanted with 10% SP-oil

| | | Vaccine Serial Used | | |
| --- | --- | --- | --- | --- |
| | | Potency | | |
| Description | Serial # | p46 RP (ru/ds) Reference L1211RK15 | PCV2 NVSL Reference L1211RK15 | PRRS Virucidal log10 TCID50/mL |
| Sterile Diluent (sterile water) | 1949122 | na | na | |
| cPCV + *M Hyo* Prot A treated in 10% SP Oil | L0912RK12 | 1.62 | 2.60 | +0.58 |
| cPCV + *M Hyo* Prot A treated in 10% SP Oil | L0912RK10 | 0.88 | 1.23 | +0.58 |
| cPCV + *M Hyo* Prot A treated in 10% SP Oil | L0912RK11 | 1.24 | 2.62 | +0.58 |
| cPCV + *M Hyo* Prot A treated in 10% SP Oil | L0912RK08 | 1.08 | 1.03 | +0.91 |
| cPCV + *M Hyo* Prot A treated in 10% SP Oil | L0912RK09 | 1.65 | 2.06 | +0.50 |

Virucidal Assay control GMT ~ 5.9 ± 0.5 log/ml

The results presented in this example demonstrate that 10% SP-oil is non-virucidal to PRRS virus. The results presented in this example further demonstrate that the PCV/*M. hyo* formulation adjuvanted with 10% SP-oil was among those vaccine serials which were considered non-virucidal to PRRS virus (Table 24 and Table 25). In conclusion, the PCV/*M. hyo* formulation adjuvanted with 10% SP-oil was considered an effective platform on which to base a trivalent combination including PCV, *M. hyo*, and nits virus.

Example 15

Preparation of a PCV/*M. hyo*/PRRS Combination Vaccine

A PCV/*M. hyo* formulation adjuvanted with an adjuvant platform which is non-virucidal to PRRS virus (see Tables 24 and 25 above), is provided as a ready-to-use in one-bottle liquid composition. This 1-bottle PCV/*M. hyo* formulation employs Protein A-treated *M. hyo* supernatant. Both *M. hyo* and PCV2 efficacy have been demonstrated in such PCV2/*M. hyo* formulations employing *M. hyo* Protein A-treated supernatant (see Examples 7-9). In the present example, this divalent PCV2/*M. hyo* tot ululation is combined with a monovalent PRRS virus antigen.

In one embodiment, a PCV/*M. hyo* combination in 10% SP-oil and corresponding to one of the vaccine serials L0711RK11, L0711RK12, L0711RK13 and L0711RK14 in Table 11 above or L1211RK09, L1211RK15, L0112RK03 and L1211RK17 in Table 13 above is provided as a ready-to-use in one bottle liquid composition. The results presented in Example 14 above demonstrated that 10% SP-oil is non-virucidal to PRRS virus. Example 14 also demonstrated that PCV2/*M. hyo* formulations adjuvanted with 10% SP-oil were among those vaccine serials which were considered non-virucidal to PRRS virus. In the present example, such a 1-bottle PCV2/*M. hyo* liquid composition is used to re-hydrate a lyophilized genetically modified live PRRS virus composition contained in a second bottle, such that all antigens are contained in a single bottle prior to being administered to a pig of a suitable age (e.g., at 3 weeks of age or older).

In one embodiment, the PRRS virus has the genomic sequence corresponding to SEQ ID NO: 16 or a variant thereof. In another embodiment, the PRRS virus employed in the trivalent composition is the PRRS virus isolate designated ISU-55, which was deposited in the ATCC under the accession number VR 2430. Suitable amounts of the respective antigens are described herein. Desirably, all antigens are administered in a single dose to the pig.

What is claimed is:

1. A multivalent immunogenic composition comprising a soluble portion of a *Mycoplasma hyopneumoniae* (*M. hyo*) whole cell preparation; and a porcine circovirus type 2 (PCV2) antigen, wherein the soluble portion of the *M. hyo* preparation comprises *M. hyo*-specific soluble protein antigens and is substantially free of insoluble material and both (i) IgG and (ii) immunocomplexes comprised of antigen bound to immunoglobulin.

2. The composition of claim 1, wherein the soluble portion of the *M. hyo* preparation has been treated with protein-A or protein-G prior to being added to the immunogenic composition.

3. The composition of claim 1, wherein the composition is in the form of a ready-to-use liquid composition.

4. The composition of claim 1, wherein the composition elicits a protective immune response in a pig against *M. hyo* and PCV2.

5. The composition of claim 1, wherein the PCV2 antigen is in the form of a chimeric type-1-type 2 circovirus, said chimeric virus comprising an inactivated recombinant porcine circovirus type 1 expressing the porcine circovirus type 2 ORF2 protein.

6. The composition of claim 1, wherein the PCV2 antigen is in the form of a recombinant ORF2 protein.

7. The composition of claim 6, wherein the recombinant ORF2 protein is expressed from a baculovirus vector.

8. The composition of claim 1, further comprising at least one additional antigen.

9. The composition of claim 8, wherein the at least one additional antigen is protective against a microorganism that can cause disease in pigs.

10. The composition of claim 9, wherein the composition elicits a protective immune response against *M. hyo*, PCV2 and at least one additional microorganism that is known to infect pigs when administered as a single dose administration.

11. The composition of claim 9, wherein the microorganism comprises bacteria, viruses, or protozoans.

12. The composition of claim 11, wherein the microorganism is selected from the group consisting of porcine reproductive and respiratory syndrome virus (PRRSV), porcine parvovirus (PPV), *Haemophilus parasuis, Pasteurella multocida, Streptococcum suis, Staphylococcus hyicus, Actinobacilllus pleuropneumoniae, Bordetella bronchiseptica, Salmonella choleraesuis, Salmonella enteritidis, Erysipelothrix rhusiopathiae, Mycoplama hyorhinis, Mycoplasma hyosynoviae, leptospira bacteria, Lawsonia intracellularis*, swine influenza virus (SIV), *Escherichia coli* antigen, *Brachyspira hyodysenteriae*, porcine respiratory coronavirus, Porcine Epidemic Diarrhea (PED) virus, rotavirus, Torque teno virus (TTV), Porcine Cytomegalovirus, Porcine enteroviruses, Encephalomyocarditis virus, a pathogen causative of Aujesky's Disease, Classical Swine fever (CSF) and a pathogen causative of Swine Transmissable Gastroenteritis, or combinations thereof.

13. The composition of claim 1, wherein the composition further comprises an adjuvant.

14. The composition of claim 13, wherein the adjuvant is selected from the group consisting of an oil-in-water adjuvant, a polymer and water adjuvant, a water-in-oil adjuvant, an aluminum hydroxide adjuvant, a vitamin E adjuvant and combinations thereof.

15. The composition of claim 1, wherein the composition further comprises a pharmaceutically acceptable carrier.

16. The composition of claim 1, wherein the composition elicits a protective immune response against both *M. hyo* and PCV2 when administered as a single dose administration.

17. A method of immunizing a pig against *Mycoplasma hyopneumoniae* (*M. hyo*) and PCV2 which comprises administering to the pig the composition of claim 1.

18. The method of claim 17, wherein the composition is administered intramuscularly, intradermally, transdermally, or subcutaneously.

19. The method of claim 17, wherein the composition is administered in a single dose.

20. The method of claim 17, wherein the composition is administered in conjunction with at least one additional antigen that is protective against a microorganism that is known to infect pigs.

21. The method of claim 20, wherein the microorganism is selected from the group consisting of porcine reproductive and respiratory syndrome virus (PRRSV), porcine parvovirus (PPV), *Haemophilus parasuis, Pasteurella multocida, Streptococcum suis, Staphylococcus hyicus, Actinobacilllus pleuropneumoniae, Bordetella bronchiseptica, Salmonella choleraesuis, Salmonella enteritidis, Erysipelothrix rhusiopathiae, Mycoplama hyorhinis, Mycoplasma hyosynoviae, leptospira bacteria, Lawsonia intracellularis*, swine influenza virus (SIV), *Escherichia coli* antigen, *Brachyspira hyodysenteriae*, porcine respiratory coronavirus, Porcine Epidemic Diarrhea (PED) virus, rotavirus, Torque teno virus (TTV), Porcine Cytomegalovirus, Porcine enteroviruses, Encephalomyocarditis virus, a pathogen causative of Aujesky's Disease, Classical Swine fever (CSF) and a pathogen causative of Swine Transmissable Gastroenteritis, or combinations thereof.

22. The method of claim 17, wherein the composition is administered to pigs having maternally derived antibodies against at least one of *M. hyo* and PCV2.

23. The method of claim 22, wherein the composition is administered to pigs having maternally derived antibodies against both *M. hyo* and PCV2.

24. The method of claim 17, wherein the composition is administered to pigs at 3 weeks of age or older.

25. A kit comprising: a bottle comprising an immunogenic composition including both a PCV2 antigen and the soluble portion of a *Mycoplasma hyopneumoniae* (*M. hyo*) whole cell preparation, wherein the soluble portion of the *M. hyo* preparation comprises *M. hyo*-specific soluble protein antigens and is substantially free of insoluble material and both (i) IgG and (ii) antigen/immunoglobulin immunocomplexes.

26. The kit of claim 25, wherein the immunogenic composition in the bottle is provided as a ready-to-use liquid composition.

* * * * *